(12) United States Patent
Jung et al.

(10) Patent No.: US 10,541,184 B2
(45) Date of Patent: Jan. 21, 2020

(54) OPTICAL EMISSION SPECTROSCOPIC TECHNIQUES FOR MONITORING ETCHING

(71) Applicant: Applied Materials, Inc., Santa Clara, CA (US)

(72) Inventors: Soonwook Jung, San Jose, CA (US); Soonam Park, Sunnyvale, CA (US); Dmitry Lubomirsky, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 15/646,845

(22) Filed: Jul. 11, 2017

(65) Prior Publication Data

US 2019/0019734 A1 Jan. 17, 2019

(51) Int. Cl.
*H01L 21/3065* (2006.01)
*H01L 21/66* (2006.01)
(Continued)

(52) U.S. Cl.
CPC ............ *H01L 22/26* (2013.01); *G01N 21/31* (2013.01); *G01N 21/67* (2013.01);
(Continued)

(58) Field of Classification Search
CPC ...... H01L 21/26; H01L 21/3065; H01L 22/26
See application file for complete search history.

(56) References Cited

U.S. PATENT DOCUMENTS 2,369,620 A 2/1945 Sullivan et al.
3,401,302 A 9/1968 Thorpe
(Continued)

FOREIGN PATENT DOCUMENTS

CN 1124364 A 6/1996
CN 1847450 A 10/2006
(Continued)

OTHER PUBLICATIONS

International Search Report and Written Opinion of PCT/US2017/047209 dated Nov. 24, 2017, all pages.
(Continued)

*Primary Examiner* — Thomas T Pham
(74) *Attorney, Agent, or Firm* — Kilpatrick Townsend & Stockton LLP

(57) ABSTRACT

Embodiments may include a method of etching. The method may also include flowing a gas mixture through a plasma discharge to form plasma effluents. The method may further include flowing the plasma effluents through a plurality of apertures to a layer on a substrate. The layer may have a first thickness. In addition, the method may include etching the layer with the plasma effluents. The method may also include measuring the intensity of emission from a reaction of plasma effluents with the layer. The method may further include summing the intensity of the emission while the plasma effluents are being flowed to the layer to obtain an integrated intensity. The method may then include comparing the integrated intensity to a reference value corresponding to a target etch thickness. The method may include extinguishing the plasma discharge when the integrated intensity is equal to or greater than the reference value.

18 Claims, 11 Drawing Sheets

(51) Int. Cl.
  *H01L 21/67* (2006.01)
  *G01N 21/31* (2006.01)
  *G01N 21/67* (2006.01)

(52) U.S. Cl.
  CPC .... *H01L 21/3065* (2013.01); *H01L 21/67069* (2013.01); *H01L 21/67253* (2013.01)

(56) References Cited

U.S. PATENT DOCUMENTS

| | | |
|---|---|---|
| 3,451,840 A | 6/1969 | Hough |
| 3,537,474 A | 11/1970 | Rohrer |
| 3,756,511 A | 9/1973 | Shinroku |
| 3,937,857 A | 2/1976 | Brummett et al. |
| 3,969,077 A | 7/1976 | Hill |
| 4,006,047 A | 2/1977 | Brummett et al. |
| 4,190,488 A | 2/1980 | Winters |
| 4,209,357 A | 6/1980 | Gorin et al. |
| 4,214,946 A | 7/1980 | Forget et al. |
| 4,232,060 A | 11/1980 | Mallory, Jr. |
| 4,234,628 A | 11/1980 | DuRose |
| 4,265,943 A | 5/1981 | Goldstein et al. |
| 4,340,462 A | 7/1982 | Koch |
| 4,341,592 A | 7/1982 | Shortes et al. |
| 4,361,418 A | 11/1982 | Tscheppe |
| 4,361,441 A | 11/1982 | Tylko |
| 4,364,803 A | 12/1982 | Nidola et al. |
| 4,368,223 A | 1/1983 | Kobayashi et al. |
| 4,374,698 A | 2/1983 | Sanders et al. |
| 4,397,812 A | 8/1983 | Mallory, Jr. |
| 4,468,413 A | 8/1984 | Bachmann |
| 4,565,601 A | 1/1986 | Kakehi et al. |
| 4,579,618 A | 4/1986 | Celestino et al. |
| 4,585,920 A | 4/1986 | Hoog et al. |
| 4,600,464 A | 7/1986 | Desliets et al. |
| 4,610,775 A | 9/1986 | Phifer |
| 4,625,678 A | 12/1986 | Shloya et al. |
| 4,632,857 A | 12/1986 | Mallory, Jr. |
| 4,656,052 A | 4/1987 | Satou et al. |
| 4,656,076 A | 4/1987 | Vetanen et al. |
| 4,668,335 A | 5/1987 | Mockler |
| 4,690,746 A | 9/1987 | McInerney et al. |
| 4,715,937 A | 12/1987 | Moslehi et al. |
| 4,749,440 A | 6/1988 | Blackwood et al. |
| 4,753,898 A | 6/1988 | Parrillo et al. |
| 4,786,360 A | 11/1988 | Cote et al. |
| 4,792,378 A | 12/1988 | Rose et al. |
| 4,793,897 A | 12/1988 | Dunfield et al. |
| 4,807,016 A | 2/1989 | Douglas |
| 4,810,520 A | 3/1989 | Wu |
| 4,816,638 A | 3/1989 | Ukai et al. |
| 4,820,377 A | 4/1989 | Davis et al. |
| 4,828,649 A | 5/1989 | Davis |
| 4,857,140 A | 8/1989 | Loewenstein |
| 4,867,841 A | 9/1989 | Loewenstein et al. |
| 4,904,621 A | 2/1990 | Lowenstein et al. |
| 4,913,929 A | 4/1990 | Moslehi et al. |
| 4,919,750 A | 4/1990 | Bausmith et al. |
| 4,946,903 A | 8/1990 | Gardella et al. |
| 4,951,601 A | 8/1990 | Maydan et al. |
| 4,960,488 A | 10/1990 | Law et al. |
| 4,980,018 A | 12/1990 | Mu et al. |
| 4,981,551 A | 1/1991 | Palmour |
| 4,985,372 A | 1/1991 | Narita et al. |
| 4,991,542 A | 2/1991 | Kohmura et al. |
| 4,992,136 A | 2/1991 | Tachi et al. |
| 4,993,358 A | 2/1991 | Mahawili |
| 4,994,404 A | 2/1991 | Sheng et al. |
| 5,000,113 A | 3/1991 | Wang et al. |
| 5,006,192 A | 4/1991 | Deguchi |
| 5,010,842 A | 4/1991 | Oda et al. |
| 5,013,691 A | 5/1991 | Lory et al. |
| 5,028,565 A | 7/1991 | Chang |
| 5,030,319 A | 7/1991 | Nishino et al. |
| 5,038,713 A | 8/1991 | Kawakami et al. |
| 5,045,244 A | 9/1991 | Marlett |
| 5,061,838 A | 10/1991 | Lane et al. |
| 5,069,938 A | 12/1991 | Lorimer et al. |
| 5,074,456 A | 12/1991 | Degner et al. |
| 5,083,030 A | 1/1992 | Stavov |
| 5,089,441 A | 2/1992 | Moslehi |
| 5,089,442 A | 2/1992 | Olmer |
| 5,147,692 A | 9/1992 | Bengston |
| 5,156,881 A | 10/1992 | Okano et al. |
| 5,180,435 A | 1/1993 | Markunas et al. |
| 5,186,718 A | 2/1993 | Tepman et al. |
| 5,188,706 A | 2/1993 | Hori et al. |
| 5,198,034 A | 3/1993 | deBoer et al. |
| 5,200,016 A | 4/1993 | Namose |
| 5,203,911 A | 4/1993 | Sricharoenchalkit et al. |
| 5,215,787 A | 6/1993 | Homma |
| 5,221,427 A | 6/1993 | Koinuma et al. |
| 5,228,501 A | 7/1993 | Tepman et al. |
| 5,231,690 A | 7/1993 | Soma et al. |
| 5,235,139 A | 8/1993 | Bengston et al. |
| 5,238,499 A | 8/1993 | van de Ven et al. |
| 5,240,497 A | 8/1993 | Shacham et al. |
| 5,248,371 A | 9/1993 | Maher et al. |
| 5,248,527 A | 9/1993 | Uchida et al. |
| 5,252,178 A | 10/1993 | Moslehi |
| 5,266,157 A | 11/1993 | Kadomura |
| 5,269,881 A | 12/1993 | Sekiya |
| 5,270,125 A | 12/1993 | America et al. |
| 5,271,972 A | 12/1993 | Kwok et al. |
| 5,275,977 A | 1/1994 | Otsubo et al. |
| 5,277,750 A | 1/1994 | Wolgang |
| 5,279,669 A | 1/1994 | Lee |
| 5,279,865 A | 1/1994 | Chebi et al. |
| 5,288,518 A | 2/1994 | Homma |
| 5,290,382 A | 3/1994 | Zarowin et al. |
| 5,290,383 A | 3/1994 | Koshimizu |
| 5,292,370 A | 3/1994 | Tsai et al. |
| 5,292,682 A | 3/1994 | Stevens et al. |
| 5,300,463 A | 4/1994 | Cathey et al. |
| 5,302,233 A | 4/1994 | Kim et al. |
| 5,304,250 A | 4/1994 | Sameshima et al. |
| 5,306,530 A | 4/1994 | Strongin et al. |
| 5,314,724 A | 5/1994 | Tsukune et al. |
| 5,319,247 A | 6/1994 | Matsuura |
| 5,326,427 A | 7/1994 | Jerbic |
| 5,328,558 A | 7/1994 | Kawamura et al. |
| 5,328,810 A | 7/1994 | Lowrey et al. |
| 5,330,578 A | 7/1994 | Sakama |
| 5,334,552 A | 8/1994 | Homma |
| 5,345,999 A | 9/1994 | Hosokawa |
| 5,352,636 A | 10/1994 | Beinglass |
| 5,356,478 A | 10/1994 | Chen et al. |
| 5,362,526 A | 11/1994 | Wang et al. |
| 5,366,585 A | 11/1994 | Robertson et al. |
| 5,368,897 A | 11/1994 | Kurihara et al. |
| 5,378,316 A | 1/1995 | Franke et al. |
| 5,380,560 A | 1/1995 | Kaja et al. |
| 5,382,311 A | 1/1995 | Ishikawa et al. |
| 5,384,284 A | 1/1995 | Doan et al. |
| 5,385,763 A | 1/1995 | Okano et al. |
| 5,399,237 A | 3/1995 | Keswick et al. |
| 5,399,529 A | 3/1995 | Homma |
| 5,403,434 A | 4/1995 | Moslehi |
| 5,413,670 A | 5/1995 | Langan et al. |
| 5,413,967 A | 5/1995 | Matsuda et al. |
| 5,415,890 A | 5/1995 | Kloiber et al. |
| 5,416,048 A | 5/1995 | Blalock et al. |
| 5,420,075 A | 5/1995 | Homma et al. |
| 5,429,995 A | 7/1995 | Nishiyama et al. |
| 5,439,553 A | 8/1995 | Grant et al. |
| 5,451,259 A | 9/1995 | Krogh |
| 5,464,499 A | 11/1995 | Moslehi |
| 5,468,342 A | 11/1995 | Nulty et al. |
| 5,474,589 A | 12/1995 | Ohga et al. |
| 5,478,403 A | 12/1995 | Shinigawa et al. |
| 5,478,462 A | 12/1995 | Walsh |
| 5,483,920 A | 1/1996 | Pryor |
| 5,494,494 A | 2/1996 | Mizuno et al. |
| 5,500,249 A | 3/1996 | Telford et al. |
| 5,505,816 A | 4/1996 | Barnes et al. |

(56) References Cited

U.S. PATENT DOCUMENTS

| | | |
|---|---|---|
| 5,510,216 A | 4/1996 | Calabrese et al. |
| 5,516,367 A | 5/1996 | Lei et al. |
| 5,518,962 A | 5/1996 | Murao |
| 5,531,835 A | 7/1996 | Fodor et al. |
| 5,534,070 A | 7/1996 | Okamura et al. |
| 5,536,360 A | 7/1996 | Nguyen et al. |
| 5,549,780 A | 8/1996 | Koinuma et al. |
| 5,556,521 A | 9/1996 | Ghanbari |
| 5,558,717 A | 9/1996 | Zhao et al. |
| 5,560,779 A | 10/1996 | Knowles et al. |
| 5,563,105 A | 10/1996 | Dobuzinsky et al. |
| 5,567,243 A | 10/1996 | Foster et al. |
| 5,571,576 A | 11/1996 | Qian et al. |
| 5,575,853 A | 11/1996 | Arami et al. |
| 5,578,130 A | 11/1996 | Hayashi et al. |
| 5,578,161 A | 11/1996 | Auda |
| 5,580,385 A | 12/1996 | Paranjpe et al. |
| 5,580,421 A | 12/1996 | Hiatt et al. |
| 5,591,269 A | 1/1997 | Arami et al. |
| 5,592,358 A | 1/1997 | Shamouilian |
| 5,595,606 A | 1/1997 | Fujikawa et al. |
| 5,597,439 A | 1/1997 | Salzman |
| 5,599,740 A | 2/1997 | Jang et al. |
| 5,614,055 A | 3/1997 | Fairbairn et al. |
| 5,616,518 A | 4/1997 | Foo et al. |
| 5,624,582 A | 4/1997 | Cain |
| 5,626,922 A | 5/1997 | Miyanaga et al. |
| 5,628,829 A | 5/1997 | Foster et al. |
| 5,635,086 A | 6/1997 | Warren, Jr. |
| 5,645,645 A | 7/1997 | Zhang et al. |
| 5,648,125 A | 7/1997 | Cane |
| 5,648,175 A | 7/1997 | Russell et al. |
| 5,656,093 A | 8/1997 | Burkhart et al. |
| 5,660,957 A | 8/1997 | Chou et al. |
| 5,661,093 A | 8/1997 | Ravi et al. |
| 5,670,066 A | 9/1997 | Barnes et al. |
| 5,674,787 A | 10/1997 | Zhao et al. |
| 5,676,758 A | 10/1997 | Hasgawa et al. |
| 5,679,606 A | 10/1997 | Wang et al. |
| 5,685,946 A | 11/1997 | Fathauer et al. |
| 5,688,331 A | 11/1997 | Aruga et al. |
| 5,695,810 A | 12/1997 | Dubin et al. |
| 5,712,185 A | 1/1998 | Tsai et al. |
| 5,716,500 A | 2/1998 | Bardos et al. |
| 5,716,506 A | 2/1998 | Maclay et al. |
| 5,719,085 A | 2/1998 | Moon et al. |
| 5,733,816 A | 3/1998 | Iyer et al. |
| 5,747,373 A | 5/1998 | Yu |
| 5,753,886 A | 5/1998 | Iwamura et al. |
| 5,755,859 A | 5/1998 | Brusic et al. |
| 5,756,400 A | 5/1998 | Ye et al. |
| 5,756,402 A | 5/1998 | Jimbo et al. |
| 5,772,770 A | 6/1998 | Suda et al. |
| 5,781,693 A | 7/1998 | Ballance et al. |
| 5,786,276 A | 7/1998 | Brooks et al. |
| 5,788,825 A | 8/1998 | Park et al. |
| 5,789,300 A | 8/1998 | Fulford |
| 5,792,376 A | 8/1998 | Kanai et al. |
| 5,800,686 A | 9/1998 | Littau et al. |
| 5,804,259 A | 9/1998 | Robles |
| 5,812,403 A | 9/1998 | Fong et al. |
| 5,814,238 A | 9/1998 | Ashby et al. |
| 5,814,365 A | 9/1998 | Mahawill |
| 5,820,723 A | 10/1998 | Benjamin et al. |
| 5,824,599 A | 10/1998 | Schacham-Diamand et al. |
| 5,830,805 A | 11/1998 | Schacham-Diamand et al. |
| 5,835,334 A | 11/1998 | McMillin et al. |
| 5,843,538 A | 12/1998 | Ehrsam et al. |
| 5,843,847 A | 12/1998 | Pu et al. |
| 5,844,195 A | 12/1998 | Fairbairn et al. |
| 5,846,332 A | 12/1998 | Zhao et al. |
| 5,846,373 A | 12/1998 | Pirkle et al. |
| 5,846,375 A | 12/1998 | Gilchrist et al. |
| 5,846,598 A | 12/1998 | Semkow et al. |
| 5,849,639 A | 12/1998 | Molloy et al. |
| 5,850,105 A | 12/1998 | Dawson et al. |
| 5,855,681 A | 1/1999 | Maydan et al. |
| 5,855,685 A | 1/1999 | Tobe et al. |
| 5,856,240 A | 1/1999 | Sinha et al. |
| 5,858,876 A | 1/1999 | Chew |
| 5,863,376 A | 1/1999 | Wicker |
| 5,865,896 A | 2/1999 | Nowak |
| 5,866,483 A | 2/1999 | Shiau et al. |
| 5,868,897 A | 2/1999 | Ohkawa |
| 5,872,052 A | 2/1999 | Iyer |
| 5,872,058 A | 2/1999 | Van Cleemput et al. |
| 5,882,424 A | 3/1999 | Taylor et al. |
| 5,882,786 A | 3/1999 | Nassau et al. |
| 5,883,012 A | 3/1999 | Chiou |
| 5,885,404 A | 3/1999 | Kim et al. |
| 5,885,749 A | 3/1999 | Huggins et al. |
| 5,888,906 A | 3/1999 | Sandhu et al. |
| 5,891,349 A | 4/1999 | Tobe et al. |
| 5,891,513 A | 4/1999 | Dubin et al. |
| 5,897,751 A | 4/1999 | Makowiecki |
| 5,899,752 A | 5/1999 | Hey et al. |
| 5,900,163 A | 5/1999 | Yi et al. |
| 5,904,827 A | 5/1999 | Reynolds |
| 5,907,790 A | 5/1999 | Kellam |
| 5,910,340 A | 6/1999 | Uchida et al. |
| 5,913,147 A | 6/1999 | Dubin et al. |
| 5,913,978 A | 6/1999 | Kato et al. |
| 5,915,190 A | 6/1999 | Pirkle |
| 5,918,116 A | 6/1999 | Chittipeddi |
| 5,919,332 A | 7/1999 | Koshiishi et al. |
| 5,920,792 A | 7/1999 | Lin |
| 5,926,737 A | 7/1999 | Ameen et al. |
| 5,928,528 A | 7/1999 | Kubota et al. |
| 5,932,077 A | 8/1999 | Reynolds |
| 5,933,757 A | 8/1999 | Yoshikawa et al. |
| 5,935,334 A | 8/1999 | Fong et al. |
| 5,935,340 A | 8/1999 | Xia et al. |
| 5,937,323 A | 8/1999 | Orczyk et al. |
| 5,939,831 A | 8/1999 | Fong et al. |
| 5,942,075 A | 8/1999 | Nagahata et al. |
| 5,944,049 A | 8/1999 | Beyer et al. |
| 5,944,902 A | 8/1999 | Redeker et al. |
| 5,948,702 A | 9/1999 | Rotondaro |
| 5,951,601 A | 9/1999 | Lesinski et al. |
| 5,951,776 A | 9/1999 | Selyutin et al. |
| 5,951,896 A | 9/1999 | Mahawill |
| 5,953,591 A | 9/1999 | Ishihara et al. |
| 5,953,635 A | 9/1999 | Andideh |
| 5,963,840 A | 10/1999 | Xia et al. |
| 5,968,379 A | 10/1999 | Zhao et al. |
| 5,968,587 A | 10/1999 | Frankel et al. |
| 5,968,610 A | 10/1999 | Liu et al. |
| 5,969,422 A | 10/1999 | Ting et al. |
| 5,976,327 A | 11/1999 | Tanaka |
| 5,982,100 A | 11/1999 | Ghanbari |
| 5,990,000 A | 11/1999 | Hong et al. |
| 5,990,013 A | 11/1999 | Berenguer et al. |
| 5,993,916 A | 11/1999 | Zhao et al. |
| 5,994,209 A | 11/1999 | Yieh et al. |
| 5,997,649 A | 12/1999 | Hillman |
| 5,997,962 A | 12/1999 | Ogasawara et al. |
| 6,004,884 A | 12/1999 | Abraham |
| 6,007,635 A | 12/1999 | Mahawill |
| 6,007,785 A | 12/1999 | Liou |
| 6,010,962 A | 1/2000 | Liu et al. |
| 6,013,191 A | 1/2000 | Nasser-Faili et al. |
| 6,013,584 A | 1/2000 | M'Saad |
| 6,015,724 A | 1/2000 | Yamazaki et al. |
| 6,015,747 A | 1/2000 | Lopatin et al. |
| 6,017,414 A | 1/2000 | Koemtzopoulos et al. |
| 6,019,848 A | 2/2000 | Kiyama et al. |
| 6,020,271 A | 2/2000 | Yanagida |
| 6,030,666 A | 2/2000 | Lam et al. |
| 6,030,881 A | 2/2000 | Papasouliotis et al. |
| 6,035,101 A | 3/2000 | Sajoto et al. |
| 6,036,878 A | 3/2000 | Collins et al. |
| 6,037,018 A | 3/2000 | Jang et al. |
| 6,037,266 A | 3/2000 | Tao et al. |
| 6,039,834 A | 3/2000 | Tanaka et al. |

(56) References Cited

U.S. PATENT DOCUMENTS

| | | |
|---|---|---|
| 6,039,851 A | 3/2000 | Iyer |
| 6,053,982 A | 4/2000 | Halpin et al. |
| 6,059,643 A | 5/2000 | Hu et al. |
| 6,063,683 A | 5/2000 | Wu et al. |
| 6,063,712 A | 5/2000 | Gilton et al. |
| 6,065,424 A | 5/2000 | Shacham-Diamand et al. |
| 6,065,425 A | 5/2000 | Takaki et al. |
| 6,072,147 A | 6/2000 | Koshiishi |
| 6,072,227 A | 6/2000 | Yau et al. |
| 6,074,512 A | 6/2000 | Collins et al. |
| 6,074,514 A | 6/2000 | Bjorkman et al. |
| 6,077,384 A | 6/2000 | Collins et al. |
| 6,077,780 A | 6/2000 | Dubin |
| 6,079,356 A | 6/2000 | Umotoy et al. |
| 6,080,529 A | 6/2000 | Ye et al. |
| 6,081,414 A | 6/2000 | Flanigan et al. |
| 6,083,344 A | 7/2000 | Hanawa et al. |
| 6,083,844 A | 7/2000 | Bui-Le et al. |
| 6,086,677 A | 7/2000 | Umotoy et al. |
| 6,087,278 A | 7/2000 | Kim et al. |
| 6,090,212 A | 7/2000 | Mahawill |
| 6,093,457 A | 7/2000 | Okumura |
| 6,093,594 A | 7/2000 | Yeap et al. |
| 6,099,697 A | 8/2000 | Hausmann |
| 6,107,199 A | 8/2000 | Allen et al. |
| 6,110,530 A | 8/2000 | Chen et al. |
| 6,110,832 A | 8/2000 | Morgan et al. |
| 6,110,836 A | 8/2000 | Cohen et al. |
| 6,110,838 A | 8/2000 | Loewenstein |
| 6,113,771 A | 9/2000 | Landau et al. |
| 6,114,216 A | 9/2000 | Yieh et al. |
| 6,117,245 A | 9/2000 | Mandrekar et al. |
| 6,120,640 A | 9/2000 | Shih et al. |
| 6,124,003 A | 9/2000 | Mikami et al. |
| 6,126,753 A | 10/2000 | Shinriki et al. |
| 6,132,512 A | 10/2000 | Horie et al. |
| 6,136,163 A | 10/2000 | Cheung et al. |
| 6,136,165 A | 10/2000 | Moslehi et al. |
| 6,136,685 A | 10/2000 | Narwankar et al. |
| 6,136,693 A | 10/2000 | Chan et al. |
| 6,140,234 A | 10/2000 | Uzoh et al. |
| 6,144,099 A | 11/2000 | Lopatin et al. |
| 6,147,009 A | 11/2000 | Grill et al. |
| 6,148,761 A | 11/2000 | Majewski et al. |
| 6,149,828 A | 11/2000 | Vaartstra |
| 6,150,628 A | 11/2000 | Smith et al. |
| 6,153,935 A | 11/2000 | Edelstein et al. |
| 6,161,500 A | 12/2000 | Kopacz et al. |
| 6,161,576 A | 12/2000 | Maher et al. |
| 6,162,302 A | 12/2000 | Raghavan et al. |
| 6,162,370 A | 12/2000 | Hackett et al. |
| 6,165,912 A | 12/2000 | McConnell et al. |
| 6,167,834 B1 | 1/2001 | Wang et al. |
| 6,169,021 B1 | 1/2001 | Akram et al. |
| 6,170,428 B1 | 1/2001 | Redeker et al. |
| 6,171,661 B1 | 1/2001 | Zheng et al. |
| 6,174,450 B1 | 1/2001 | Patrick et al. |
| 6,174,810 B1 | 1/2001 | Patrick et al. |
| 6,174,812 B1 | 1/2001 | Hsuing et al. |
| 6,176,198 B1 | 1/2001 | Kao et al. |
| 6,176,667 B1 | 1/2001 | Fairbairn |
| 6,177,245 B1 | 1/2001 | Ward et al. |
| 6,179,924 B1 | 1/2001 | Zhao et al. |
| 6,180,523 B1 | 1/2001 | Lee et al. |
| 6,182,602 B1 | 2/2001 | Redeker et al. |
| 6,182,603 B1 | 2/2001 | Shang et al. |
| 6,184,121 B1 | 2/2001 | Buchwalter et al. |
| 6,184,489 B1 | 2/2001 | Ito et al. |
| 6,186,091 B1 | 2/2001 | Chu et al. |
| 6,189,483 B1 | 2/2001 | Ishikawa et al. |
| 6,190,233 B1 | 2/2001 | Hong et al. |
| 6,194,038 B1 | 2/2001 | Rossman |
| 6,197,181 B1 | 3/2001 | Chen |
| 6,197,364 B1 | 3/2001 | Paunovic et al. |
| 6,197,680 B1 | 3/2001 | Lin et al. |
| 6,197,688 B1 | 3/2001 | Simpson |
| 6,197,705 B1 | 3/2001 | Vassiliev |
| 6,198,616 B1 | 3/2001 | Dahimene et al. |
| 6,200,412 B1 | 3/2001 | Kilgore et al. |
| 6,203,863 B1 | 3/2001 | Liu et al. |
| 6,204,200 B1 | 3/2001 | Shieh et al. |
| 6,210,486 B1 | 4/2001 | Mizukami et al. |
| 6,217,658 B1 | 4/2001 | Orczyk et al. |
| 6,220,201 B1 | 4/2001 | Nowak |
| 6,225,745 B1 | 5/2001 | Srivastava |
| 6,228,233 B1 | 5/2001 | Lakshmikanthan et al. |
| 6,228,751 B1 | 5/2001 | Yamazaki et al. |
| 6,228,758 B1 | 5/2001 | Pellerin et al. |
| 6,235,643 B1 | 5/2001 | Mui et al. |
| 6,237,527 B1 | 5/2001 | Kellerman et al. |
| 6,238,513 B1 | 5/2001 | Arnold et al. |
| 6,238,582 B1 | 5/2001 | Williams et al. |
| 6,197,151 B1 | 6/2001 | Kaji et al. |
| 6,241,845 B1 | 6/2001 | Gadgil et al. |
| 6,242,349 B1 | 6/2001 | Nogami et al. |
| 6,242,360 B1 | 6/2001 | Fischer et al. |
| 6,244,211 B1 | 6/2001 | Nishikawa et al. |
| 6,245,396 B1 | 6/2001 | Nogami |
| 6,245,670 B1 | 6/2001 | Cheung et al. |
| 6,251,236 B1 | 6/2001 | Stevens |
| 6,251,802 B1 | 6/2001 | Moore et al. |
| 6,258,170 B1 | 7/2001 | Somekh et al. |
| 6,258,220 B1 | 7/2001 | Dordi et al. |
| 6,258,223 B1 | 7/2001 | Cheung et al. |
| 6,258,270 B1 | 7/2001 | Hilgendorff et al. |
| 6,261,637 B1 | 7/2001 | Oberle |
| 6,267,074 B1 | 7/2001 | Okumura |
| 6,277,733 B1 | 8/2001 | Smith |
| 6,277,752 B1 | 8/2001 | Chen |
| 6,277,763 B1 | 8/2001 | Kugimiya et al. |
| 6,281,072 B1 | 8/2001 | Li et al. |
| 6,281,135 B1 | 8/2001 | Han et al. |
| 6,284,146 B1 | 9/2001 | Kim et al. |
| 6,291,282 B1 | 9/2001 | Wilk et al. |
| 6,291,348 B1 | 9/2001 | Lopatin et al. |
| 6,302,964 B1 | 10/2001 | Umotoy et al. |
| 6,303,044 B1 | 10/2001 | Koemtzopoulos |
| 6,303,418 B1 | 10/2001 | Cha et al. |
| 6,306,772 B1 | 10/2001 | Lin |
| 6,308,654 B1 | 10/2001 | Schneider et al. |
| 6,308,776 B1 | 10/2001 | Sloan |
| 6,310,755 B1 | 10/2001 | Busato et al. |
| 6,312,554 B1 | 11/2001 | Ye |
| 6,312,995 B1 | 11/2001 | Yu |
| 6,319,387 B1 | 11/2001 | Krishnamoorthy et al. |
| 6,321,587 B1 | 11/2001 | Laush |
| 6,322,716 B1 | 11/2001 | Qiao et al. |
| 6,323,128 B1 | 11/2001 | Sambucetti et al. |
| 6,335,288 B1 | 1/2002 | Kwan et al. |
| 6,340,435 B1 | 1/2002 | Bjorkman et al. |
| 6,342,733 B1 | 1/2002 | Hu et al. |
| RE37,546 E | 2/2002 | Mahawill |
| 6,344,410 B1 | 2/2002 | Lopatin et al. |
| 6,348,407 B1 | 2/2002 | Gupta et al. |
| 6,350,320 B1 | 2/2002 | Sherstinsky et al. |
| 6,350,697 B1 | 2/2002 | Richardson |
| 6,351,013 B1 | 2/2002 | Luning et al. |
| 6,352,081 B1 | 3/2002 | Lu et al. |
| 6,355,573 B1 | 3/2002 | Okumura |
| 6,358,827 B1 | 3/2002 | Chen et al. |
| 6,364,949 B1 | 4/2002 | Or et al. |
| 6,364,954 B2 | 4/2002 | Umotoy et al. |
| 6,364,957 B1 | 4/2002 | Schneider et al. |
| 6,375,748 B1 | 4/2002 | Yudovsky et al. |
| 6,376,386 B1 | 4/2002 | Oshima |
| 6,379,575 B1 | 4/2002 | Yin et al. |
| 6,383,896 B1 | 5/2002 | Kirimura et al. |
| 6,383,951 B1 | 5/2002 | Li |
| 6,387,207 B1 | 5/2002 | Janakiraman et al. |
| 6,391,753 B1 | 5/2002 | Yu |
| 6,395,150 B1 | 5/2002 | Van Cleemput et al. |
| 6,403,491 B1 | 6/2002 | Liu et al. |
| 6,415,736 B1 | 7/2002 | Hao et al. |
| 6,416,647 B1 | 7/2002 | Dordi et al. |

(56) References Cited

U.S. PATENT DOCUMENTS

| | | | |
|---|---|---|---|
| 6,418,874 B1 | 7/2002 | Cox et al. |
| 6,423,284 B1 | 7/2002 | Arno |
| 6,427,623 B2 | 8/2002 | Ko |
| 6,429,465 B1 | 8/2002 | Yagi et al. |
| 6,432,819 B1 | 8/2002 | Pavate et al. |
| 6,432,831 B2 | 8/2002 | Dhindsa et al. |
| 6,436,193 B1 | 8/2002 | Kasai et al. |
| 6,436,816 B1 | 8/2002 | Lee et al. |
| 6,440,863 B1 | 8/2002 | Tsai et al. |
| 6,441,492 B1 | 8/2002 | Cunningham |
| 6,446,572 B1 | 9/2002 | Brcka |
| 6,447,636 B1 | 9/2002 | Qian et al. |
| 6,448,537 B1 | 9/2002 | Nering |
| 6,458,718 B1 | 10/2002 | Todd |
| 6,461,974 B1 | 10/2002 | Ni et al. |
| 6,462,371 B1 | 10/2002 | Weimer et al. |
| 6,462,372 B1 | 10/2002 | Xia et al. |
| 6,465,051 B1 | 10/2002 | Sahin et al. |
| 6,465,350 B1 | 10/2002 | Taylor et al. |
| 6,465,366 B1 | 10/2002 | Nemani et al. |
| 6,477,980 B1 | 11/2002 | White et al. |
| 6,479,373 B2 | 11/2002 | Dreybrodt et al. |
| 6,488,984 B1 | 12/2002 | Wada et al. |
| 6,494,959 B1 | 12/2002 | Samoilov et al. |
| 6,499,425 B1 | 12/2002 | Sandhu et al. |
| 6,500,728 B1 | 12/2002 | Wang |
| 6,503,843 B1 | 1/2003 | Xia et al. |
| 6,506,291 B2 | 1/2003 | Tsai et al. |
| 6,509,283 B1 | 1/2003 | Thomas |
| 6,509,623 B2 | 1/2003 | Zhao |
| 6,516,815 B1 | 2/2003 | Stevens et al. |
| 6,518,548 B2 | 2/2003 | Sugaya et al. |
| 6,527,968 B1 | 3/2003 | Wang et al. |
| 6,528,409 B1 | 3/2003 | Lopatin et al. |
| 6,528,751 B1 | 3/2003 | Hoffman et al. |
| 6,531,069 B1 | 3/2003 | Srivastava et al. |
| 6,537,707 B1 | 3/2003 | Lee |
| 6,537,733 B2 | 3/2003 | Campana et al. |
| 6,541,397 B1 | 4/2003 | Bencher |
| 6,541,671 B1 | 4/2003 | Martinez et al. |
| 6,544,340 B2 | 4/2003 | Yudovsky |
| 6,547,977 B1 | 4/2003 | Yan et al. |
| 6,551,924 B1 | 4/2003 | Dalton et al. |
| 6,558,564 B1 | 5/2003 | Loewenhardt |
| 6,565,661 B1 | 5/2003 | Nguyen |
| 6,565,729 B2 | 5/2003 | Chen et al. |
| 6,569,773 B1 | 5/2003 | Gellrich et al. |
| 6,572,937 B2 | 6/2003 | Hakovirta et al. |
| 6,573,030 B1 | 6/2003 | Fairbairn et al. |
| 6,573,606 B2 | 6/2003 | Sambucetti et al. |
| 6,585,851 B1 | 7/2003 | Ohmi et al. |
| 6,586,163 B1 | 7/2003 | Okabe et al. |
| 6,596,599 B1 | 7/2003 | Guo |
| 6,596,654 B1 | 7/2003 | Bayman et al. |
| 6,602,434 B1 | 8/2003 | Hung et al. |
| 6,602,806 B1 | 8/2003 | Xia et al. |
| 6,603,269 B1 | 8/2003 | Vo et al. |
| 6,605,874 B2 | 8/2003 | Leu et al. |
| 6,616,967 B1 | 9/2003 | Test |
| 6,627,532 B1 | 9/2003 | Gaillard et al. |
| 6,635,575 B1 | 10/2003 | Xia et al. |
| 6,635,578 B1 | 10/2003 | Xu et al. |
| 6,638,810 B2 | 10/2003 | Bakli et al. |
| 6,645,301 B2 | 11/2003 | Sainty et al. |
| 6,645,550 B1 | 11/2003 | Cheung et al. |
| 6,656,831 B1 | 12/2003 | Lee et al. |
| 6,656,837 B2 | 12/2003 | Xu et al. |
| 6,656,848 B1 | 12/2003 | Scanlan et al. |
| 6,663,715 B1 | 12/2003 | Yuda et al. |
| 6,673,200 B1 | 1/2004 | Gu et al. |
| 6,677,242 B1 | 1/2004 | Liu et al. |
| 6,679,981 B1 | 1/2004 | Pan et al. |
| 6,688,375 B1 | 2/2004 | Turner |
| 6,713,356 B1 | 3/2004 | Skotnicki et al. |
| 6,713,835 B1 | 3/2004 | Horak et al. |
| 6,717,189 B2 | 4/2004 | Inoue et al. |
| 6,720,213 B1 | 4/2004 | Gambino et al. |
| 6,736,147 B2 | 5/2004 | Satoh et al. |
| 6,736,987 B1 | 5/2004 | Cho |
| 6,740,247 B1 | 5/2004 | Han et al. |
| 6,740,585 B2 | 5/2004 | Yoon et al. |
| 6,740,977 B2 | 5/2004 | Ahn et al. |
| 6,743,473 B1 | 6/2004 | Parkhe et al. |
| 6,743,732 B1 | 6/2004 | Lin et al. |
| 6,756,235 B1 | 6/2004 | Liu et al. |
| 6,759,261 B2 | 7/2004 | Shimokohbe et al. |
| 6,762,127 B2 | 7/2004 | Boiteux et al. |
| 6,762,435 B2 | 7/2004 | Towle |
| 6,764,958 B1 | 7/2004 | Nemani et al. |
| 6,765,273 B1 | 7/2004 | Chau et al. |
| 6,767,834 B2 | 7/2004 | Chung et al. |
| 6,768,079 B2 | 7/2004 | Kosakai |
| 6,770,166 B1 | 8/2004 | Fisher |
| 6,772,827 B2 | 8/2004 | Keller et al. |
| 6,792,889 B2 | 9/2004 | Nakano et al. |
| 6,794,290 B1 | 9/2004 | Papasouliotis et al. |
| 6,794,311 B2 | 9/2004 | Huang et al. |
| 6,796,314 B1 | 9/2004 | Graff et al. |
| 6,797,189 B2 | 9/2004 | Hung et al. |
| 6,800,336 B1 | 10/2004 | Fornsel et al. |
| 6,800,830 B2 | 10/2004 | Mahawili |
| 6,802,944 B2 | 10/2004 | Ahmad et al. |
| 6,808,564 B2 | 10/2004 | Dietze |
| 6,808,747 B1 | 10/2004 | Shih et al. |
| 6,808,748 B2 | 10/2004 | Kapoor et al. |
| 6,815,633 B1 | 11/2004 | Chen et al. |
| 6,821,571 B2 | 11/2004 | Huang |
| 6,823,589 B2 | 11/2004 | White et al. |
| 6,828,241 B2 | 12/2004 | Kholodenko et al. |
| 6,830,624 B2 | 12/2004 | Janakiraman et al. |
| 6,835,995 B2 | 12/2004 | Li |
| 6,846,745 B1 | 1/2005 | Papasouliotis et al. |
| 6,849,854 B2 | 2/2005 | Sainty |
| 6,852,550 B2 | 2/2005 | Tuttle et al. |
| 6,852,584 B1 | 2/2005 | Chen et al. |
| 6,853,533 B2 | 2/2005 | Parkhe et al. |
| 6,858,153 B2 | 2/2005 | Bjorkman et al. |
| 6,861,097 B1 | 3/2005 | Goosey et al. |
| 6,861,332 B2 | 3/2005 | Park et al. |
| 6,869,880 B2 | 3/2005 | Krishnaraj et al. |
| 6,875,280 B2 | 4/2005 | Ikeda et al. |
| 6,878,206 B2 | 4/2005 | Tzu et al. |
| 6,879,981 B2 | 4/2005 | Rothschild et al. |
| 6,886,491 B2 | 5/2005 | Kim et al. |
| 6,892,669 B2 | 5/2005 | Xu et al. |
| 6,893,967 B1 | 5/2005 | Wright et al. |
| 6,897,532 B1 | 5/2005 | Schwarz et al. |
| 6,900,596 B2 | 5/2005 | Yang et al. |
| 6,903,511 B2 | 6/2005 | Chistyakov |
| 6,908,862 B2 | 6/2005 | Li et al. |
| 6,911,112 B2 | 6/2005 | An |
| 6,911,401 B2 | 6/2005 | Khandan et al. |
| 6,916,399 B1 | 7/2005 | Rozenzon et al. |
| 6,921,556 B2 | 7/2005 | Shimizu et al. |
| 6,924,191 B2 | 8/2005 | Liu et al. |
| 6,930,047 B2 | 8/2005 | Yamazaki |
| 6,935,269 B2 | 8/2005 | Lee et al. |
| 6,942,753 B2 | 9/2005 | Choi et al. |
| 6,946,033 B2 | 9/2005 | Tsuei et al. |
| 6,951,821 B2 | 10/2005 | Hamelin et al. |
| 6,958,175 B2 | 10/2005 | Sakamoto et al. |
| 6,958,286 B2 | 10/2005 | Chen et al. |
| 6,969,619 B1 * | 11/2005 | Winniczek ............ G01N 21/73 257/E21.218 |
| 6,972,840 B1 | 12/2005 | Gu et al. |
| 6,995,073 B2 | 2/2006 | Liou |
| 7,017,269 B2 | 3/2006 | White et al. |
| 7,018,941 B2 | 3/2006 | Cui et al. |
| 7,030,034 B2 | 4/2006 | Fucsko et al. |
| 7,049,200 B2 | 5/2006 | Arghavani et al. |
| 7,052,553 B1 | 5/2006 | Shih et al. |
| 7,071,532 B2 | 7/2006 | Geffken et al. |
| 7,084,070 B1 | 8/2006 | Lee et al. |
| 7,115,525 B2 | 10/2006 | Abatchev et al. |

(56) References Cited

U.S. PATENT DOCUMENTS

| | | |
|---|---|---|
| 7,122,949 B2 | 10/2006 | Strikovski |
| 7,138,767 B2 | 11/2006 | Chen et al. |
| 7,145,725 B2 | 12/2006 | Hasel et al. |
| 7,148,155 B1 | 12/2006 | Tarafdar et al. |
| 7,166,233 B2 | 1/2007 | Johnson et al. |
| 7,183,214 B2 | 2/2007 | Nam et al. |
| 7,196,342 B2 | 3/2007 | Ershov et al. |
| 7,226,805 B2 | 6/2007 | Hallin et al. |
| 7,235,137 B2 | 6/2007 | Kitayama et al. |
| 7,244,474 B2 | 7/2007 | Hanawa et al. |
| 7,252,011 B2 | 8/2007 | Traverso |
| 7,252,716 B2 | 8/2007 | Kim et al. |
| 7,253,123 B2 | 8/2007 | Arghavani et al. |
| 7,256,370 B2 | 8/2007 | Guiver |
| 7,274,004 B2 | 9/2007 | Benjamin et al. |
| 7,288,482 B2 | 10/2007 | Panda et al. |
| 7,291,360 B2 | 11/2007 | Hanawa et al. |
| 7,297,894 B1 | 11/2007 | Tsukamoto |
| 7,316,761 B2 | 1/2008 | Doan et al. |
| 7,329,608 B2 | 2/2008 | Babayan et al. |
| 7,341,633 B2 | 3/2008 | Lubomirsky et al. |
| 7,344,912 B1 | 3/2008 | Okoroanyanwu |
| 7,358,192 B2 | 4/2008 | Merry et al. |
| 7,361,865 B2 | 4/2008 | Maki et al. |
| 7,364,956 B2 | 4/2008 | Saito |
| 7,365,016 B2 | 4/2008 | Ouellet et al. |
| 7,396,480 B2 | 7/2008 | Kao et al. |
| 7,396,773 B1 | 7/2008 | Blosse et al. |
| 7,416,989 B1 | 8/2008 | Liu et al. |
| 7,465,358 B2 | 12/2008 | Weidman et al. |
| 7,465,953 B1 | 12/2008 | Koh et al. |
| 7,468,319 B2 | 12/2008 | Lee |
| 7,479,303 B2 | 1/2009 | Byun et al. |
| 7,484,473 B2 | 2/2009 | Keller et al. |
| 7,488,688 B2 | 2/2009 | Chung et al. |
| 7,494,545 B2 | 2/2009 | Lam et al. |
| 7,500,445 B2 | 3/2009 | Zhao et al. |
| 7,504,040 B2 | 3/2009 | Lijima et al. |
| 7,513,214 B2 | 4/2009 | Okumura et al. |
| 7,520,957 B2 | 4/2009 | Kao et al. |
| 7,553,756 B2 | 6/2009 | Hayashi et al. |
| 7,575,007 B2 | 8/2009 | Tang et al. |
| 7,581,511 B2 | 9/2009 | Mardian et al. |
| 7,604,708 B2 | 10/2009 | Wood et al. |
| 7,611,980 B2 | 11/2009 | Wells |
| 7,628,897 B2 | 12/2009 | Mungekar et al. |
| 7,658,799 B2 | 2/2010 | Ishikawa et al. |
| 7,682,518 B2 | 3/2010 | Chandrachood et al. |
| 7,695,590 B2 | 4/2010 | Hanawa et al. |
| 7,708,859 B2 | 5/2010 | Huang et al. |
| 7,722,925 B2 | 5/2010 | White et al. |
| 7,723,221 B2 | 5/2010 | Hayashi |
| 7,749,326 B2 | 7/2010 | Kim et al. |
| 7,780,790 B2 | 8/2010 | Nogami |
| 7,785,672 B2 | 8/2010 | Choi et al. |
| 7,790,634 B2 | 9/2010 | Munro et al. |
| 7,806,077 B2 | 10/2010 | Lee et al. |
| 7,806,078 B2 | 10/2010 | Yoshida |
| 7,807,578 B2 | 10/2010 | Bencher et al. |
| 7,825,038 B2 | 11/2010 | Ingle et al. |
| 7,837,828 B2 | 11/2010 | Ikeda et al. |
| 7,845,309 B2 | 12/2010 | Condrashoff et al. |
| 7,867,926 B2 | 1/2011 | Satoh et al. |
| 7,906,818 B2 | 3/2011 | Pekny |
| 7,915,139 B1 | 3/2011 | Lang et al. |
| 7,922,863 B2 | 4/2011 | Ripley |
| 7,932,181 B2 | 4/2011 | Singh et al. |
| 7,939,422 B2 | 5/2011 | Ingle et al. |
| 7,968,441 B2 | 6/2011 | Xu |
| 7,976,631 B2 | 7/2011 | Burrows |
| 7,977,249 B1 | 7/2011 | Liu |
| 7,981,806 B2 | 7/2011 | Jung |
| 7,989,365 B2 | 8/2011 | Park et al. |
| 8,008,166 B2 | 8/2011 | Sanchez et al. |
| 8,048,811 B2 | 11/2011 | Feustel et al. |
| 8,058,179 B1 | 11/2011 | Draeger et al. |
| 8,071,482 B2 | 12/2011 | Kawada |
| 8,074,599 B2 | 12/2011 | Choi et al. |
| 8,076,198 B2 | 12/2011 | Lee et al. |
| 8,083,853 B2 | 12/2011 | Choi et al. |
| 8,114,245 B2 | 2/2012 | Ohmi et al. |
| 8,119,530 B2 | 2/2012 | Hori et al. |
| 8,133,349 B1 | 3/2012 | Panagopoulos |
| 8,173,228 B2 | 5/2012 | Choi et al. |
| 8,183,134 B2 | 5/2012 | Wu |
| 8,187,486 B1 | 5/2012 | Liu et al. |
| 8,199,454 B2 | 6/2012 | Koyama et al. |
| 8,211,808 B2 | 7/2012 | Sapre et al. |
| 8,216,486 B2 | 7/2012 | Dhindsa |
| 8,222,128 B2 | 7/2012 | Sasaki et al. |
| 8,252,194 B2 | 8/2012 | Kiehlbauch et al. |
| 8,272,346 B2 | 9/2012 | Bettencourt et al. |
| 8,295,089 B2 | 10/2012 | Jeong et al. |
| 8,298,627 B2 | 10/2012 | Minami et al. |
| 8,298,959 B2 | 10/2012 | Cheshire |
| 8,309,440 B2 | 11/2012 | Sanchez et al. |
| 8,312,839 B2 | 11/2012 | Baek |
| 8,313,610 B2 | 11/2012 | Dhindsa |
| 8,328,939 B2 | 12/2012 | Choi et al. |
| 8,329,262 B2 | 12/2012 | Miller et al. |
| 8,336,188 B2 | 12/2012 | Monteen |
| 8,343,306 B2 | 1/2013 | Tanaka et al. |
| 8,357,435 B2 | 1/2013 | Lubomirsky |
| 8,361,892 B2 | 1/2013 | Tam et al. |
| 8,368,308 B2 | 2/2013 | Banna et al. |
| 8,390,980 B2 | 3/2013 | Sansoni et al. |
| 8,427,067 B2 | 4/2013 | Espiau et al. |
| 8,435,902 B2 | 5/2013 | Tang et al. |
| 8,440,523 B1 | 5/2013 | Guillorn et al. |
| 8,466,073 B2 | 6/2013 | Wang et al. |
| 8,475,674 B2 | 7/2013 | Thadani et al. |
| 8,480,850 B2 | 7/2013 | Tyler et al. |
| 8,491,805 B2 | 7/2013 | Kushibiki et al. |
| 8,501,629 B2 | 8/2013 | Tang et al. |
| 8,506,713 B2 | 8/2013 | Takagi |
| 8,512,509 B2 | 8/2013 | Bera et al. |
| 8,528,889 B2 | 9/2013 | Sansoni et al. |
| 8,540,844 B2 | 9/2013 | Hudson et al. |
| 8,551,891 B2 | 10/2013 | Liang |
| 8,573,152 B2 | 11/2013 | De La Llera |
| 8,622,021 B2 | 1/2014 | Taylor et al. |
| 8,623,471 B2 | 1/2014 | Tyler et al. |
| 8,633,423 B2 | 1/2014 | Lin et al. |
| 8,642,481 B2 | 2/2014 | Wang et al. |
| 8,652,298 B2 | 2/2014 | Dhindsa et al. |
| 8,668,836 B2 | 3/2014 | Mizukami et al. |
| 8,679,982 B2 | 3/2014 | Wang et al. |
| 8,679,983 B2 | 3/2014 | Wang et al. |
| 8,691,023 B2 | 4/2014 | Bao et al. |
| 8,702,902 B2 | 4/2014 | Blom et al. |
| 8,741,778 B2 | 6/2014 | Yang et al. |
| 8,747,610 B2 | 6/2014 | Chen et al. |
| 8,747,680 B1 | 6/2014 | Deshpande |
| 8,748,322 B1 | 6/2014 | Fung et al. |
| 8,765,574 B2 | 7/2014 | Zhang et al. |
| 8,771,536 B2 | 7/2014 | Zhang et al. |
| 8,771,539 B2 | 7/2014 | Zhang et al. |
| 8,772,888 B2 | 7/2014 | Jung et al. |
| 8,778,079 B2 | 7/2014 | Begarney et al. |
| 8,801,952 B1 | 8/2014 | Wang et al. |
| 8,802,572 B2 | 8/2014 | Nemani et al. |
| 8,808,563 B2 | 8/2014 | Wang et al. |
| 8,815,720 B2 | 8/2014 | Godet et al. |
| 8,835,316 B2 | 9/2014 | Yin et al. |
| 8,846,163 B2 | 9/2014 | Kao et al. |
| 8,869,742 B2 | 10/2014 | Dhindsa |
| 8,871,651 B1 | 10/2014 | Choi et al. |
| 8,888,087 B2 | 11/2014 | Okabe et al. |
| 8,894,767 B2 | 11/2014 | Goradia et al. |
| 8,895,449 B1 | 11/2014 | Zhu et al. |
| 8,900,364 B2 | 12/2014 | Wright |
| 8,921,234 B2 | 12/2014 | Liu et al. |
| 8,927,390 B2 | 1/2015 | Sapre et al. |

(56) References Cited

U.S. PATENT DOCUMENTS

| | | | |
|---|---|---|---|
| 8,932,947 B1* | 1/2015 | Han | H01J 37/32082 257/E21.218 |
| 8,937,017 B2 | 1/2015 | Cheshire et al. | |
| 8,945,414 B1 | 2/2015 | Su et al. | |
| 8,946,665 B2 | 2/2015 | Shim et al. | |
| 8,946,828 B2 | 2/2015 | Sun et al. | |
| 8,951,429 B1 | 2/2015 | Liu et al. | |
| 8,956,980 B1 | 2/2015 | Chen et al. | |
| 8,969,212 B2 | 3/2015 | Ren et al. | |
| 8,970,114 B2 | 3/2015 | Busche et al. | |
| 8,980,005 B2 | 3/2015 | Carlson et al. | |
| 8,980,758 B1 | 3/2015 | Ling et al. | |
| 8,980,763 B2 | 3/2015 | Wang et al. | |
| 8,992,723 B2 | 3/2015 | Sorensen et al. | |
| 8,999,656 B2 | 4/2015 | Jirstrom et al. | |
| 8,999,839 B2 | 4/2015 | Su et al. | |
| 8,999,856 B2 | 4/2015 | Zhang et al. | |
| 9,012,302 B2 | 4/2015 | Sapre et al. | |
| 9,017,481 B1 | 4/2015 | Pettinger et al. | |
| 9,023,732 B2 | 5/2015 | Wang et al. | |
| 9,023,734 B2 | 5/2015 | Chen et al. | |
| 9,034,770 B2 | 5/2015 | Park et al. | |
| 9,039,911 B2 | 5/2015 | Hudson et al. | |
| 9,040,422 B2 | 5/2015 | Wang et al. | |
| 9,064,815 B2 | 6/2015 | Zhang et al. | |
| 9,064,816 B2 | 6/2015 | Kim et al. | |
| 9,068,265 B2 | 6/2015 | Lubomirsky et al. | |
| 9,072,158 B2 | 6/2015 | Ikeda et al. | |
| 9,093,371 B2 | 7/2015 | Wang et al. | |
| 9,093,389 B2 | 7/2015 | Nemani | |
| 9,093,390 B2 | 7/2015 | Wang et al. | |
| 9,111,877 B2 | 8/2015 | Chen et al. | |
| 9,111,907 B2 | 8/2015 | Kamineni | |
| 9,114,438 B2 | 8/2015 | Hoinkis et al. | |
| 9,117,855 B2 | 8/2015 | Cho et al. | |
| 9,132,436 B2 | 9/2015 | Liang et al. | |
| 9,136,273 B1 | 9/2015 | Purayath et al. | |
| 9,144,147 B2 | 9/2015 | Yang et al. | |
| 9,153,442 B2 | 10/2015 | Wang et al. | |
| 9,159,606 B1 | 10/2015 | Purayath et al. | |
| 9,165,783 B2 | 10/2015 | Nemani et al. | |
| 9,165,786 B1 | 10/2015 | Purayath et al. | |
| 9,184,055 B2 | 11/2015 | Wang et al. | |
| 9,190,290 B2 | 11/2015 | Xue et al. | |
| 9,190,293 B2 | 11/2015 | Wang et al. | |
| 9,190,302 B2 | 11/2015 | Ni | |
| 9,202,708 B1 | 12/2015 | Chen et al. | |
| 9,209,012 B2 | 12/2015 | Chen et al. | |
| 9,236,265 B2 | 1/2016 | Korolik et al. | |
| 9,236,266 B2 | 1/2016 | Zhang et al. | |
| 9,240,315 B1 | 1/2016 | Hsieh et al. | |
| 9,245,762 B2 | 1/2016 | Zhang et al. | |
| 9,263,278 B2 | 2/2016 | Purayath et al. | |
| 9,269,590 B2 | 2/2016 | Luere et al. | |
| 9,275,834 B1 | 3/2016 | Park et al. | |
| 9,281,384 B2 | 3/2016 | Takeguchi | |
| 9,287,095 B2 | 3/2016 | Nguyen et al. | |
| 9,287,134 B2 | 3/2016 | Wang et al. | |
| 9,293,568 B2 | 3/2016 | Ko | |
| 9,299,537 B2 | 3/2016 | Kobayashi et al. | |
| 9,299,538 B2 | 3/2016 | Kobayashi et al. | |
| 9,299,575 B2 | 3/2016 | Park et al. | |
| 9,299,582 B2 | 3/2016 | Ingle et al. | |
| 9,299,583 B1 | 3/2016 | Wang et al. | |
| 9,309,598 B2 | 4/2016 | Wang et al. | |
| 9,324,576 B2 | 4/2016 | Zhang et al. | |
| 9,343,272 B1 | 5/2016 | Pandit et al. | |
| 9,343,327 B2 | 5/2016 | Zhange et al. | |
| 9,349,605 B1 | 5/2016 | Xu et al. | |
| 9,355,856 B2 | 5/2016 | Wang et al. | |
| 9,355,862 B2 | 5/2016 | Pandit et al. | |
| 9,355,863 B2 | 5/2016 | Chen et al. | |
| 9,355,922 B2 | 5/2016 | Park et al. | |
| 9,362,130 B2 | 6/2016 | Ingle et al. | |
| 9,362,163 B2 | 6/2016 | Danek et al. | |
| 9,368,364 B2 | 6/2016 | Park et al. | |
| 9,373,517 B2 | 6/2016 | Yang et al. | |
| 9,373,522 B1 | 6/2016 | Wang et al. | |
| 9,378,969 B2 | 6/2016 | Hsu et al. | |
| 9,378,978 B2 | 6/2016 | Purayath et al. | |
| 9,384,997 B2 | 7/2016 | Ren et al. | |
| 9,385,028 B2 | 7/2016 | Nemani et al. | |
| 9,390,937 B2 | 7/2016 | Chen et al. | |
| 9,396,961 B2 | 7/2016 | Arghavani et al. | |
| 9,396,989 B2 | 7/2016 | Purayath et al. | |
| 9,406,523 B2 | 8/2016 | Chen et al. | |
| 9,412,608 B2 | 8/2016 | Wang et al. | |
| 9,412,752 B1 | 8/2016 | Yeh et al. | |
| 9,418,858 B2 | 8/2016 | Wang et al. | |
| 9,425,041 B2 | 8/2016 | Berry et al. | |
| 9,425,058 B2 | 8/2016 | Kim et al. | |
| 9,431,268 B2 | 8/2016 | Lill et al. | |
| 9,431,414 B2 | 8/2016 | Jang et al. | |
| 9,343,358 B1 | 9/2016 | Montgomery | |
| 9,437,451 B2 | 9/2016 | Chen et al. | |
| 9,443,749 B2 | 9/2016 | Smith | |
| 9,449,845 B2 | 9/2016 | Liu et al. | |
| 9,449,846 B2 | 9/2016 | Liu et al. | |
| 9,449,850 B2 | 9/2016 | Wang et al. | |
| 9,460,959 B1 | 10/2016 | Xie et al. | |
| 9,466,469 B2 | 10/2016 | Khaja | |
| 9,472,412 B2 | 10/2016 | Zhang et al. | |
| 9,472,417 B2 | 10/2016 | Ingle et al. | |
| 9,478,432 B2 | 10/2016 | Chen et al. | |
| 9,478,433 B1 | 10/2016 | Zhou et al. | |
| 9,478,434 B2 | 10/2016 | Wang et al. | |
| 9,493,879 B2 | 11/2016 | Hoinkis et al. | |
| 9,496,167 B2 | 11/2016 | Purayath et al. | |
| 9,499,898 B2 | 11/2016 | Nguyen et al. | |
| 9,502,258 B2 | 11/2016 | Xue et al. | |
| 9,508,529 B2 | 11/2016 | Valcore et al. | |
| 9,520,303 B2 | 12/2016 | Wang et al. | |
| 9,543,163 B2 | 1/2017 | Ling et al. | |
| 9,564,296 B2 | 2/2017 | Kobayashi et al. | |
| 9,564,338 B1 | 2/2017 | Zhang et al. | |
| 9,576,788 B2 | 2/2017 | Liu et al. | |
| 9,576,809 B2 | 2/2017 | Korolik et al. | |
| 9,607,856 B2 | 3/2017 | Wang et al. | |
| 9,613,822 B2 | 4/2017 | Chen et al. | |
| 9,659,753 B2 | 5/2017 | Cho et al. | |
| 9,659,791 B2 | 5/2017 | Wang et al. | |
| 9,659,792 B2 | 5/2017 | Wang et al. | |
| 9,666,449 B2 | 5/2017 | Koval et al. | |
| 9,691,645 B2 | 6/2017 | Benjaminson et al. | |
| 9,704,723 B2 | 7/2017 | Wang et al. | |
| 9,711,366 B2 | 7/2017 | Ingle et al. | |
| 9,721,789 B1 | 8/2017 | Yang et al. | |
| 9,728,437 B2 | 8/2017 | Tran et al. | |
| 9,741,593 B2 | 8/2017 | Benjaminson et al. | |
| 9,768,034 B1 | 9/2017 | Xu et al. | |
| 9,773,648 B2 | 9/2017 | Cho et al. | |
| 9,773,695 B2 | 9/2017 | Purayath et al. | |
| 9,779,956 B1 | 10/2017 | Zhang et al. | |
| 9,812,462 B1 | 11/2017 | Pang et al. | |
| 9,822,009 B2 | 11/2017 | Kagaya et al. | |
| 9,831,097 B2 | 11/2017 | Ingle et al. | |
| 9,837,249 B2 | 12/2017 | Kobayashi et al. | |
| 9,837,284 B2 | 12/2017 | Chen et al. | |
| 9,837,286 B2 | 12/2017 | Yang et al. | |
| 9,842,744 B2 | 12/2017 | Zhang et al. | |
| 9,865,484 B1 | 1/2018 | Citla et al. | |
| 9,881,805 B2 | 1/2018 | Li et al. | |
| 9,885,117 B2 | 2/2018 | Lubomirsky et al. | |
| 9,887,096 B2 | 2/2018 | Park et al. | |
| 9,903,020 B2 | 2/2018 | Kim et al. | |
| 9,934,942 B1 | 4/2018 | Lubomirsky | |
| 9,941,097 B2 | 4/2018 | Yamazawa | |
| 9,947,549 B1 | 4/2018 | Park et al. | |
| 9,960,045 B1 | 5/2018 | Purayath et al. | |
| 9,966,240 B2 | 5/2018 | Park et al. | |
| 9,978,564 B2 | 5/2018 | Liang et al. | |
| 9,991,134 B2 | 6/2018 | Wang et al. | |
| 10,026,621 B2 | 7/2018 | Ko et al. | |
| 10,032,606 B2 | 7/2018 | Yang et al. | |

(56) References Cited

U.S. PATENT DOCUMENTS

| | | |
|---|---|---|
| 10,043,674 B1 | 8/2018 | Korolik et al. |
| 10,043,684 B1 | 8/2018 | Arnepalli et al. |
| 10,049,891 B1 | 8/2018 | Wang et al. |
| 10,062,578 B2 | 8/2018 | Zhang et al. |
| 10,062,579 B2 | 8/2018 | Chen et al. |
| 10,062,585 B2 | 8/2018 | Lubomirsky |
| 10,062,587 B2 | 8/2018 | Chen et al. |
| 10,083,830 B2 | 9/2018 | Seino et al. |
| 10,147,620 B2 | 12/2018 | Benjaminson et al. |
| 10,147,736 B2 | 12/2018 | Linuma |
| 10,269,541 B2 | 4/2019 | Stowell et al. |
| 2001/0003014 A1 | 6/2001 | Yuda |
| 2001/0006093 A1 | 7/2001 | Tabuchi |
| 2001/0008803 A1 | 7/2001 | Takamatsu et al. |
| 2001/0015175 A1 | 8/2001 | Masuda et al. |
| 2001/0015261 A1 | 8/2001 | Kobayashi et al. |
| 2001/0023741 A1 | 9/2001 | Collison et al. |
| 2001/0028093 A1 | 10/2001 | Yamazaki et al. |
| 2001/0028922 A1 | 10/2001 | Sandhu |
| 2001/0029891 A1 | 10/2001 | Oh et al. |
| 2001/0030366 A1 | 10/2001 | Nakano et al. |
| 2001/0034106 A1 | 10/2001 | Moise et al. |
| 2001/0034121 A1 | 10/2001 | Fu et al. |
| 2001/0035124 A1 | 11/2001 | Okayama et al. |
| 2001/0036706 A1 | 11/2001 | Kitamura |
| 2001/0037856 A1 | 11/2001 | Park |
| 2001/0037941 A1 | 11/2001 | Thompson |
| 2001/0039921 A1 | 11/2001 | Rolfson et al. |
| 2001/0042512 A1 | 11/2001 | Xu et al. |
| 2001/0047760 A1 | 12/2001 | Moslehi |
| 2001/0053585 A1 | 12/2001 | Kikuchi et al. |
| 2001/0053610 A1 | 12/2001 | Athavale |
| 2001/0054381 A1 | 12/2001 | Umotoy et al. |
| 2001/0054387 A1 | 12/2001 | Frankel et al. |
| 2002/0000202 A1 | 1/2002 | Yuda et al. |
| 2002/0001778 A1 | 1/2002 | Latchford et al. |
| 2002/0009560 A1 | 1/2002 | Ozono |
| 2002/0009885 A1 | 1/2002 | Brankner et al. |
| 2002/0011210 A1 | 1/2002 | Satoh et al. |
| 2002/0011214 A1 | 1/2002 | Kamarehi et al. |
| 2002/0016080 A1 | 2/2002 | Khan et al. |
| 2002/0016085 A1 | 2/2002 | Huang et al. |
| 2002/0023899 A1 | 2/2002 | Khater et al. |
| 2002/0028582 A1 | 3/2002 | Nallan et al. |
| 2002/0028585 A1 | 3/2002 | Chung et al. |
| 2002/0029747 A1 | 3/2002 | Powell et al. |
| 2002/0033233 A1 | 3/2002 | Savas |
| 2002/0036143 A1 | 3/2002 | Segawa et al. |
| 2002/0040764 A1 | 4/2002 | Kwan et al. |
| 2002/0040766 A1 | 4/2002 | Takahashi |
| 2002/0043690 A1 | 4/2002 | Doyle et al. |
| 2002/0045966 A1 | 4/2002 | Lee et al. |
| 2002/0054962 A1 | 5/2002 | Huang |
| 2002/0062954 A1 | 5/2002 | Getchel et al. |
| 2002/0069820 A1 | 6/2002 | Yudovsky |
| 2002/0070414 A1 | 6/2002 | Drescher et al. |
| 2002/0073925 A1 | 6/2002 | Noble et al. |
| 2002/0074573 A1 | 6/2002 | Takeuchi et al. |
| 2002/0075624 A1 | 6/2002 | Wang et al. |
| 2002/0086501 A1 | 7/2002 | O'Donnell et al. |
| 2002/0090781 A1 | 7/2002 | Skotnicki et al. |
| 2002/0090835 A1 | 7/2002 | Chakravarti et al. |
| 2002/0094378 A1 | 7/2002 | O-Donnell |
| 2002/0094591 A1 | 7/2002 | Sill et al. |
| 2002/0096493 A1 | 7/2002 | Hattori |
| 2002/0098681 A1 | 7/2002 | Hu et al. |
| 2002/0106845 A1 | 8/2002 | Chao et al. |
| 2002/0112819 A1 | 8/2002 | Kamarehi et al. |
| 2002/0124867 A1 | 9/2002 | Kim et al. |
| 2002/0129769 A1 | 9/2002 | Kim et al. |
| 2002/0129902 A1 | 9/2002 | Babayan et al. |
| 2002/0144657 A1 | 10/2002 | Chiang et al. |
| 2002/0153808 A1 | 10/2002 | Skotnicki et al. |
| 2002/0164885 A1 | 11/2002 | Lill et al. |
| 2002/0170678 A1 | 11/2002 | Hayashi et al. |
| 2002/0177322 A1 | 11/2002 | Li et al. |
| 2002/0179248 A1 | 12/2002 | Kabansky et al. |
| 2002/0182878 A1 | 12/2002 | Hirose et al. |
| 2002/0187280 A1 | 12/2002 | Johnson et al. |
| 2002/0187655 A1 | 12/2002 | Tan et al. |
| 2002/0197823 A1 | 12/2002 | Yoo et al. |
| 2003/0000647 A1 | 1/2003 | Yudovsky et al. |
| 2003/0003757 A1 | 1/2003 | Naltan et al. |
| 2003/0007910 A1 | 1/2003 | Lazarovich et al. |
| 2003/0010645 A1 | 1/2003 | Ting et al. |
| 2003/0015515 A1 | 1/2003 | Ito et al. |
| 2003/0019428 A1 | 1/2003 | Ku et al. |
| 2003/0019580 A1 | 1/2003 | Strang |
| 2003/0026060 A1 | 2/2003 | Hiramatsu et al. |
| 2003/0029566 A1 | 2/2003 | Roth |
| 2003/0029567 A1 | 2/2003 | Dhindsa et al. |
| 2003/0029715 A1 | 2/2003 | Yu et al. |
| 2003/0031905 A1 | 2/2003 | Saito et al. |
| 2003/0032284 A1 | 2/2003 | Enomoto et al. |
| 2003/0038127 A1 | 2/2003 | Liu et al. |
| 2003/0038305 A1 | 2/2003 | Wasshuber |
| 2003/0054608 A1 | 3/2003 | Tseng et al. |
| 2003/0066482 A1 | 4/2003 | Pokharna et al. |
| 2003/0071035 A1 | 4/2003 | Brailove |
| 2003/0072639 A1 | 4/2003 | White et al. |
| 2003/0075808 A1 | 4/2003 | Inoue et al. |
| 2003/0077857 A1 | 4/2003 | Xia et al. |
| 2003/0077909 A1 | 4/2003 | Jiwari |
| 2003/0079686 A1 | 5/2003 | Chen et al. |
| 2003/0087488 A1 | 5/2003 | Fink |
| 2003/0087531 A1 | 5/2003 | Kang et al. |
| 2003/0091938 A1 | 5/2003 | Fairbairn et al. |
| 2003/0094134 A1 | 5/2003 | Minami et al. |
| 2003/0098125 A1 | 5/2003 | An |
| 2003/0109143 A1 | 6/2003 | Hsieh et al. |
| 2003/0116087 A1 | 6/2003 | Nguyen et al. |
| 2003/0116439 A1 | 6/2003 | Seo et al. |
| 2003/0121608 A1 | 7/2003 | Chen et al. |
| 2003/0121609 A1 | 7/2003 | Ohmi et al. |
| 2003/0124465 A1 | 7/2003 | Lee et al. |
| 2003/0124842 A1 | 7/2003 | Hytros et al. |
| 2003/0127049 A1 | 7/2003 | Han et al. |
| 2003/0127740 A1 | 7/2003 | Hsu et al. |
| 2003/0129106 A1 | 7/2003 | Sorensen et al. |
| 2003/0129827 A1 | 7/2003 | Lee et al. |
| 2003/0132319 A1 | 7/2003 | Hytros et al. |
| 2003/0136520 A1 | 7/2003 | Yudovsky et al. |
| 2003/0140844 A1 | 7/2003 | Maa et al. |
| 2003/0143328 A1 | 7/2003 | Chen et al. |
| 2003/0148035 A1 | 8/2003 | Lingampalli |
| 2003/0150530 A1 | 8/2003 | Lin et al. |
| 2003/0152691 A1 | 8/2003 | Baude |
| 2003/0159307 A1 | 8/2003 | Sago et al. |
| 2003/0164226 A1 | 9/2003 | Kanno et al. |
| 2003/0168439 A1 | 9/2003 | Kanno et al. |
| 2003/0170945 A1 | 9/2003 | Igeta et al. |
| 2003/0173333 A1 | 9/2003 | Wang et al. |
| 2003/0173347 A1 | 9/2003 | Guiver |
| 2003/0173675 A1 | 9/2003 | Watanabe |
| 2003/0181040 A1 | 9/2003 | Ivanov et al. |
| 2003/0183244 A1 | 10/2003 | Rossman |
| 2003/0190426 A1 | 10/2003 | Padhi et al. |
| 2003/0196760 A1 | 10/2003 | Tyler et al. |
| 2003/0199170 A1 | 10/2003 | Li |
| 2003/0200929 A1 | 10/2003 | Otsuki |
| 2003/0205329 A1 | 11/2003 | Gujer et al. |
| 2003/0205479 A1 | 11/2003 | Lin et al. |
| 2003/0209323 A1 | 11/2003 | Yokogaki |
| 2003/0215570 A1 | 11/2003 | Seutter et al. |
| 2003/0215963 A1 | 11/2003 | AmRhein et al. |
| 2003/0216044 A1 | 11/2003 | Lin et al. |
| 2003/0221780 A1 | 12/2003 | Lei et al. |
| 2003/0224217 A1 | 12/2003 | Byun et al. |
| 2003/0224617 A1 | 12/2003 | Baek et al. |
| 2003/0230385 A1 | 12/2003 | Bach et al. |
| 2004/0002221 A1 | 1/2004 | O'Donnell et al. |
| 2004/0003828 A1 | 1/2004 | Jackson |
| 2004/0005726 A1 | 1/2004 | Huang |
| 2004/0018304 A1 | 1/2004 | Chung et al. |

(56) References Cited

U.S. PATENT DOCUMENTS

| | | |
|---|---|---|
| 2004/0020801 A1 | 2/2004 | Solling |
| 2004/0026371 A1 | 2/2004 | Nguyen et al. |
| 2004/0033678 A1 | 2/2004 | Arghavani et al. |
| 2004/0033684 A1 | 2/2004 | Li |
| 2004/0050328 A1 | 3/2004 | Kumagai et al. |
| 2004/0058070 A1 | 3/2004 | Takeuchi et al. |
| 2004/0058293 A1 | 3/2004 | Nguyen et al. |
| 2004/0060514 A1 | 4/2004 | Janakiraman et al. |
| 2004/0061447 A1 | 4/2004 | Saigusa et al. |
| 2004/0069225 A1 | 4/2004 | Fairbairn et al. |
| 2004/0070346 A1 | 4/2004 | Choi |
| 2004/0072446 A1 | 4/2004 | Liu et al. |
| 2004/0076529 A1 | 4/2004 | Gnauck et al. |
| 2004/0083967 A1 | 5/2004 | Yuda et al. |
| 2004/0087139 A1 | 5/2004 | Yeh et al. |
| 2004/0092063 A1 | 5/2004 | Okumura |
| 2004/0099285 A1 | 5/2004 | Wange et al. |
| 2004/0099378 A1 | 5/2004 | Kim et al. |
| 2004/0101667 A1 | 5/2004 | O'Loughlin et al. |
| 2004/0103844 A1 | 6/2004 | Chou et al. |
| 2004/0107908 A1 | 6/2004 | Collins et al. |
| 2004/0108067 A1 | 6/2004 | Fischione et al. |
| 2004/0108068 A1 | 6/2004 | Senzaki et al. |
| 2004/0115876 A1 | 6/2004 | Goundar et al. |
| 2004/0115947 A1 | 6/2004 | Fink et al. |
| 2004/0124280 A1 | 7/2004 | Shih et al. |
| 2004/0129671 A1 | 7/2004 | Ji et al. |
| 2004/0137161 A1 | 7/2004 | Segawa et al. |
| 2004/0140053 A1 | 7/2004 | Srivastava et al. |
| 2004/0144311 A1 | 7/2004 | Chen et al. |
| 2004/0144490 A1 | 7/2004 | Zhao et al. |
| 2004/0147126 A1 | 7/2004 | Yamashita et al. |
| 2004/0149223 A1 | 8/2004 | Collison et al. |
| 2004/0149387 A1 | 8/2004 | Kim et al. |
| 2004/0149394 A1 | 8/2004 | Doan et al. |
| 2004/0152342 A1 | 8/2004 | Li |
| 2004/0154535 A1 | 8/2004 | Chen et al. |
| 2004/0157444 A1 | 8/2004 | Chiu |
| 2004/0161921 A1 | 8/2004 | Ryu |
| 2004/0163601 A1 | 8/2004 | Kadotani et al. |
| 2004/0175913 A1 | 9/2004 | Johnson et al. |
| 2004/0175929 A1 | 9/2004 | Schmitt et al. |
| 2004/0182315 A1 | 9/2004 | Laflamme et al. |
| 2004/0187787 A1 | 9/2004 | Dawson |
| 2004/0192032 A1 | 9/2004 | Ohmori et al. |
| 2004/0194799 A1 | 10/2004 | Kim et al. |
| 2004/0195208 A1 | 10/2004 | Pavel et al. |
| 2004/0195216 A1 | 10/2004 | Strang |
| 2004/0200499 A1 | 10/2004 | Harvey |
| 2004/0211357 A1 | 10/2004 | Gadgil et al. |
| 2004/0219723 A1 | 11/2004 | Peng et al. |
| 2004/0219737 A1 | 11/2004 | Quon |
| 2004/0219789 A1 | 11/2004 | Wood et al. |
| 2004/0221809 A1 | 11/2004 | Ohmi et al. |
| 2004/0231706 A1 | 11/2004 | Bhatnagar et al. |
| 2004/0237897 A1 | 12/2004 | Hanawa et al. |
| 2004/0238123 A1 | 12/2004 | Becknell et al. |
| 2004/0259367 A1 | 12/2004 | Constantine et al. |
| 2004/0263827 A1 | 12/2004 | Xu |
| 2005/0000430 A1 | 1/2005 | Jang et al. |
| 2005/0001276 A1 | 1/2005 | Gao et al. |
| 2005/0003676 A1 | 1/2005 | Ho et al. |
| 2005/0009340 A1 | 1/2005 | Saijo et al. |
| 2005/0009358 A1 | 1/2005 | Choi et al. |
| 2005/0026430 A1 | 2/2005 | Kim et al. |
| 2005/0026431 A1 | 2/2005 | Kazumi et al. |
| 2005/0035455 A1 | 2/2005 | Hu et al. |
| 2005/0039679 A1 | 2/2005 | Kleshock |
| 2005/0051094 A1 | 3/2005 | Schaepkens et al. |
| 2005/0054167 A1 | 3/2005 | Choi et al. |
| 2005/0056218 A1 | 3/2005 | Sun et al. |
| 2005/0073051 A1 | 4/2005 | Yamamoto et al. |
| 2005/0079706 A1 | 4/2005 | Kumar et al. |
| 2005/0087517 A1 | 4/2005 | Ott et al. |
| 2005/0090078 A1 | 4/2005 | Ishihara |
| 2005/0090120 A1 | 4/2005 | Hasegawa et al. |
| 2005/0098111 A1 | 5/2005 | Shimizu et al. |
| 2005/0103267 A1 | 5/2005 | Hur et al. |
| 2005/0105991 A1 | 5/2005 | Hofmeister et al. |
| 2005/0109279 A1 | 5/2005 | Suzuki |
| 2005/0112876 A1 | 5/2005 | Wu |
| 2005/0112901 A1 | 5/2005 | Ji et al. |
| 2005/0123690 A1 | 6/2005 | Derderian et al. |
| 2005/0133849 A1 | 6/2005 | Jeon et al. |
| 2005/0136188 A1 | 6/2005 | Chang |
| 2005/0145341 A1 | 7/2005 | Suzuki |
| 2005/0164479 A1 | 7/2005 | Perng et al. |
| 2005/0167394 A1 | 8/2005 | Liu et al. |
| 2005/0176258 A1 | 8/2005 | Hirose et al. |
| 2005/0178746 A1 | 8/2005 | Gorin |
| 2005/0181588 A1 | 8/2005 | Kim |
| 2005/0183666 A1 | 8/2005 | Tsuji et al. |
| 2005/0194094 A1 | 9/2005 | Yasaka |
| 2005/0196967 A1 | 9/2005 | Savas et al. |
| 2005/0199489 A1 | 9/2005 | Stevens et al. |
| 2005/0205110 A1 | 9/2005 | Kao et al. |
| 2005/0205862 A1 | 9/2005 | Koemtzopoulos et al. |
| 2005/0208215 A1 | 9/2005 | Eguchi et al. |
| 2005/0208217 A1 | 9/2005 | Shinriki et al. |
| 2005/0214477 A1 | 9/2005 | Hanawa et al. |
| 2005/0217582 A1 | 10/2005 | Kim et al. |
| 2005/0218507 A1 | 10/2005 | Kao et al. |
| 2005/0219786 A1 | 10/2005 | Brown et al. |
| 2005/0221552 A1 | 10/2005 | Kao et al. |
| 2005/0224181 A1 | 10/2005 | Merry et al. |
| 2005/0229848 A1 | 10/2005 | Shinriki et al. |
| 2005/0230350 A1 | 10/2005 | Kao et al. |
| 2005/0236694 A1 | 10/2005 | Wu et al. |
| 2005/0238807 A1 | 10/2005 | Lin et al. |
| 2005/0239282 A1 | 10/2005 | Chen et al. |
| 2005/0241763 A1 | 11/2005 | Huang et al. |
| 2005/0251990 A1 | 11/2005 | Choi et al. |
| 2005/0266622 A1 | 12/2005 | Arghavani et al. |
| 2005/0266650 A1 | 12/2005 | Ahn et al. |
| 2005/0266691 A1 | 12/2005 | Gu et al. |
| 2005/0269030 A1 | 12/2005 | Kent et al. |
| 2005/0274324 A1 | 12/2005 | Takahashi et al. |
| 2005/0279454 A1 | 12/2005 | Snijders |
| 2005/0283321 A1 | 12/2005 | Yue et al. |
| 2005/0287688 A1 | 12/2005 | Won et al. |
| 2005/0287755 A1 | 12/2005 | Bachmann |
| 2005/0287771 A1 | 12/2005 | Seamons et al. |
| 2006/0000802 A1 | 1/2006 | Kumar et al. |
| 2006/0000805 A1 | 1/2006 | Todorow et al. |
| 2006/0005856 A1 | 1/2006 | Sun et al. |
| 2006/0005930 A1 | 1/2006 | Ikeda et al. |
| 2006/0006057 A1 | 1/2006 | Laermer |
| 2006/0008676 A1 | 1/2006 | Ebata et al. |
| 2006/0011298 A1 | 1/2006 | Lim et al. |
| 2006/0011299 A1 | 1/2006 | Condrashoff et al. |
| 2006/0016783 A1 | 1/2006 | Wu et al. |
| 2006/0019456 A1 | 1/2006 | Bu et al. |
| 2006/0019477 A1 | 1/2006 | Hanawa et al. |
| 2006/0019486 A1 | 1/2006 | Yu et al. |
| 2006/0021574 A1 | 2/2006 | Armour et al. |
| 2006/0021701 A1 | 2/2006 | Tobe et al. |
| 2006/0021703 A1 | 2/2006 | Umotoy et al. |
| 2006/0024954 A1 | 2/2006 | Wu et al. |
| 2006/0024956 A1 | 2/2006 | Zhijian et al. |
| 2006/0033678 A1 | 2/2006 | Lubomirsky et al. |
| 2006/0040055 A1 | 2/2006 | Nguyen et al. |
| 2006/0043066 A1 | 3/2006 | Kamp |
| 2006/0046412 A1 | 3/2006 | Nguyen et al. |
| 2006/0046419 A1 | 3/2006 | Sandhu et al. |
| 2006/0046470 A1 | 3/2006 | Becknell |
| 2006/0051966 A1 | 3/2006 | Or et al. |
| 2006/0051968 A1 | 3/2006 | Joshi et al. |
| 2006/0054184 A1 | 3/2006 | Mozetic et al. |
| 2006/0054280 A1 | 3/2006 | Jang |
| 2006/0057828 A1 | 3/2006 | Omura et al. |
| 2006/0060942 A1 | 3/2006 | Minixhofer et al. |
| 2006/0065629 A1 | 3/2006 | Chen et al. |
| 2006/0073349 A1 | 4/2006 | Aihara et al. |
| 2006/0076108 A1 | 4/2006 | Holland et al. |

(56) References Cited

U.S. PATENT DOCUMENTS

| | | |
|---|---|---|
| 2006/0087644 A1 | 4/2006 | McMillin et al. |
| 2006/0090700 A1 | 5/2006 | Satoh et al. |
| 2006/0093756 A1 | 5/2006 | Rajagopalan et al. |
| 2006/0097397 A1 | 5/2006 | Russell et al. |
| 2006/0102076 A1 | 5/2006 | Smith et al. |
| 2006/0102587 A1 | 5/2006 | Kimura |
| 2006/0113038 A1 | 6/2006 | Gondhalekar et al. |
| 2006/0118178 A1 | 6/2006 | Desbiolles et al. |
| 2006/0118240 A1 | 6/2006 | Holber et al. |
| 2006/0121724 A1 | 6/2006 | Yue et al. |
| 2006/0124151 A1 | 6/2006 | Yamasaki et al. |
| 2006/0124242 A1 | 6/2006 | Kanarik et al. |
| 2006/0130971 A1 | 6/2006 | Chang et al. |
| 2006/0151115 A1 | 7/2006 | Kim et al. |
| 2006/0157449 A1 | 7/2006 | Takahashi et al. |
| 2006/0162661 A1 | 7/2006 | Jung et al. |
| 2006/0166107 A1 | 7/2006 | Chen et al. |
| 2006/0166515 A1 | 7/2006 | Karim et al. |
| 2006/0169327 A1 | 8/2006 | Shajii et al. |
| 2006/0169410 A1 | 8/2006 | Maeda et al. |
| 2006/0178008 A1 | 8/2006 | Yeh et al. |
| 2006/0183270 A1 | 8/2006 | Humpston |
| 2006/0185592 A1 | 8/2006 | Matsuura |
| 2006/0191479 A1 | 8/2006 | Mizukami et al. |
| 2006/0191637 A1 | 8/2006 | Zajac et al. |
| 2006/0207504 A1 | 9/2006 | Hasebe et al. |
| 2006/0207595 A1 | 9/2006 | Ohmi et al. |
| 2006/0207971 A1 | 9/2006 | Moriya et al. |
| 2006/0210713 A1 | 9/2006 | Brcka |
| 2006/0210723 A1 | 9/2006 | Ishizaka |
| 2006/0215347 A1 | 9/2006 | Wakabayashi et al. |
| 2006/0216878 A1 | 9/2006 | Lee |
| 2006/0219360 A1 | 10/2006 | Iwasaki |
| 2006/0222481 A1 | 10/2006 | Foree |
| 2006/0226121 A1 | 10/2006 | Aoi |
| 2006/0228889 A1 | 10/2006 | Edelberg et al. |
| 2006/0240661 A1 | 10/2006 | Annapragada et al. |
| 2006/0244107 A1 | 11/2006 | Sugihara |
| 2006/0245852 A1 | 11/2006 | Iwabuchi |
| 2006/0246217 A1 | 11/2006 | Weidman et al. |
| 2006/0251800 A1 | 11/2006 | Weidman et al. |
| 2006/0251801 A1 | 11/2006 | Weidman et al. |
| 2006/0252252 A1 | 11/2006 | Zhu et al. |
| 2006/0252265 A1 | 11/2006 | Jin et al. |
| 2006/0254716 A1 | 11/2006 | Mosden et al. |
| 2006/0260750 A1 | 11/2006 | Rueger |
| 2006/0261490 A1 | 11/2006 | Su et al. |
| 2006/0264043 A1 | 11/2006 | Stewart et al. |
| 2006/0266288 A1 | 11/2006 | Choi |
| 2006/0286774 A1 | 12/2006 | Singh et al. |
| 2006/0289384 A1* | 12/2006 | Pavel ............... H01J 37/32935 216/59 |
| 2006/0292846 A1 | 12/2006 | Pinto et al. |
| 2007/0022952 A1 | 2/2007 | Ritchie et al. |
| 2007/0025907 A1 | 2/2007 | Rezeq |
| 2007/0039548 A1 | 2/2007 | Johnson |
| 2007/0048977 A1 | 3/2007 | Lee et al. |
| 2007/0051471 A1 | 3/2007 | Kawaguchi et al. |
| 2007/0056925 A1 | 3/2007 | Liu et al. |
| 2007/0062453 A1 | 3/2007 | Ishikawa |
| 2007/0066084 A1 | 3/2007 | Wajda et al. |
| 2007/0071888 A1 | 3/2007 | Shanmugasundram et al. |
| 2007/0072408 A1 | 3/2007 | Enomoto et al. |
| 2007/0077737 A1 | 4/2007 | Kobayashi |
| 2007/0079758 A1 | 4/2007 | Holland et al. |
| 2007/0090325 A1 | 4/2007 | Hwang et al. |
| 2007/0099428 A1 | 5/2007 | Shamiryan et al. |
| 2007/0099431 A1 | 5/2007 | Li |
| 2007/0099438 A1 | 5/2007 | Ye et al. |
| 2007/0107750 A1 | 5/2007 | Sawin et al. |
| 2007/0108404 A1 | 5/2007 | Stewart et al. |
| 2007/0111519 A1 | 5/2007 | Lubomirsky et al. |
| 2007/0117396 A1 | 5/2007 | Wu et al. |
| 2007/0119370 A1 | 5/2007 | Ma et al. |
| 2007/0119371 A1 | 5/2007 | Ma et al. |
| 2007/0123051 A1 | 5/2007 | Arghavani et al. |
| 2007/0128864 A1 | 6/2007 | Ma |
| 2007/0131274 A1 | 6/2007 | Stollwerck et al. |
| 2007/0145023 A1 | 6/2007 | Holber et al. |
| 2007/0154838 A1 | 7/2007 | Lee |
| 2007/0163440 A1 | 7/2007 | Kim et al. |
| 2007/0175861 A1 | 8/2007 | Hwang et al. |
| 2007/0181057 A1 | 8/2007 | Lam et al. |
| 2007/0193515 A1 | 8/2007 | Jeon et al. |
| 2007/0197028 A1 | 8/2007 | Byun et al. |
| 2007/0207275 A1 | 9/2007 | Nowak et al. |
| 2007/0212288 A1 | 9/2007 | Holst |
| 2007/0221620 A1 | 9/2007 | Sakthivel et al. |
| 2007/0227554 A1 | 10/2007 | Satoh et al. |
| 2007/0231109 A1 | 10/2007 | Pak et al. |
| 2007/0232071 A1 | 10/2007 | Balseanu et al. |
| 2007/0235134 A1 | 10/2007 | Limuro |
| 2007/0235136 A1 | 10/2007 | Enomoto et al. |
| 2007/0238199 A1 | 10/2007 | Yamashita |
| 2007/0238321 A1 | 10/2007 | Futase et al. |
| 2007/0243685 A1 | 10/2007 | Jiang et al. |
| 2007/0243714 A1 | 10/2007 | Shin et al. |
| 2007/0254169 A1 | 11/2007 | Kamins et al. |
| 2007/0258186 A1 | 11/2007 | Matyushkin et al. |
| 2007/0259467 A1 | 11/2007 | Tweet et al. |
| 2007/0264820 A1 | 11/2007 | Liu |
| 2007/0266946 A1 | 11/2007 | Choi |
| 2007/0277734 A1 | 12/2007 | Lubomirsky et al. |
| 2007/0280816 A1 | 12/2007 | Kurita et al. |
| 2007/0281106 A1 | 12/2007 | Lubomirsky et al. |
| 2007/0284044 A1 | 12/2007 | Matsumoto et al. |
| 2007/0287292 A1 | 12/2007 | Li et al. |
| 2007/0296967 A1 | 12/2007 | Gupta et al. |
| 2008/0003836 A1 | 1/2008 | Nishimura et al. |
| 2008/0011424 A1 | 1/2008 | Yin et al. |
| 2008/0017104 A1 | 1/2008 | Matyushkin et al. |
| 2008/0020570 A1 | 1/2008 | Naik |
| 2008/0029032 A1 | 2/2008 | Sun et al. |
| 2008/0035608 A1 | 2/2008 | Thomas et al. |
| 2008/0044593 A1 | 2/2008 | Seo et al. |
| 2008/0044990 A1 | 2/2008 | Lee |
| 2008/0050538 A1 | 2/2008 | Hirata |
| 2008/0063810 A1 | 3/2008 | Park et al. |
| 2008/0075668 A1 | 3/2008 | Goldstein |
| 2008/0081483 A1 | 4/2008 | Wu |
| 2008/0085604 A1 | 4/2008 | Hoshino et al. |
| 2008/0099147 A1 | 5/2008 | Myo et al. |
| 2008/0099431 A1 | 5/2008 | Kumar et al. |
| 2008/0099876 A1 | 5/2008 | Seto |
| 2008/0100222 A1 | 5/2008 | Lewington et al. |
| 2008/0102570 A1 | 5/2008 | Fischer et al. |
| 2008/0102640 A1 | 5/2008 | Hassan et al. |
| 2008/0102646 A1 | 5/2008 | Kawaguchi et al. |
| 2008/0104782 A1 | 5/2008 | Hughes |
| 2008/0105555 A1 | 5/2008 | Iwazaki et al. |
| 2008/0115726 A1 | 5/2008 | Ingle et al. |
| 2008/0121970 A1 | 5/2008 | Aritome |
| 2008/0124937 A1 | 5/2008 | Xu et al. |
| 2008/0141941 A1 | 6/2008 | Augustino et al. |
| 2008/0142831 A1 | 6/2008 | Su |
| 2008/0153306 A1 | 6/2008 | Cho et al. |
| 2008/0156631 A1 | 7/2008 | Fair et al. |
| 2008/0156771 A1 | 7/2008 | Jeon et al. |
| 2008/0157225 A1 | 7/2008 | Datta et al. |
| 2008/0160210 A1 | 7/2008 | Yang et al. |
| 2008/0169588 A1 | 7/2008 | Shih et al. |
| 2008/0171407 A1 | 7/2008 | Nakabayashi et al. |
| 2008/0173906 A1 | 7/2008 | Zhu |
| 2008/0176412 A1 | 7/2008 | Komeda |
| 2008/0178797 A1 | 7/2008 | Fodor et al. |
| 2008/0178805 A1 | 7/2008 | Paterson et al. |
| 2008/0182381 A1 | 7/2008 | Kiyotoshi |
| 2008/0182382 A1 | 7/2008 | Ingle et al. |
| 2008/0182383 A1 | 7/2008 | Lee et al. |
| 2008/0193673 A1 | 8/2008 | Paterson et al. |
| 2008/0196666 A1 | 8/2008 | Toshima |
| 2008/0202688 A1 | 8/2008 | Wu et al. |
| 2008/0202892 A1 | 8/2008 | Smith et al. |
| 2008/0213496 A1 | 9/2008 | Sun et al. |

(56) References Cited

U.S. PATENT DOCUMENTS

| | | |
|---|---|---|
| 2008/0216901 A1 | 9/2008 | Chamberlain et al. |
| 2008/0216958 A1 | 9/2008 | Goto et al. |
| 2008/0230519 A1 | 9/2008 | Takahashi |
| 2008/0233709 A1 | 9/2008 | Conti et al. |
| 2008/0236751 A1 | 10/2008 | Aramaki et al. |
| 2008/0254635 A1 | 10/2008 | Benzel et al. |
| 2008/0261404 A1 | 10/2008 | Kozuka et al. |
| 2008/0264337 A1 | 10/2008 | Sano et al. |
| 2008/0268645 A1 | 10/2008 | Kao et al. |
| 2008/0292798 A1 | 11/2008 | Huh et al. |
| 2008/0293248 A1 | 11/2008 | Park et al. |
| 2008/0317965 A1 | 12/2008 | Son et al. |
| 2009/0000743 A1 | 1/2009 | Iizuka |
| 2009/0001480 A1 | 1/2009 | Cheng |
| 2009/0004849 A1 | 1/2009 | Eun |
| 2009/0004873 A1 | 1/2009 | Yang |
| 2009/0014127 A1 | 1/2009 | Shah et al. |
| 2009/0014323 A1 | 1/2009 | Yendler et al. |
| 2009/0014324 A1 | 1/2009 | Kawaguchi et al. |
| 2009/0017227 A1 | 1/2009 | Fu et al. |
| 2009/0022633 A1 | 1/2009 | Tomosue et al. |
| 2009/0036292 A1 | 2/2009 | Sun et al. |
| 2009/0045167 A1 | 2/2009 | Maruyama |
| 2009/0061640 A1 | 3/2009 | Wong et al. |
| 2009/0072401 A1 | 3/2009 | Arnold et al. |
| 2009/0081878 A1 | 3/2009 | Dhindsa |
| 2009/0084317 A1 | 4/2009 | Wu et al. |
| 2009/0087960 A1 | 4/2009 | Cho et al. |
| 2009/0087979 A1 | 4/2009 | Raghuram |
| 2009/0095221 A1 | 4/2009 | Tam et al. |
| 2009/0095222 A1 | 4/2009 | Tam et al. |
| 2009/0095621 A1 | 4/2009 | Kao et al. |
| 2009/0098276 A1 | 4/2009 | Burrows |
| 2009/0098706 A1 | 4/2009 | Kim et al. |
| 2009/0104738 A1 | 4/2009 | Ring et al. |
| 2009/0104782 A1 | 4/2009 | Lu et al. |
| 2009/0111280 A1 | 4/2009 | Kao et al. |
| 2009/0117270 A1 | 5/2009 | Yamasaki et al. |
| 2009/0120464 A1 | 5/2009 | Rasheed et al. |
| 2009/0159213 A1 | 6/2009 | Bera et al. |
| 2009/0159588 A1 | 6/2009 | Morioka et al. |
| 2009/0162647 A1 | 6/2009 | Sun et al. |
| 2009/0170221 A1 | 7/2009 | Jacques et al. |
| 2009/0170331 A1 | 7/2009 | Cheng et al. |
| 2009/0179300 A1 | 7/2009 | Arai |
| 2009/0189246 A1 | 7/2009 | Wu et al. |
| 2009/0189287 A1 | 7/2009 | Yang et al. |
| 2009/0191711 A1 | 7/2009 | Rui et al. |
| 2009/0194233 A1 | 8/2009 | Tamura |
| 2009/0194810 A1 | 8/2009 | Kiyotoshi et al. |
| 2009/0197418 A1 | 8/2009 | Sago |
| 2009/0202721 A1 | 8/2009 | Nogami et al. |
| 2009/0214825 A1 | 8/2009 | Sun et al. |
| 2009/0223928 A1 | 9/2009 | Colpo |
| 2009/0226633 A1 | 9/2009 | Laflamme et al. |
| 2009/0236314 A1 | 9/2009 | Chen |
| 2009/0253222 A1 | 10/2009 | Morisawa et al. |
| 2009/0255902 A1 | 10/2009 | Satoh et al. |
| 2009/0258162 A1 | 10/2009 | Furuta et al. |
| 2009/0269934 A1 | 10/2009 | Kao et al. |
| 2009/0274590 A1 | 11/2009 | Willwerth et al. |
| 2009/0275146 A1 | 11/2009 | Takano et al. |
| 2009/0275205 A1 | 11/2009 | Kiehlbauch et al. |
| 2009/0275206 A1 | 11/2009 | Katz et al. |
| 2009/0277587 A1 | 11/2009 | Lubomirsky et al. |
| 2009/0277874 A1 | 11/2009 | Rui et al. |
| 2009/0280650 A1 | 11/2009 | Lubomirsky et al. |
| 2009/0286400 A1 | 11/2009 | Heo et al. |
| 2009/0286405 A1 | 11/2009 | Okesaku et al. |
| 2009/0293809 A1 | 12/2009 | Cho et al. |
| 2009/0294898 A1 | 12/2009 | Feustel et al. |
| 2009/0298256 A1 | 12/2009 | Chen et al. |
| 2009/0314309 A1 | 12/2009 | Sankarakrishnan et al. |
| 2009/0317978 A1 | 12/2009 | Higashi |
| 2009/0320756 A1 | 12/2009 | Tanaka |
| 2010/0000683 A1 | 1/2010 | Kadkhodayan et al. |
| 2010/0003406 A1 | 1/2010 | Lam et al. |
| 2010/0003824 A1 | 1/2010 | Kadkhodayan et al. |
| 2010/0006543 A1 | 1/2010 | Sawada et al. |
| 2010/0022030 A1 | 1/2010 | Ditizio |
| 2010/0025370 A1 | 2/2010 | Dieguez-Campo et al. |
| 2010/0037821 A1 | 2/2010 | Nogami |
| 2010/0039747 A1 | 2/2010 | Sansoni |
| 2010/0047080 A1 | 2/2010 | Bruce |
| 2010/0048022 A1 | 2/2010 | Kubota |
| 2010/0048027 A1 | 2/2010 | Cheng et al. |
| 2010/0055408 A1 | 3/2010 | Lee et al. |
| 2010/0055917 A1 | 3/2010 | Kim |
| 2010/0059889 A1 | 3/2010 | Gosset et al. |
| 2010/0062603 A1 | 3/2010 | Ganguly et al. |
| 2010/0072172 A1 | 3/2010 | Ui et al. |
| 2010/0075503 A1 | 3/2010 | Bencher |
| 2010/0081285 A1 | 4/2010 | Chen et al. |
| 2010/0089533 A1 | 4/2010 | Ueda et al. |
| 2010/0093151 A1 | 4/2010 | Arghavani et al. |
| 2010/0093168 A1 | 4/2010 | Naik |
| 2010/0096367 A1 | 4/2010 | Jeon et al. |
| 2010/0098882 A1 | 4/2010 | Lubomirsky et al. |
| 2010/0099236 A1 | 4/2010 | Kwon et al. |
| 2010/0099263 A1 | 4/2010 | Kao et al. |
| 2010/0101727 A1 | 4/2010 | Ji |
| 2010/0105209 A1 | 4/2010 | Winniczek et al. |
| 2010/0116788 A1 | 5/2010 | Singh et al. |
| 2010/0119843 A1 | 5/2010 | Sun et al. |
| 2010/0129974 A1 | 5/2010 | Futase et al. |
| 2010/0130001 A1 | 5/2010 | Noguchi |
| 2010/0139889 A1 | 6/2010 | Kurita et al. |
| 2010/0144140 A1 | 6/2010 | Chandrashekar et al. |
| 2010/0147219 A1 | 6/2010 | Hsieh et al. |
| 2010/0151149 A1 | 6/2010 | Ovshinsky |
| 2010/0164422 A1 | 7/2010 | Shu et al. |
| 2010/0173499 A1 | 7/2010 | Tao et al. |
| 2010/0178748 A1 | 7/2010 | Subramanian |
| 2010/0178755 A1 | 7/2010 | Lee et al. |
| 2010/0180819 A1 | 7/2010 | Hatanaka et al. |
| 2010/0183825 A1 | 7/2010 | Becker et al. |
| 2010/0187534 A1 | 7/2010 | Nishi et al. |
| 2010/0187588 A1 | 7/2010 | Kim et al. |
| 2010/0187694 A1 | 7/2010 | Yu et al. |
| 2010/0190352 A1 | 7/2010 | Jaiswal |
| 2010/0197143 A1 | 8/2010 | Nishimura |
| 2010/0203739 A1 | 8/2010 | Becker et al. |
| 2010/0206483 A1 | 8/2010 | Sorensen et al. |
| 2010/0207195 A1 | 8/2010 | Fukuzumi et al. |
| 2010/0207205 A1 | 8/2010 | Grebs et al. |
| 2010/0213172 A1 | 8/2010 | Wilson |
| 2010/0240205 A1 | 9/2010 | Son |
| 2010/0243165 A1 | 9/2010 | Um |
| 2010/0243606 A1 | 9/2010 | Koshimizu |
| 2010/0244204 A1 | 9/2010 | Matsuoka et al. |
| 2010/0248488 A1 | 9/2010 | Agarwal et al. |
| 2010/0252068 A1 | 10/2010 | Kannan et al. |
| 2010/0258913 A1 | 10/2010 | Lue |
| 2010/0267224 A1 | 10/2010 | Choi et al. |
| 2010/0267248 A1 | 10/2010 | Ma et al. |
| 2010/0273290 A1 | 10/2010 | Kryliouk |
| 2010/0273291 A1 | 10/2010 | Kryliouk et al. |
| 2010/0288369 A1 | 11/2010 | Chang et al. |
| 2010/0294199 A1 | 11/2010 | Tran et al. |
| 2010/0310785 A1 | 12/2010 | Sasakawa et al. |
| 2010/0314005 A1 | 12/2010 | Saito et al. |
| 2010/0330814 A1 | 12/2010 | Yokota et al. |
| 2011/0005607 A1 | 1/2011 | Desbiolles et al. |
| 2011/0005684 A1 | 1/2011 | Hayami et al. |
| 2011/0008950 A1 | 1/2011 | Xu |
| 2011/0011338 A1 | 1/2011 | Chuc et al. |
| 2011/0034035 A1 | 2/2011 | Liang et al. |
| 2011/0039407 A1 | 2/2011 | Nishizuka |
| 2011/0042799 A1 | 2/2011 | Kim et al. |
| 2011/0045676 A1 | 2/2011 | Park |
| 2011/0048325 A1 | 3/2011 | Choie et al. |
| 2011/0053380 A1 | 3/2011 | Sapre et al. |
| 2011/0058303 A1 | 3/2011 | Migita |
| 2011/0061810 A1 | 3/2011 | Ganguly et al. |

(56) References Cited

U.S. PATENT DOCUMENTS

| | | |
|---|---|---|
| 2011/0061812 A1 | 3/2011 | Ganguly et al. |
| 2011/0065276 A1 | 3/2011 | Ganguly et al. |
| 2011/0076401 A1 | 3/2011 | Chao et al. |
| 2011/0081782 A1 | 4/2011 | Liang et al. |
| 2011/0088847 A1 | 4/2011 | Law et al. |
| 2011/0100489 A1 | 5/2011 | Orito |
| 2011/0111596 A1 | 5/2011 | Kanakasabapathy |
| 2011/0114601 A1 | 5/2011 | Lubomirsky et al. |
| 2011/0115378 A1 | 5/2011 | Lubomirsky et al. |
| 2011/0124144 A1 | 5/2011 | Schlemm et al. |
| 2011/0127156 A1 | 6/2011 | Foad et al. |
| 2011/0133650 A1 | 6/2011 | Kim |
| 2011/0139748 A1 | 6/2011 | Donnelly et al. |
| 2011/0140229 A1 | 6/2011 | Rachmady et al. |
| 2011/0143542 A1 | 6/2011 | Feurprier et al. |
| 2011/0147363 A1 | 6/2011 | Yap et al. |
| 2011/0151674 A1 | 6/2011 | Tang et al. |
| 2011/0151677 A1 | 6/2011 | Wang et al. |
| 2011/0151678 A1 | 6/2011 | Ashtiani et al. |
| 2011/0155181 A1 | 6/2011 | Inatomi |
| 2011/0159690 A1 | 6/2011 | Chandrashekar et al. |
| 2011/0165057 A1 | 7/2011 | Honda et al. |
| 2011/0165347 A1 | 7/2011 | Miller et al. |
| 2011/0165771 A1 | 7/2011 | Ring et al. |
| 2011/0174778 A1 | 7/2011 | Sawada et al. |
| 2011/0180847 A1 | 7/2011 | Ikeda et al. |
| 2011/0195575 A1 | 8/2011 | Wang |
| 2011/0198034 A1 | 8/2011 | Sun et al. |
| 2011/0204025 A1 | 8/2011 | Tahara |
| 2011/0207332 A1 | 8/2011 | Liu et al. |
| 2011/0217851 A1 | 9/2011 | Liang et al. |
| 2011/0226734 A1 | 9/2011 | Sumiya et al. |
| 2011/0227028 A1 | 9/2011 | Sekar et al. |
| 2011/0230008 A1 | 9/2011 | Lakshmanan et al. |
| 2011/0230052 A1 | 9/2011 | Tang et al. |
| 2011/0232737 A1 | 9/2011 | Ruletzki et al. |
| 2011/0232845 A1 | 9/2011 | Riker et al. |
| 2011/0244686 A1 | 10/2011 | Aso et al. |
| 2011/0244693 A1 | 10/2011 | Tamura et al. |
| 2011/0256421 A1 | 10/2011 | Bose et al. |
| 2011/0265884 A1 | 11/2011 | Xu et al. |
| 2011/0265887 A1 | 11/2011 | Lee et al. |
| 2011/0265951 A1 | 11/2011 | Xu |
| 2011/0266252 A1 | 11/2011 | Thadani et al. |
| 2011/0266256 A1 | 11/2011 | Cruse et al. |
| 2011/0266682 A1 | 11/2011 | Edelstein et al. |
| 2011/0278260 A1 | 11/2011 | Lai et al. |
| 2011/0287633 A1 | 11/2011 | Lee et al. |
| 2011/0294300 A1 | 12/2011 | Zhang et al. |
| 2011/0298061 A1 | 12/2011 | Siddiqui et al. |
| 2011/0304078 A1 | 12/2011 | Lee et al. |
| 2011/0308453 A1 | 12/2011 | Su et al. |
| 2012/0003782 A1 | 1/2012 | Byun et al. |
| 2012/0009796 A1 | 1/2012 | Cui et al. |
| 2012/0025289 A1 | 2/2012 | Liang et al. |
| 2012/0031559 A1 | 2/2012 | Dhindsa et al. |
| 2012/0034786 A1 | 2/2012 | Dhindsa et al. |
| 2012/0035766 A1 | 2/2012 | Shajii et al. |
| 2012/0037596 A1 | 2/2012 | Eto et al. |
| 2012/0040492 A1 | 2/2012 | Ovshinsky et al. |
| 2012/0052683 A1 | 3/2012 | Kim et al. |
| 2012/0055402 A1 | 3/2012 | Moriya et al. |
| 2012/0068242 A1 | 3/2012 | Shin et al. |
| 2012/0070982 A1 | 3/2012 | Yu et al. |
| 2012/0070996 A1 | 3/2012 | Hao et al. |
| 2012/0091108 A1 | 4/2012 | Lin et al. |
| 2012/0097330 A1 | 4/2012 | Iyengar et al. |
| 2012/0100720 A1 | 4/2012 | Winniczek et al. |
| 2012/0103518 A1 | 5/2012 | Kakimoto |
| 2012/0104564 A1 | 5/2012 | Won et al. |
| 2012/0119225 A1 | 5/2012 | Shiomi et al. |
| 2012/0122302 A1 | 5/2012 | Weidman et al. |
| 2012/0122319 A1 | 5/2012 | Shimizu |
| 2012/0129354 A1 | 5/2012 | Luong |
| 2012/0135576 A1 | 5/2012 | Lee et al. |
| 2012/0148369 A1 | 6/2012 | Michalski et al. |
| 2012/0149200 A1 | 6/2012 | Culp et al. |
| 2012/0161405 A1 | 6/2012 | Mohn et al. |
| 2012/0164839 A1 | 6/2012 | Nishimura |
| 2012/0171852 A1 | 7/2012 | Yuan et al. |
| 2012/0180954 A1 | 7/2012 | Yang et al. |
| 2012/0181599 A1 | 7/2012 | Lung |
| 2012/0182808 A1 | 7/2012 | Lue et al. |
| 2012/0187844 A1 | 7/2012 | Hoffman et al. |
| 2012/0196447 A1 | 8/2012 | Yang et al. |
| 2012/0196451 A1 | 8/2012 | Mallick |
| 2012/0202408 A1 | 8/2012 | Shajii et al. |
| 2012/0208361 A1 | 8/2012 | Ha |
| 2012/0211462 A1 | 8/2012 | Zhang et al. |
| 2012/0211722 A1 | 8/2012 | Kellam et al. |
| 2012/0222616 A1 | 9/2012 | Han et al. |
| 2012/0222815 A1 | 9/2012 | Sabri et al. |
| 2012/0223048 A1 | 9/2012 | Paranjpe et al. |
| 2012/0223418 A1 | 9/2012 | Stowers et al. |
| 2012/0225557 A1 | 9/2012 | Serry et al. |
| 2012/0228642 A1 | 9/2012 | Aube et al. |
| 2012/0234945 A1 | 9/2012 | Olgado |
| 2012/0238102 A1 | 9/2012 | Zhang et al. |
| 2012/0238103 A1 | 9/2012 | Zhang et al. |
| 2012/0238108 A1 | 9/2012 | Chen et al. |
| 2012/0241411 A1 | 9/2012 | Darling et al. |
| 2012/0247390 A1 | 10/2012 | Sawada et al. |
| 2012/0247670 A1 | 10/2012 | Dobashi et al. |
| 2012/0247671 A1 | 10/2012 | Sugawara |
| 2012/0247677 A1 | 10/2012 | Himori et al. |
| 2012/0255491 A1 | 10/2012 | Hahidi |
| 2012/0258600 A1 | 10/2012 | Godet et al. |
| 2012/0258607 A1 | 10/2012 | Holland et al. |
| 2012/0267346 A1 | 10/2012 | Kao et al. |
| 2012/0269968 A1 | 10/2012 | Rayner |
| 2012/0282779 A1 | 11/2012 | Arnold et al. |
| 2012/0285619 A1 | 11/2012 | Matyushkin et al. |
| 2012/0285621 A1 | 11/2012 | Tan |
| 2012/0291696 A1 | 11/2012 | Clarke |
| 2012/0292664 A1 | 11/2012 | Kanike |
| 2012/0304933 A1 | 12/2012 | Mai et al. |
| 2012/0309204 A1 | 12/2012 | Kang et al. |
| 2012/0309205 A1 | 12/2012 | Wang et al. |
| 2012/0322015 A1 | 12/2012 | Kim |
| 2013/0001899 A1 | 1/2013 | Hwang et al. |
| 2013/0005103 A1 | 1/2013 | Liu et al. |
| 2013/0005140 A1 | 1/2013 | Jeng et al. |
| 2013/0012032 A1 | 1/2013 | Liu et al. |
| 2013/0023062 A1 | 1/2013 | Masuda et al. |
| 2013/0023124 A1 | 1/2013 | Nemani et al. |
| 2013/0023125 A1 | 1/2013 | Singh |
| 2013/0026135 A1 | 1/2013 | Kim |
| 2013/0032574 A1 | 2/2013 | Liu et al. |
| 2013/0034666 A1 | 2/2013 | Liang et al. |
| 2013/0034968 A1 | 2/2013 | Zhang et al. |
| 2013/0037919 A1 | 2/2013 | Sapra et al. |
| 2013/0045605 A1 | 2/2013 | Wang et al. |
| 2013/0049592 A1 | 2/2013 | Yeom et al. |
| 2013/0052804 A1 | 2/2013 | Song |
| 2013/0052827 A1 | 2/2013 | Wang et al. |
| 2013/0052833 A1 | 2/2013 | Ranjan et al. |
| 2013/0059440 A1 | 3/2013 | Wang et al. |
| 2013/0059448 A1 | 3/2013 | Marakhtanov et al. |
| 2013/0062675 A1 | 3/2013 | Thomas |
| 2013/0065398 A1 | 3/2013 | Ohsawa et al. |
| 2013/0082197 A1 | 4/2013 | Yang et al. |
| 2013/0084654 A1 | 4/2013 | Gaylord et al. |
| 2013/0087309 A1 | 4/2013 | Volfovski |
| 2013/0089988 A1 | 4/2013 | Wang et al. |
| 2013/0095646 A1 | 4/2013 | Alsmeier et al. |
| 2013/0098868 A1 | 4/2013 | Nishimura et al. |
| 2013/0105303 A1 | 5/2013 | Lubomirsky et al. |
| 2013/0105948 A1 | 5/2013 | Kewley |
| 2013/0115372 A1 | 5/2013 | Pavol et al. |
| 2013/0118686 A1 | 5/2013 | Carducci et al. |
| 2013/0119016 A1 | 5/2013 | Kagoshima |
| 2013/0119457 A1 | 5/2013 | Lue et al. |
| 2013/0119483 A1 | 5/2013 | Alptekin et al. |
| 2013/0130507 A1 | 5/2013 | Wang et al. |

(56) References Cited

U.S. PATENT DOCUMENTS

| | | |
|---|---|---|
| 2013/0133578 A1 | 5/2013 | Hwang |
| 2013/0150303 A1 | 6/2013 | Kungl et al. |
| 2013/0155568 A1 | 6/2013 | Todorow et al. |
| 2013/0161726 A1 | 6/2013 | Kim et al. |
| 2013/0171810 A1 | 7/2013 | Sun et al. |
| 2013/0175654 A1 | 7/2013 | Muckenhirn et al. |
| 2013/0187220 A1 | 7/2013 | Surthi |
| 2013/0193108 A1 | 8/2013 | Zheng |
| 2013/0213935 A1 | 8/2013 | Liao et al. |
| 2013/0217243 A1 | 8/2013 | Underwood et al. |
| 2013/0224953 A1 | 8/2013 | Salinas et al. |
| 2013/0224960 A1 | 8/2013 | Payyapilly et al. |
| 2013/0260533 A1 | 10/2013 | Sapre et al. |
| 2013/0260564 A1 | 10/2013 | Sapre et al. |
| 2013/0279066 A1 | 10/2013 | Lubomirsky et al. |
| 2013/0284369 A1 | 10/2013 | Kobayashi et al. |
| 2013/0284370 A1 | 10/2013 | Kobayashi et al. |
| 2013/0284373 A1 | 10/2013 | Sun et al. |
| 2013/0284374 A1 | 10/2013 | Lubomirsky et al. |
| 2013/0286530 A1 | 10/2013 | Lin et al. |
| 2013/0295297 A1 | 11/2013 | Chou et al. |
| 2013/0298942 A1 | 11/2013 | Ren et al. |
| 2013/0302980 A1 | 11/2013 | Chandrashekar et al. |
| 2013/0320550 A1 | 12/2013 | Kim |
| 2013/0337655 A1 | 12/2013 | Lee et al. |
| 2013/0343829 A1 | 12/2013 | Benedetti et al. |
| 2014/0004707 A1 | 1/2014 | Thedjoiswono et al. |
| 2014/0004708 A1 | 1/2014 | Thedjoisworo |
| 2014/0008880 A1 | 1/2014 | Miura et al. |
| 2014/0020708 A1 | 1/2014 | Kim et al. |
| 2014/0021673 A1 | 1/2014 | Chen et al. |
| 2014/0026813 A1 | 1/2014 | Wang et al. |
| 2014/0053866 A1 | 2/2014 | Baluja et al. |
| 2014/0054269 A1 | 2/2014 | Hudson et al. |
| 2014/0057447 A1 | 2/2014 | Yang et al. |
| 2014/0062285 A1 | 3/2014 | Chen |
| 2014/0065827 A1 | 3/2014 | Kang et al. |
| 2014/0065842 A1 | 3/2014 | Anthis et al. |
| 2014/0076234 A1 | 3/2014 | Kao et al. |
| 2014/0080308 A1 | 3/2014 | Chen et al. |
| 2014/0080309 A1 | 3/2014 | Park |
| 2014/0080310 A1 | 3/2014 | Chen et al. |
| 2014/0083362 A1 | 3/2014 | Lubomirsky et al. |
| 2014/0087488 A1 | 3/2014 | Nam et al. |
| 2014/0097270 A1 | 4/2014 | Liang et al. |
| 2014/0099794 A1 | 4/2014 | Ingle et al. |
| 2014/0102367 A1 | 4/2014 | Ishibashi |
| 2014/0110061 A1 | 4/2014 | Okunishi |
| 2014/0124364 A1 | 5/2014 | Yoo et al. |
| 2014/0134842 A1 | 5/2014 | Zhange et al. |
| 2014/0134847 A1 | 5/2014 | Seya |
| 2014/0141621 A1 | 5/2014 | Ren et al. |
| 2014/0147126 A1 | 5/2014 | Yamashita et al. |
| 2014/0152312 A1 | 6/2014 | Snow et al. |
| 2014/0154668 A1 | 6/2014 | Chou et al. |
| 2014/0165912 A1 | 6/2014 | Kao et al. |
| 2014/0166617 A1 | 6/2014 | Chen |
| 2014/0166618 A1 | 6/2014 | Tadigadapa et al. |
| 2014/0170853 A1 | 6/2014 | Chien et al. |
| 2014/0175534 A1 | 6/2014 | Kofuji et al. |
| 2014/0186772 A1 | 7/2014 | Pohlers et al. |
| 2014/0190410 A1 | 7/2014 | Kim |
| 2014/0190632 A1 | 7/2014 | Kumar et al. |
| 2014/0191388 A1 | 7/2014 | Chen |
| 2014/0199850 A1 | 7/2014 | Kim et al. |
| 2014/0199851 A1 | 7/2014 | Nemani et al. |
| 2014/0209245 A1 | 7/2014 | Yamamoto et al. |
| 2014/0216337 A1 | 8/2014 | Swaminathan et al. |
| 2014/0225504 A1 | 8/2014 | Kaneko et al. |
| 2014/0227881 A1 | 8/2014 | Lubomirsky et al. |
| 2014/0234466 A1 | 8/2014 | Gao et al. |
| 2014/0248773 A1 | 9/2014 | Tsai et al. |
| 2014/0248780 A1 | 9/2014 | Ingle et al. |
| 2014/0251956 A1 | 9/2014 | Jeon et al. |
| 2014/0256131 A1 | 9/2014 | Wang et al. |
| 2014/0256145 A1 | 9/2014 | Abdallah et al. |
| 2014/0262031 A1 | 9/2014 | Belostotskiy et al. |
| 2014/0262038 A1 | 9/2014 | Wang et al. |
| 2014/0263172 A1 | 9/2014 | Xie et al. |
| 2014/0263272 A1 | 9/2014 | Duan et al. |
| 2014/0264507 A1 | 9/2014 | Lee et al. |
| 2014/0264533 A1 | 9/2014 | Simsek-Ege |
| 2014/0271097 A1 | 9/2014 | Wang et al. |
| 2014/0273373 A1 | 9/2014 | Makala et al. |
| 2014/0273406 A1 | 9/2014 | Wang et al. |
| 2014/0273451 A1 | 9/2014 | Wang et al. |
| 2014/0273462 A1 | 9/2014 | Simsek-Ege et al. |
| 2014/0273487 A1 | 9/2014 | Deshmukh et al. |
| 2014/0273489 A1 | 9/2014 | Wang et al. |
| 2014/0273491 A1 | 9/2014 | Zhang et al. |
| 2014/0273492 A1 | 9/2014 | Anthis et al. |
| 2014/0273496 A1 | 9/2014 | Kao |
| 2014/0288528 A1 | 9/2014 | Py et al. |
| 2014/0302678 A1 | 10/2014 | Paterson et al. |
| 2014/0302680 A1 | 10/2014 | Singh |
| 2014/0308758 A1 | 10/2014 | Nemani et al. |
| 2014/0308816 A1 | 10/2014 | Wang et al. |
| 2014/0311581 A1 | 10/2014 | Belostotskiy et al. |
| 2014/0342532 A1 | 11/2014 | Zhu |
| 2014/0342569 A1 | 11/2014 | Zhu et al. |
| 2014/0349477 A1 | 11/2014 | Chandrashekar et al. |
| 2014/0357083 A1 | 12/2014 | Ling et al. |
| 2014/0361684 A1 | 12/2014 | Ikeda et al. |
| 2014/0363977 A1 | 12/2014 | Morimoto et al. |
| 2014/0363979 A1 | 12/2014 | Or et al. |
| 2015/0007770 A1 | 1/2015 | Chandrasekharan et al. |
| 2015/0011096 A1 | 1/2015 | Chandrasekharan et al. |
| 2015/0014152 A1 | 1/2015 | Hoinkis et al. |
| 2015/0031211 A1 | 1/2015 | Sapre et al. |
| 2015/0037980 A1 | 2/2015 | Rha |
| 2015/0041430 A1 | 2/2015 | Yoshino et al. |
| 2015/0050812 A1 | 2/2015 | Smith |
| 2015/0056814 A1 | 2/2015 | Ling et al. |
| 2015/0060265 A1 | 3/2015 | Cho et al. |
| 2015/0064918 A1 | 3/2015 | Ranjan et al. |
| 2015/0072508 A1 | 3/2015 | Or et al. |
| 2015/0076110 A1 | 3/2015 | Wu et al. |
| 2015/0076586 A1 | 3/2015 | Rabkin et al. |
| 2015/0079797 A1 | 3/2015 | Chen et al. |
| 2015/0093891 A1 | 4/2015 | Zope |
| 2015/0118822 A1 | 4/2015 | Zhang et al. |
| 2015/0118858 A1 | 4/2015 | Takaba |
| 2015/0123541 A1 | 5/2015 | Baek et al. |
| 2015/0126035 A1 | 5/2015 | Diao et al. |
| 2015/0126039 A1 | 5/2015 | Korolik et al. |
| 2015/0126040 A1 | 5/2015 | Korolik et al. |
| 2015/0129541 A1 | 5/2015 | Wang et al. |
| 2015/0129545 A1 | 5/2015 | Ingle et al. |
| 2015/0129546 A1 | 5/2015 | Ingle et al. |
| 2015/0132953 A1 | 5/2015 | Nowling |
| 2015/0132968 A1 | 5/2015 | Ren et al. |
| 2015/0140827 A1 | 5/2015 | Kao et al. |
| 2015/0152072 A1 | 6/2015 | Cantat et al. |
| 2015/0155177 A1 | 6/2015 | Zhang et al. |
| 2015/0167705 A1 | 6/2015 | Lee et al. |
| 2015/0170879 A1 | 6/2015 | Nguyen et al. |
| 2015/0170920 A1 | 6/2015 | Purayath et al. |
| 2015/0170924 A1 | 6/2015 | Nguyen et al. |
| 2015/0170926 A1 | 6/2015 | Michalak |
| 2015/0170935 A1 | 6/2015 | Wang et al. |
| 2015/0170943 A1 | 6/2015 | Nguyen et al. |
| 2015/0171008 A1 | 6/2015 | Luo |
| 2015/0179464 A1 | 6/2015 | Wang et al. |
| 2015/0187625 A1 | 7/2015 | Busche et al. |
| 2015/0191823 A1 | 7/2015 | Banna et al. |
| 2015/0194435 A1 | 7/2015 | Lee |
| 2015/0200042 A1 | 7/2015 | Ling et al. |
| 2015/0206764 A1 | 7/2015 | Wang et al. |
| 2015/0214066 A1 | 7/2015 | Luere et al. |
| 2015/0214067 A1 | 7/2015 | Zhang et al. |
| 2015/0214092 A1 | 7/2015 | Purayath et al. |
| 2015/0214337 A1 | 7/2015 | Ko et al. |
| 2015/0221479 A1 | 8/2015 | Chen et al. |
| 2015/0221541 A1 | 8/2015 | Nemani et al. |

(56) References Cited

U.S. PATENT DOCUMENTS

| | | |
|---|---|---|
| 2015/0228456 A1 | 8/2015 | Ye et al. |
| 2015/0235809 A1 | 8/2015 | Ito et al. |
| 2015/0235860 A1 | 8/2015 | Tomura et al. |
| 2015/0235863 A1 | 8/2015 | Chen |
| 2015/0235865 A1 | 8/2015 | Wang et al. |
| 2015/0235867 A1 | 8/2015 | Nishizuka |
| 2015/0247231 A1 | 9/2015 | Nguyen et al. |
| 2015/0249018 A1 | 9/2015 | Park et al. |
| 2015/0255481 A1 | 9/2015 | Baenninger et al. |
| 2015/0270140 A1 | 9/2015 | Gupta et al. |
| 2015/0275361 A1 | 10/2015 | Lubomirsky et al. |
| 2015/0275375 A1 | 10/2015 | Kim et al. |
| 2015/0279687 A1 | 10/2015 | Xue et al. |
| 2015/0294980 A1 | 10/2015 | Lee et al. |
| 2015/0303031 A1 | 10/2015 | Choi |
| 2015/0332930 A1 | 11/2015 | Wang et al. |
| 2015/0332953 A1 | 11/2015 | Futase et al. |
| 2015/0340225 A1 | 11/2015 | Kim et al. |
| 2015/0340371 A1 | 11/2015 | Lue |
| 2015/0345029 A1 | 12/2015 | Wang et al. |
| 2015/0357201 A1 | 12/2015 | Chen et al. |
| 2015/0357205 A1 | 12/2015 | Wang et al. |
| 2015/0371861 A1 | 12/2015 | Li et al. |
| 2015/0371864 A1 | 12/2015 | Hsu et al. |
| 2015/0371865 A1 | 12/2015 | Chen et al. |
| 2015/0371866 A1 | 12/2015 | Chen et al. |
| 2015/0380419 A1 | 12/2015 | Gunji-Yoneoka et al. |
| 2015/0380431 A1 | 12/2015 | Kanamori et al. |
| 2016/0005572 A1 | 1/2016 | Liang et al. |
| 2016/0005833 A1 | 1/2016 | Collins et al. |
| 2016/0020071 A1 | 1/2016 | Khaja et al. |
| 2016/0027654 A1 | 1/2016 | Kim et al. |
| 2016/0027673 A1 | 1/2016 | Wang et al. |
| 2016/0035586 A1 | 2/2016 | Purayath et al. |
| 2016/0035614 A1 | 2/2016 | Purayath et al. |
| 2016/0042920 A1 | 2/2016 | Cho et al. |
| 2016/0042968 A1 | 2/2016 | Purayath et al. |
| 2016/0043099 A1 | 2/2016 | Purayath et al. |
| 2016/0056167 A1 | 2/2016 | Wang et al. |
| 2016/0056235 A1 | 2/2016 | Lee et al. |
| 2016/0064212 A1 | 3/2016 | Thedjoisworo et al. |
| 2016/0064233 A1 | 3/2016 | Wang et al. |
| 2016/0079062 A1 | 3/2016 | Zheng et al. |
| 2016/0079072 A1 | 3/2016 | Wang et al. |
| 2016/0086772 A1 | 3/2016 | Khaja |
| 2016/0086807 A1 | 3/2016 | Park et al. |
| 2016/0086808 A1 | 3/2016 | Zhang et al. |
| 2016/0086815 A1 | 3/2016 | Pandit et al. |
| 2016/0086816 A1 | 3/2016 | Wang et al. |
| 2016/0093505 A1 | 3/2016 | Chen et al. |
| 2016/0093506 A1 | 3/2016 | Chen et al. |
| 2016/0093737 A1 | 3/2016 | Li et al. |
| 2016/0104606 A1 | 4/2016 | Park et al. |
| 2016/0109863 A1 | 4/2016 | Valcore et al. |
| 2016/0117425 A1 | 4/2016 | Povolny et al. |
| 2016/0118227 A1 | 4/2016 | Valcore et al. |
| 2016/0118268 A1 | 4/2016 | Ingle et al. |
| 2016/0118396 A1 | 4/2016 | Rabkin et al. |
| 2016/0126118 A1 | 5/2016 | Chen et al. |
| 2016/0133480 A1 | 5/2016 | Ko et al. |
| 2016/0136660 A1 | 5/2016 | Song |
| 2016/0141419 A1 | 5/2016 | Baenninger et al. |
| 2016/0148805 A1 | 5/2016 | Jongbloed et al. |
| 2016/0148821 A1 | 5/2016 | Singh et al. |
| 2016/0163512 A1 | 6/2016 | Lubomirsky |
| 2016/0163513 A1 | 6/2016 | Lubomirsky |
| 2016/0172216 A1 | 6/2016 | Marakhtanov et al. |
| 2016/0181112 A1 | 6/2016 | Xue et al. |
| 2016/0181116 A1 | 6/2016 | Berry et al. |
| 2016/0189933 A1 | 6/2016 | Kobayashi et al. |
| 2016/0190147 A1 | 6/2016 | Kato et al. |
| 2016/0196969 A1 | 7/2016 | Berry et al. |
| 2016/0196984 A1 | 7/2016 | Lill et al. |
| 2016/0196985 A1 | 7/2016 | Tan et al. |
| 2016/0203958 A1 | 7/2016 | Arase et al. |
| 2016/0204009 A1 | 7/2016 | Nguyen et al. |
| 2016/0208395 A1* | 7/2016 | Ooshima ........... H01J 37/32926 |
| 2016/0218018 A1 | 7/2016 | Lieu et al. |
| 2016/0222522 A1 | 8/2016 | Wang et al. |
| 2016/0225651 A1 | 8/2016 | Tran et al. |
| 2016/0225652 A1 | 8/2016 | Tran et al. |
| 2016/0237570 A1 | 8/2016 | Tan et al. |
| 2016/0240353 A1 | 8/2016 | Nagami |
| 2016/0240389 A1 | 8/2016 | Zhang et al. |
| 2016/0240402 A1 | 8/2016 | Park et al. |
| 2016/0260588 A1 | 9/2016 | Park et al. |
| 2016/0260616 A1 | 9/2016 | Li et al. |
| 2016/0260619 A1 | 9/2016 | Zhang et al. |
| 2016/0284556 A1 | 9/2016 | Ingle et al. |
| 2016/0293398 A1 | 10/2016 | Danek et al. |
| 2016/0293438 A1 | 10/2016 | Zhou et al. |
| 2016/0300694 A1 | 10/2016 | Yang et al. |
| 2016/0307772 A1 | 10/2016 | Choi et al. |
| 2016/0307773 A1 | 10/2016 | Lee et al. |
| 2016/0314961 A1 | 10/2016 | Liu et al. |
| 2016/0314985 A1 | 10/2016 | Yang et al. |
| 2016/0319452 A1 | 11/2016 | Eidschun et al. |
| 2016/0340781 A1 | 11/2016 | Thomas et al. |
| 2016/0343548 A1 | 11/2016 | Howald et al. |
| 2016/0358793 A1 | 12/2016 | Okumura et al. |
| 2017/0011922 A1 | 1/2017 | Tanimura et al. |
| 2017/0040175 A1 | 2/2017 | Xu et al. |
| 2017/0040190 A1 | 2/2017 | Benjaminson et al. |
| 2017/0040191 A1 | 2/2017 | Benjaminson et al. |
| 2017/0040207 A1 | 2/2017 | Purayath |
| 2017/0040214 A1 | 2/2017 | Lai et al. |
| 2017/0053808 A1 | 2/2017 | Kamp et al. |
| 2017/0062184 A1 | 3/2017 | Tran et al. |
| 2017/0110290 A1 | 4/2017 | Kobayashi et al. |
| 2017/0110335 A1 | 4/2017 | Yang et al. |
| 2017/0110475 A1 | 4/2017 | Liu et al. |
| 2017/0133202 A1 | 5/2017 | Berry |
| 2017/0178894 A1 | 6/2017 | Stone et al. |
| 2017/0178899 A1 | 6/2017 | Kabansky et al. |
| 2017/0178924 A1 | 6/2017 | Chen et al. |
| 2017/0194128 A1 | 7/2017 | Lai et al. |
| 2017/0207088 A1 | 7/2017 | Kwon et al. |
| 2017/0226637 A1 | 8/2017 | Lubomirsky et al. |
| 2017/0229287 A1 | 8/2017 | Xu et al. |
| 2017/0229289 A1 | 8/2017 | Lubomirsky et al. |
| 2017/0229291 A1 | 8/2017 | Singh et al. |
| 2017/0229293 A1 | 8/2017 | Park et al. |
| 2017/0229326 A1 | 8/2017 | Tran et al. |
| 2017/0229328 A1 | 8/2017 | Benjaminson et al. |
| 2017/0229329 A1 | 8/2017 | Benjaminson et al. |
| 2017/0236694 A1 | 8/2017 | Eason et al. |
| 2017/0250193 A1 | 8/2017 | Huo |
| 2017/1042703 | 8/2017 | Liang et al. |
| 2017/0294445 A1 | 10/2017 | Son et al. |
| 2017/0309509 A1 | 10/2017 | Tran et al. |
| 2017/0338133 A1 | 11/2017 | Tan et al. |
| 2017/0338134 A1 | 11/2017 | Tan et al. |
| 2017/0373082 A1 | 12/2017 | Sekine et al. |
| 2018/0005850 A1 | 1/2018 | Citla et al. |
| 2018/0006050 A1 | 1/2018 | Watanabe et al. |
| 2018/0025900 A1 | 1/2018 | Park et al. |
| 2018/0069000 A1 | 3/2018 | Bergendahl et al. |
| 2018/0076031 A1 | 3/2018 | Yan et al. |
| 2018/0076044 A1 | 3/2018 | Choi et al. |
| 2018/0076083 A1 | 3/2018 | Ko et al. |
| 2018/0080124 A1 | 3/2018 | Bajaj et al. |
| 2018/0082861 A1 | 3/2018 | Citla et al. |
| 2018/0096818 A1 | 4/2018 | Lubomirsky |
| 2018/0096819 A1 | 4/2018 | Lubomirsky et al. |
| 2018/0096821 A1 | 4/2018 | Lubomirsky et al. |
| 2018/0096865 A1 | 4/2018 | Lubomirsky et al. |
| 2018/0102255 A1 | 4/2018 | Chen et al. |
| 2018/0102256 A1 | 4/2018 | Chen et al. |
| 2018/0102259 A1 | 4/2018 | Wang et al. |
| 2018/0130818 A1 | 5/2018 | Kim et al. |
| 2018/0138049 A1 | 5/2018 | Ko et al. |
| 2018/0138055 A1 | 5/2018 | Xu et al. |
| 2018/0138075 A1 | 5/2018 | Kang et al. |
| 2018/0138085 A1 | 5/2018 | Wang et al. |

(56) References Cited

U.S. PATENT DOCUMENTS

| | | |
|---|---|---|
| 2018/0175051 A1 | 6/2018 | Lue et al. |
| 2018/0182633 A1 | 6/2018 | Pandit et al. |
| 2018/0182777 A1 | 6/2018 | Cui et al. |
| 2018/0223437 A1 | 8/2018 | Geroge et al. |
| 2018/0226223 A1 | 8/2018 | Lubomirsky |
| 2018/0226230 A1 | 8/2018 | Kobayashi et al. |
| 2018/0226259 A1 | 8/2018 | Choi et al. |
| 2018/0226278 A1 | 8/2018 | Arnepalli et al. |
| 2018/0226425 A1 | 8/2018 | Purayath |
| 2018/0226426 A1 | 8/2018 | Purayath |
| 2018/0240654 A1 | 8/2018 | Park et al. |
| 2018/0261516 A1 | 9/2018 | Lin et al. |
| 2018/0261686 A1 | 9/2018 | Lin et al. |
| 2018/0366351 A1 | 12/2018 | Lubomirsky |

FOREIGN PATENT DOCUMENTS

| | | |
|---|---|---|
| CN | 101236893 A | 8/2008 |
| CN | 101378850 A | 3/2009 |
| CN | 102893705 | 1/2013 |
| EP | 1675160 A1 | 6/2006 |
| JP | S59-126778 A | 7/1984 |
| JP | S62-45119 A | 2/1987 |
| JP | 63301051 A | 12/1988 |
| JP | H01-200627 A | 8/1989 |
| JP | H02-114525 A | 4/1990 |
| JP | H07-153739 A | 6/1995 |
| JP | H8-31755 A | 2/1996 |
| JP | H08-107101 A | 4/1996 |
| JP | H08-264510 A | 10/1996 |
| JP | H09-260356 A | 10/1997 |
| JP | 2001-313282 A | 11/2001 |
| JP | 2001-332608 A | 11/2001 |
| JP | 2002-075972 A | 3/2002 |
| JP | 2002-083869 A | 3/2002 |
| JP | 2003-174020 A | 6/2003 |
| JP | 2003-282591 A | 10/2003 |
| JP | 2004-508709 A | 3/2004 |
| JP | 2004-296467 A | 10/2004 |
| JP | 2005-050908 A | 2/2005 |
| JP | 2006-041039 A | 2/2006 |
| JP | 2006-066408 A | 3/2006 |
| JP | 2008-288560 A | 11/2008 |
| JP | 4191137 B2 | 12/2008 |
| JP | 2009-141343 A | 6/2009 |
| JP | 2009-530871 A | 8/2009 |
| JP | 2009-239056 A | 10/2009 |
| JP | 2010-180458 | 8/2010 |
| JP | 2011-508436 A | 3/2011 |
| JP | 2011-518408 A | 6/2011 |
| JP | 4763293 B2 | 8/2011 |
| JP | 2011-171378 A | 9/2011 |
| JP | 2012-19164 A | 1/2012 |
| JP | 2012-019194 A | 1/2012 |
| JP | 2012-512531 A | 5/2012 |
| JP | 2013-243418 A | 12/2013 |
| JP | 5802323 B2 | 10/2015 |
| JP | 2016-111177 A | 6/2016 |
| KR | 10-2000-008278 A | 2/2000 |
| KR | 10-2000-0064946 A | 11/2000 |
| KR | 10-2001-0056735 A | 7/2001 |
| KR | 2003-0023964 A | 3/2003 |
| KR | 10-2003-0054726 A | 7/2003 |
| KR | 10-2003-0083663 A | 10/2003 |
| KR | 100441297 B1 | 7/2004 |
| KR | 10-2005-0007143 A | 1/2005 |
| KR | 10-2005-0042701 A | 5/2005 |
| KR | 2005-0049903 A | 5/2005 |
| KR | 10-2006-0080509 A | 7/2006 |
| KR | 1006-41762 B1 | 11/2006 |
| KR | 10-2006-0127173 A | 12/2006 |
| KR | 100663668 B1 | 1/2007 |
| KR | 100678696 B1 | 1/2007 |
| KR | 100712727 B1 | 4/2007 |
| KR | 2007-0079870 A | 8/2007 |
| KR | 10-2008-0063988 A | 7/2008 |
| KR | 10-0843236 B1 | 7/2008 |
| KR | 10-2009-0040869 A | 4/2009 |
| KR | 10-2009-0128913 A | 12/2009 |
| KR | 10-2010-0013980 A | 2/2010 |
| KR | 10-2010-0093358 A | 8/2010 |
| KR | 10-2011-0086540 A | 7/2011 |
| KR | 10-2011-0114538 A | 10/2011 |
| KR | 10-2011-0126675 A | 11/2011 |
| KR | 10-2012-0022251 A | 3/2012 |
| KR | 10-2012-0082640 A | 7/2012 |
| KR | 10-2016-0002543 A | 1/2016 |
| TW | 2006-12480 A | 4/2006 |
| TW | 200709256 A | 3/2007 |
| TW | 2007-35196 A | 9/2007 |
| TW | 2011-27983 A1 | 8/2011 |
| TW | 2012-07919 | 2/2012 |
| TW | 2012-13594 A | 4/2012 |
| TW | 2012-33842 A1 | 8/2012 |
| WO | 2008-112673 A2 | 9/2008 |
| WO | 2009-009611 A2 | 1/2009 |
| WO | 2009-084194 A1 | 7/2009 |
| WO | 2010-010706 | 1/2010 |
| WO | 2010-113946 A1 | 10/2010 |
| WO | 2011-027515 A | 3/2011 |
| WO | 2011-031556 A | 3/2011 |
| WO | 2011070945 A1 | 6/2011 |
| WO | 2011-095846 A1 | 8/2011 |
| WO | 2011-149638 A | 12/2011 |
| WO | 2012-050321 A | 4/2012 |
| WO | 2012-118987 A1 | 9/2012 |
| WO | 2012-125656 A2 | 9/2012 |
| WO | 2012-148568 A1 | 11/2012 |
| WO | 2013-118260 A1 | 8/2013 |

OTHER PUBLICATIONS

International Search Report and Written Opinion of PCT/US2017/033362 dated Aug. 24, 2017, all pages.

Won et al. Derwent 2006-065772; Sep. 7, 2014, 10 pages.

International Search Report and Written Opinion of PCT/US2017/060696 dated Jan. 25, 2018, all pages.

International Search Report and Written Opinion of PCT/US2017/055431 dated Jan. 19, 2018, all pages.

International Search Report and Written Opinion of PCT/US2018/016261 dated May 21, 2018, all pages.

International Search Report and Written Opinion of PCT/US2018/016648 dated May 18, 2018, all pages.

H. Xiao, Introduction to Semiconductor Manufacturing Technology, published by Prentice Hall, 2001, ISBN 0-13-022404-9, pp. 354-356.

Manual No. TQMA72E1. "Bayard-Alpert Pirani Gauge FRG-730: Short Operating Instructions" Mar. 2012. Agilent Technologies, Lexington, MA 02421, USA. pp. 1-45.

International Search Report and Written Opinion of PCT/US2016/045551 dated Nov. 17, 2016, all pages.

International Search Report and Written Opinion of PCT/US2016/045543 dated Nov. 17, 2016, all pages.

"Liang et al. Industrial Application of Plasma Process vol. 3, pp. 61-74, 2010".

Instrument Manual: Vacuum Gauge Model MM200, Rev D. TELEVAC (website: www.televac.com), A Division of the Fredericks Company, Huntingdon Valley, PA, US. 2008. pp. 162.

J.J. Wang and et al., "Inductively coupled plasma etching of bulk 1-20 6H—SiC and thin-film SiCN in NF3 chemistries," Journal of Vacuum Science & Technology A: Vacuum, Surfaces, and Films 16, 2204 (1998).

* cited by examiner

OPTICAL EMISSION SPECTROSCOPIC TECHNIQUES FOR MONITORING ETCHING

TECHNICAL FIELD

The present disclosure applies broadly to the field of plasma processing. More specifically, methods and systems for etching layers using optical emission spectroscopy are disclosed.

BACKGROUND

Integrated circuits are made possible by processes which produce intricately patterned material layers on substrate surfaces. Producing patterned material on a substrate requires controlled methods for removal of exposed material. Chemical etching is used for a variety of purposes including transferring a pattern in photoresist into underlying layers, thinning layers, or thinning lateral dimensions of features already present on the surface. Often it is desirable to have an etch process that etches one material faster than another facilitating, for example, a pattern transfer process. Such an etch process is said to be selective to the first material. As a result of the diversity of materials, circuits, and processes, etch processes have been developed with a selectivity towards a variety of materials.

Dry etches produced in local plasmas formed within the substrate processing region can penetrate more constrained trenches and exhibit less deformation of delicate remaining structures than wet etches. However, even though an etch process may be selective to a first material over a second material, some undesired etching of the second material may still occur.

Thus, there is a need for improved systems and methods that can be used to produce high quality devices and structures. These and other needs are addressed by the present technology.

BRIEF SUMMARY

Embodiments of the present technology may allow for partial etching of a semiconductor layer. Partial etching of a semiconductor layer may include removing 500 Angstroms or less from the thickness of the layer. Embodiments may permit accurate and precise partial etching of the layer, regardless of different chamber conditioning recipes and the amount of etchant compounds or precursors that may be adsorbed on the chamber walls. Embodiments allow for improved etching by non-invasively monitoring the etch process with optical emission spectroscopy. Even without an emission line that has a strong correlation with the amount etched, embodiments include methods and systems using emission that can be strongly correlated with the amount etched. Methods include integrating an emission signal over the entire etch process and using existing inert gases in the process for actinometry.

Embodiments may include a method of etching. The method may include striking a plasma discharge. The method may also include flowing a gas mixture through the plasma discharge to form plasma effluents. The method may further include flowing the plasma effluents through a plurality of apertures to a layer on a substrate. The layer may have a first thickness. In addition, the method may include etching the layer with the plasma effluents. The method may also include measuring the intensity of emission from a reaction of plasma effluents with the layer. The method may further include summing the intensity of the emission while the plasma effluents are being flowed to the layer to obtain an integrated intensity. The method may then include comparing the integrated intensity to a reference value corresponding to a target etch thickness. Additionally, the method may include extinguishing the plasma discharge when the integrated intensity is equal to or greater than the reference value. The method may then define a partially etched layer on the substrate having a second thickness less than the first thickness.

Embodiments may include a method of measuring an amount of a layer etched with a remote plasma source. The method may include measuring the intensity of emission from a reaction of plasma effluents with the layer. The method may also include summing the intensity of the emission over the duration that the plasma effluents are being flowed to the layer to obtain an integrated intensity. The method may further include measuring the amount of the layer etched by comparing the integrated intensity to a calibration curve.

Embodiments may include a processing system. The processing system may include a plasma subsystem. The plasma subsystem may include a power supply. The power supply may be configured to ignite a plasma and ionize a gas mixture with the plasma subsystem. The processing system may also include a gas injection subsystem in fluid communication with the plasma subsystem. The processing system may further include a substrate processing chamber in fluid communication with the plasma subsystem. The substrate processing chamber may be separate from the plasma subsystem by a plate defining a plurality of apertures. The processing system may also include an optical detector aligned with a viewport in the plasma subsystem. In addition, the processing system may include a processor. The processor may be configure to receive a signal from the optical detector. The processor may be operatively coupled to the power supply and the gas injection system. The processor may be programmed to adjust the power of the power supply to strike a plasma discharge. The processor may be programmed to receive a signal from the optical detector. The signal may be indicative of the intensity of emission in the substrate processing chamber. The processor may be programmed to sum the signal over a period to obtain an integrated signal. The processor may be programmed to compare the integrated signal to a reference value. The processor may further be programmed to adjust the power of the power supply to extinguish the plasma discharge when the integrated signal is greater than or equal to the reference value.

Embodiments may include a method of etching. The method may include striking a plasma discharge. The method may also include flowing a gas mixture through the plasma discharge to form plasma effluents. The gas mixture may include a first gas and an inert gas. The inert gas may be present in the gas mixture at a concentration above trace levels. The method may further include flowing the plasma effluents through a plurality of apertures to a layer on a substrate. The layer may have a first thickness. In addition, the method may include etching the layer with the plasma effluents. The rate of etching may be higher than if the inert gas was excluded from the gas mixture. The method may include measuring the intensity of emission from the first gas from a reaction of plasma effluents with the layer. The method may also include measuring the intensity of emission from the inert gas from the reaction of plasma effluents with the layer. The method may further include calculating a parameter from the intensity of emission from the first gas and the intensity of emission from the inert gas. The parameter may be compared to a reference value that corresponds to a target thickness of the layer etched. The method may include extinguishing the plasma discharge when the parameter is equal to or exceeds the reference value. These operations in the method may then define a partially etched layer having a second thickness less than the first thickness.

DETAILED DESCRIPTION

Figure 1:
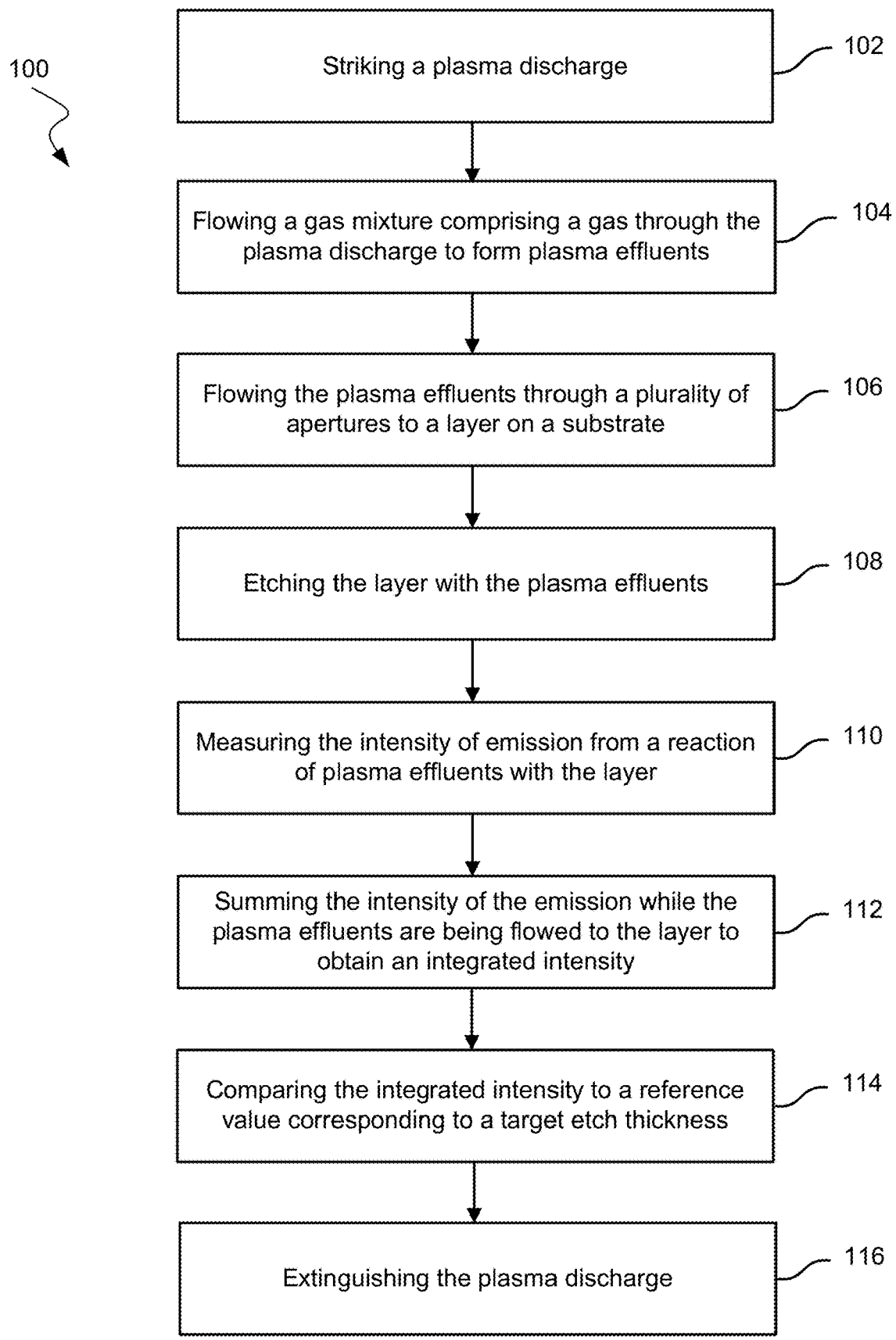
FIG. 1 shows a method of etching according to embodiments of the present technology.

Conventional methods of monitoring etching by optical emission spectroscopy (OES) often involve signals of species that change in intensity when a layer has finished etching. This method may be referred to as endpoint detection. However, as semiconductor devices shrink, semiconductor processing includes the partial etching of layers, so that the layer is reduced in thickness but not fully etched away. Endpoint detection techniques may not work as the intensity of an emission signal may not change significantly after a certain thickness is reached. Moreover, the partial etching of layers may be with a remote plasma, where radicals are primarily responsible for the etch. The population of the radicals may be hard to estimate based on the emission signals. The signals with OES at certain pressures may not correlate well with etch amount. Partial pressures of gases may change during processing and may not be adequately accounted for with a conventional OES measurement. As a result, a method and a system is needed that can monitor the partial etching of a layer.

In addition to conventional OES, other radical measurement techniques may not be well suited for monitoring partial etching of layers. For example, with nondispersive infrared (NDIR) detection, the $NF_3$ signal does not have a strong correlation with the thickness etched, and the $NF_3$ signal may not accurately show the drift in chamber etch rates over time. The $SiF_4$ NDIR signal may be too weak to be detected by conventional NDIR detectors. Cavity Ring Down Spectroscopy may require more sophisticated equipment and may be prohibitively expensive. Self-OES involves creating a secondary plasma, but the secondary plasma may affect the etch processing of the layer. Likewise, a residual gas analyzer (RGA) may also require an additional plasma. And while the etch rate may be characterized by measuring etch on a blanket wafer, the blanket wafer cannot be measured at the same time as a layer on a process wafer is processed, and therefore, the blanket wafer cannot provide information specific to a particular process wafer, which may have an etch rate affected by chamber drift. Additionally, a blanket wafer increases processing costs.

OES may have several advantages over other techniques. OES is generally not intrusive and non-invasive. Additionally, OES may monitor a range of emission wavelengths and therefore may monitor multiple species or improve the signal with one species. Also, emission from each radical or molecule may be unique, which may allow analysis of the etch chemistry. Embodiments of the present technology improve semiconductor technology and etch technology by providing methods and systems to accurately and precisely measure partial etching of a layer, including at pressures greater than 1 Torr. Methods include integrating an emission signal over an entire etch process and using existing inert gases in the process for actinometry. Embodiments may allow for a strong correlation of a signal or a calculated parameter from the signal with the amount etched.

Methods and systems described herein may improve semiconductor processing technology by providing more efficient, faster, and cheaper techniques of patterning. Being able to measure the progress of a partial etch of a layer in situ may allow for these advantages.

I. Signal Integration

A. Method of Etching

FIG. 1 shows a method 100 of etching. Method 100 may include striking a plasma discharge (block 102). The plasma discharge may be capacitively coupled or inductively coupled.

Method 100 may also include flowing a gas mixture including a gas through the plasma discharge to form plasma effluents (block 104). The gas may be a hydrogen-containing gas. The gas mixture may include at least one of fluorine-containing gas, a helium-containing gas, and a nitrogen-containing gas. The fluorine-containing gas may be HF. The helium-containing gas may be helium. The nitrogen containing gas may be $N_2$.

Method 100 may further include flowing the plasma effluents through a plurality of apertures to a layer on a substrate (block 106). The layer may have a first thickness. The layer may be a silicon layer. The silicon layer may be patterned or unpatterned. A patterned silicon layer may include features, such as trenches and vias, with a characteristic dimension 10 nm or less, 8 nm or less, 6 nm or less, or 5 nm or less. The substrate may be a semiconductor substrate, such as a silicon wafer. The substrate may include a wafer and layers on top of the wafer. The layers may be patterned or unpatterned. The apertures may be defined by a plate, and the apertures may be holes in a showerhead.

At block 108, method 100 may include etching the layer with the plasma effluents. The plasma effluents may react with the layer in a chamber. The pressure during the reaction may be greater than or equal to 1 Torr. The pressure may be in a range from 1 to 2 Torr, 2 to 3 Torr, 3 to 4 Torr, 4 to 6 Torr, 6 to 8 Torr, or 8 to 10 Torr in embodiments.

At block 110, method 100 may also include measuring the intensity of emission from a reaction of plasma effluents with the layer. The emission may be from hydrogen. For example, the emission may be hydrogen at 486.1 nm or 656.3 nm. In these and other embodiments, the emission may be helium at 706.5 nm, helium at 728.1 nm, $N_2$ at 337.1 nm, fluorine at 685.6 nm, or fluorine at 703.8 nm.

Method 100 may further include summing the intensity of the emission while the plasma effluents are being flowed to the layer to obtain an integrated intensity (block 112). Summing the intensity may be over the entire duration of the plasma effluents being flowed to the silicon layer. The entire duration may be in a range from 10 seconds to 600 seconds, including from 10 seconds to 60 seconds, from 60 seconds to 100 seconds, from 100 seconds to 120 seconds, from 120 seconds to 240 seconds, from 240 seconds to 360 seconds, from 360 seconds to 480 seconds, or from 480 seconds to 600 seconds. The idea of summing the intensity over the duration is to account for the time the layer is being etched. Method 100 may exclude intensity of emissions not summed over the time the layer has been etched.

Method 100 may then include comparing the integrated intensity to a reference value corresponding to a target thickness (block 114). The target thickness may represent the target thickness to be etched or removed. The target thickness may be in a range from 10 to 500 Å, including 10 to 100 Å, 100 to 200 Å, 200 to 300 Å, 300 to 400 Å, or 400 to 500 Å in embodiments. The reference value may be obtained from a calibration curve, which relates integrated intensity to target thickness. For example, the calibration curve may show an expected integrated intensity corresponding to a target thickness. Method 100 may also include calculating the reference value from an equation relating integrated intensity to target thickness. The equation may take target thickness as an independent variable and calculate the integrated intensity as the dependent variable. The reference value may be the integrated intensity of hydrogen corresponding to the target thickness. The reference value may appropriately account for drift in target thickness after an in situ chamber clean, or the reference value may account for different durations of in situ chamber cleans. The method may exclude using emission from fluorine for determining the applicable target thickness or for determining when to extinguish the plasma discharge.

Additionally, method 100 may include extinguishing the plasma discharge (block 116) when the integrated intensity is equal to or greater than the reference value. Method 100 may then define a partially etched layer on the substrate having a second thickness less than the first thickness. The second thickness may be less than or equal to the first thickness minus the target thickness. In embodiments, the difference between the second thickness and the first thickness is within 5%, 10%, 15%, or 20% of the first thickness.

Method 100 may include removing the substrate from the chamber after extinguishing the plasma discharge. The substrate may be placed into a front opening unified pod (FOUP).

B. Method of Measuring

Figure 2:
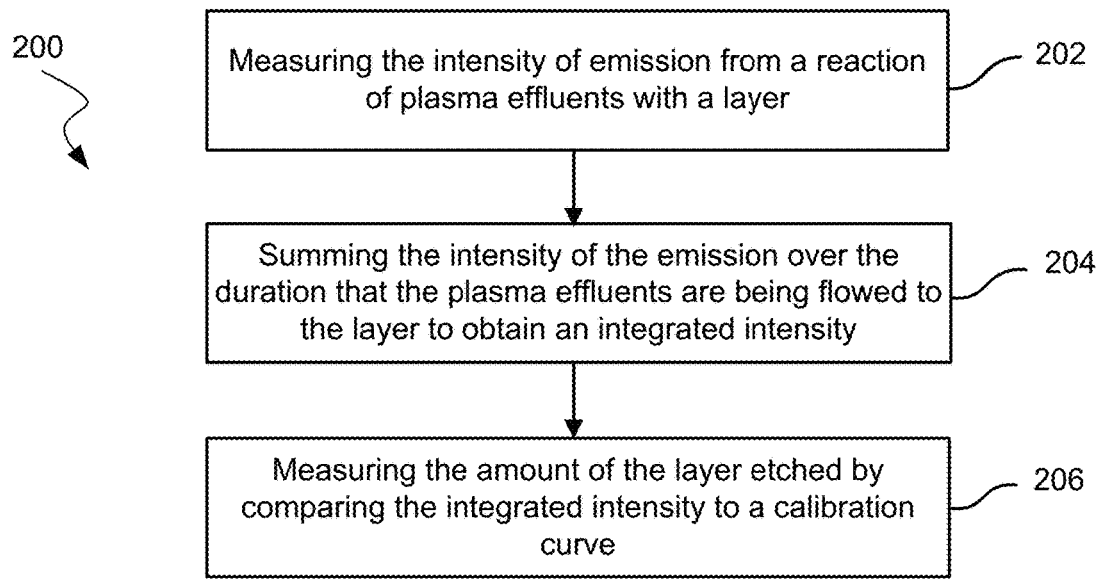
FIG. 2 shows a method of measuring an amount of a layer etched according to embodiments of the present technology.

FIG. 2 shows a method 200 of measuring an amount of a layer etched with a plasma source. The layer may be a silicon layer.

Method 200 may include measuring the intensity of emission from a reaction of plasma effluents with the layer (block 202). The emission may be a wavelength. Specifically, the wavelength may be associated with a species in the plasma effluents or created by the plasma effluents. The emission may be any emission described herein.

Method 200 may also include summing the intensity of the emission over the duration that the plasma effluents are being flowed to the layer to obtain an integrated intensity (block 204). Summing the intensity of the emission may be by any technique described herein.

Method 200 may further include measuring the amount of the layer etched by comparing the integrated intensity to a calibration curve (block 206). The calibration curve may relate previously obtained intensity values with etch amounts or etch thicknesses. The calibration curve may be an equation (e.g., a linear regression) or a single point for the integrated intensity corresponding to a target thickness. The amount of the layer etched may be less than a thickness of the layer before the plasma effluents are flowed to the layer.

C. System

Embodiments may include a processing system. The processing system may include a plasma subsystem. The plasma subsystem may include a power supply. The power supply may be configured to ignite a plasma and ionize a gas mixture with the plasma subsystem. The power supply may be configured to deliver a power ranging from 30 W to 1,000 W to the plasma subsystem to ignite the plasma. The plasma subsystem may include an electrode. The electrode may be in electrical communication with the power supply.

The processing system may also include a gas injection subsystem in fluid communication with the plasma subsystem. The processing system may further include a substrate processing chamber in fluid communication with the plasma subsystem. The substrate processing chamber may be separate from the plasma subsystem by a plate defining a plurality of apertures.

The processing system may also include an optical detector aligned with a viewport in the plasma subsystem. The optical detector may be configured to measure emission intensity at wavelengths from 200 nm to 800 nm. In addition, the processing system may include a processor. The processor may be configured to receive a signal from the optical detector. The processor may be operatively coupled to the power supply and the gas injection system. The processor may be programmed to adjust the power of the power supply to strike a plasma discharge. The processor may be programmed to receive a signal from the optical detector. The signal may be indicative of the intensity of emission in the substrate processing chamber. The processor may be programmed to sum the signal over a period to obtain an integrated signal. The processor may be programmed to compare the integrated signal to a reference value. The processor may further be programmed to adjust the power of the power supply to extinguish the plasma discharge when the integrated signal is greater than or equal to the reference value.

The processing system may include a pump in fluid communication with the substrate processing chamber. The pump may be configured to reduce the pressure of the substrate processing chamber to a range from 1 Torr to 10 Torr.

D. Example

Figure 3:
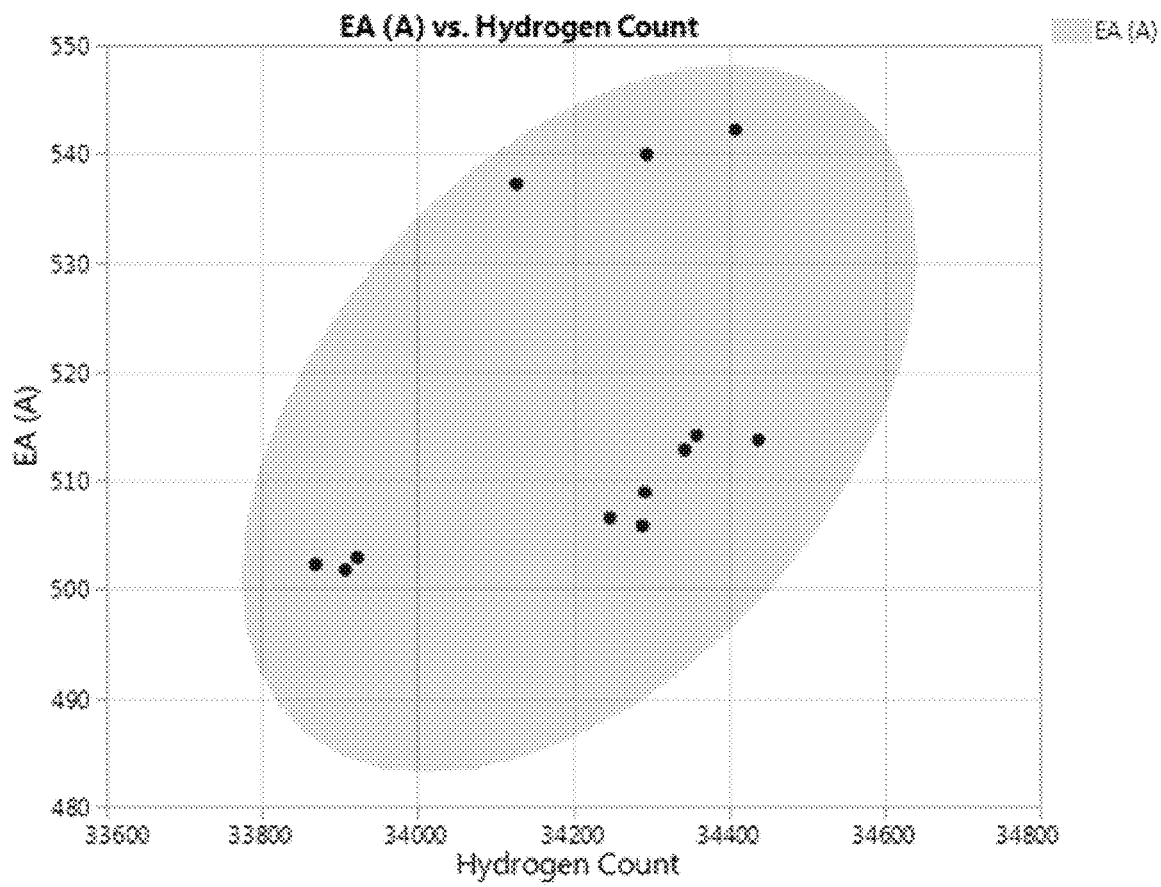
FIG. 3 shows a graph of the etch amount versus a hydrogen signal according to embodiments of the present technology.

FIG. 3 shows a graph of the etch amount (EA) in angstroms versus the intensity of hydrogen at 656.3 nm. The etch amount was measured by ellipsometry. The same recipe for etching silicon was run 12 times. However, the etch amount was extremely variable for even the same etch recipe. The maximum difference in etch amount for the same hydrogen count was 35 Å, or about 7% of the total amount etched. Part of the reason for the scatter was likely related to the different in situ chamber clean times used before running the recipe. The variability in the results shows that the etch amount would differ for different chamber clean times and likely would drift depending on wafers processed since the last chamber clean. An in situ chamber clean may involve running a plasma with a fluorine-containing gas to remove species adsorbed onto chamber walls and other surfaces.

Figure 4A:
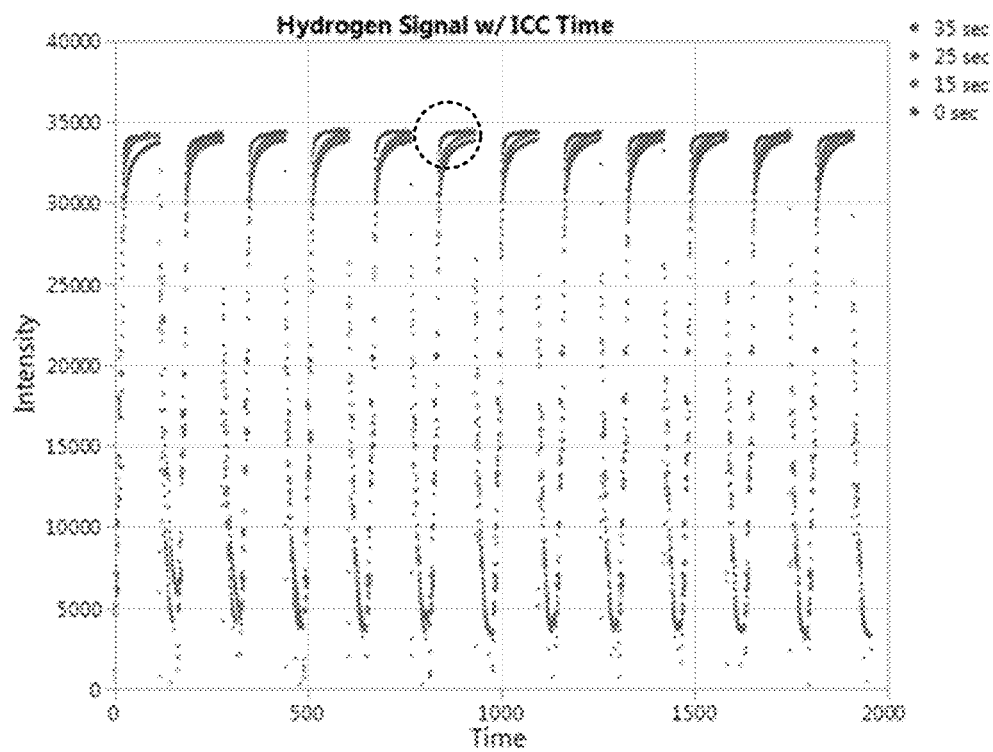
FIG. 4A and FIG. 4B shows the intensity of hydrogen emission during etching for different in situ chamber cleaning times according to embodiments of the present technology.
Figure 4B:
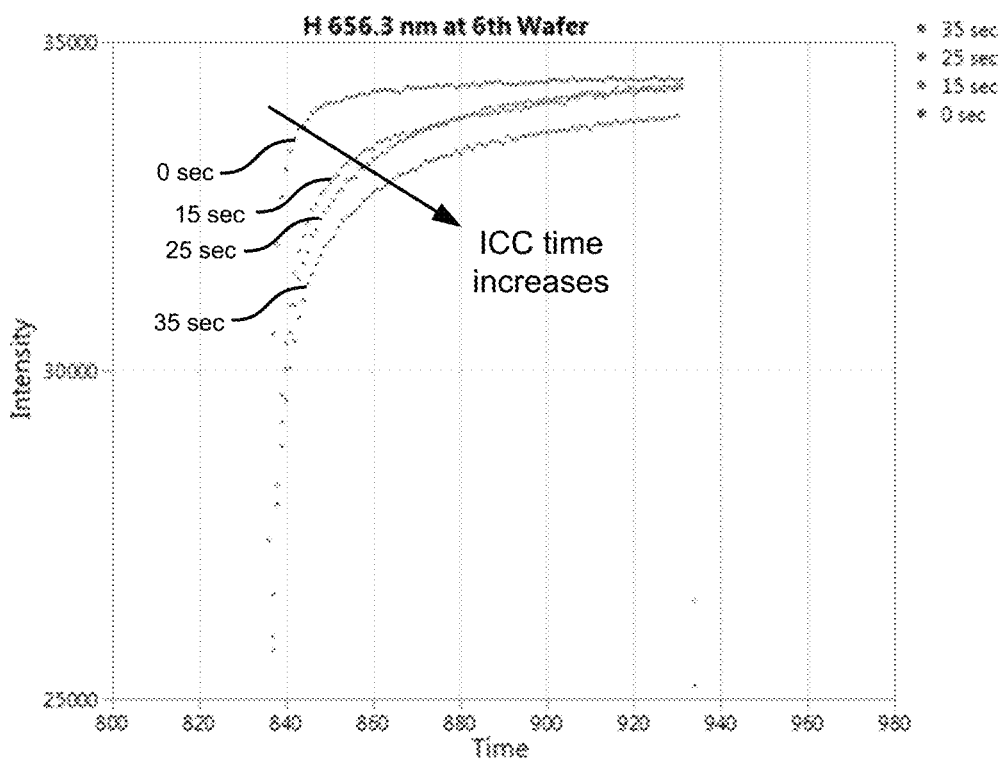

FIG. 4A shows the intensity of hydrogen emission during etching for different in situ chamber cleaning (ICC) times. The section of the graph indicated by the dashed circle is shown in more detail in FIG. 4B. As seen in these figures, the intensity of the hydrogen signal decreases as ICC time increases. Without intending to be bound by theory, it is possible that a longer ICC time results in removing hydrogen adsorbed onto the surface of the chamber walls and other components. During etching, hydrogen adsorbs onto the chamber surfaces, when the hydrogen would have otherwise participated in etching.

Figure 5:
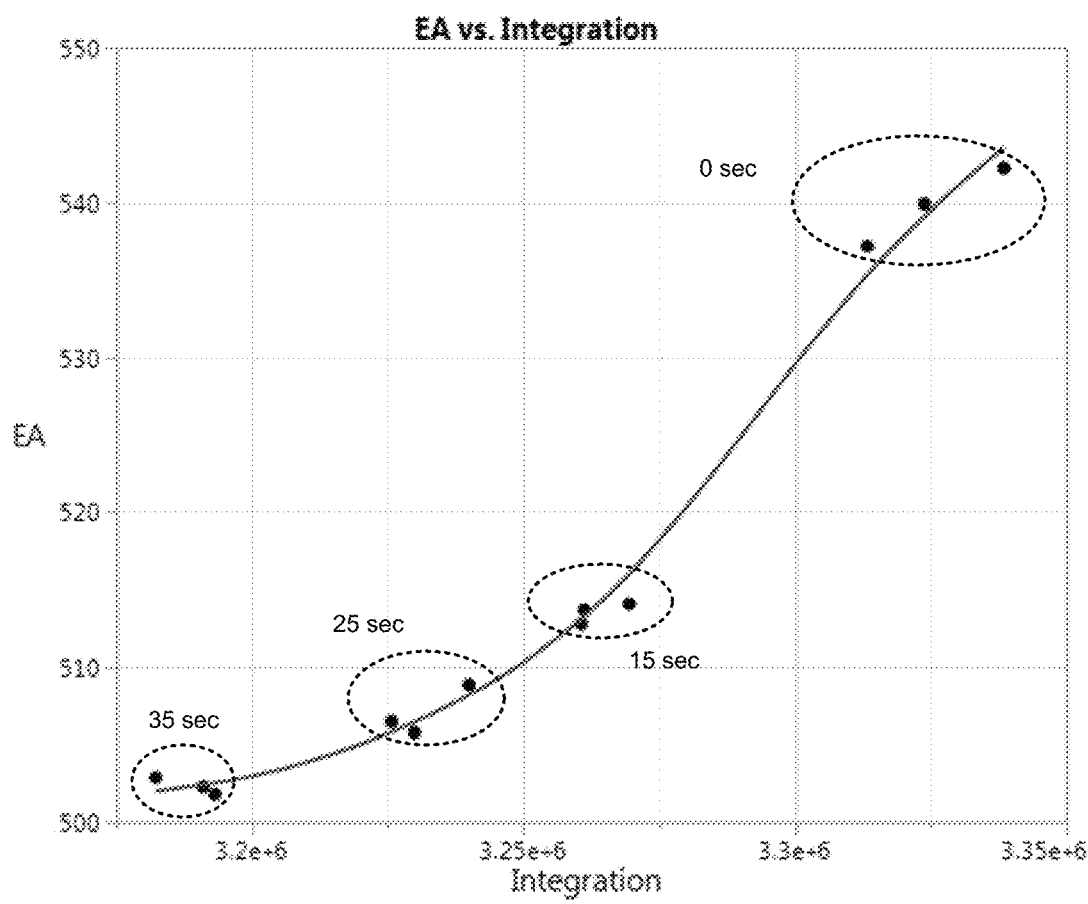
FIG. 5 shows a graph of the etch amount against the integrated intensity of hydrogen according to embodiments of the present technology.

FIG. 5 is a graph of the etch amount against the integrated intensity of hydrogen. The hydrogen signal was integrated over the time the layer was etched. For example, the hydrogen signal could be integrated over the time period shown in FIG. 4B, including from the rise of the intensity from near zero to the fall of the intensity back to zero. As seen in FIG. 5, the etch amount can be correlated to the integrated intensity. What is more, etches with the same ICC time are grouped together. This technique of integrating the signal shows a surprisingly improved correlation as compared to the non-integrated signal. FIG. 5 may be used as a calibration curve. In some embodiments, the curve fit may be represented as an equation, which may be used as a calibration curve.

II. Actinometry

Conventional actinometry includes adding a tracer gas with a similar threshold energy as the specie of interest. For example, argon may be included in the recipe to measure fluorine for optical emission purposes. The tracer is ideally inert. However, tracer gases may still perturb the process, especially with stringent device requirements. As a result, using an additional tracer gas may not be feasible with certain etches.

A. Method of Etching

Figure 6:
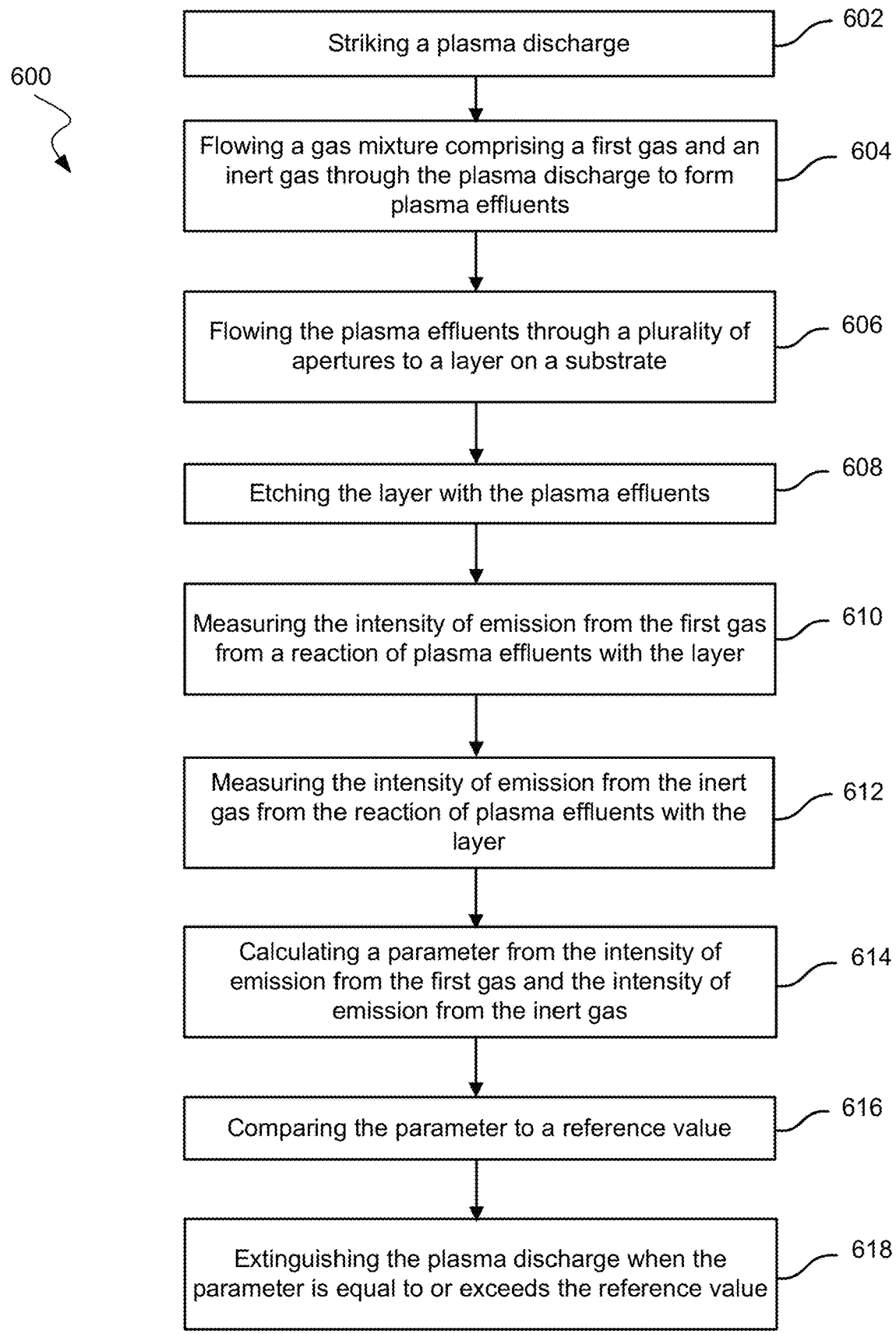
FIG. 6 shows a method of etching according to embodiments of the present technology.

FIG. 6 shows a method 600 of etching. Method 600 may include striking a plasma discharge (block 602). The plasma discharge may be any discharge described herein.

Method 600 may also include flowing a gas mixture through the plasma discharge to form plasma effluents (block 604). The gas mixture may include a first gas and an inert gas. The inert gas may be present in the gas mixture at a concentration above trace levels. For example, the concentration of the inert gas may be over 50%, over 60%, over 70%, or over 80% of the gas mixture. The first gas may be a hydrogen-containing gas, including HF. In some embodiments, the first gas may be a nitrogen-containing gas or a fluorine-containing gas. The inert gas may be helium. The gas mixture may exclude fluorine or argon as a tracer gas.

Method may further include flowing the plasma effluents through a plurality of apertures to a layer on a substrate (block 606). The layer may have a first thickness.

In addition, method 600 may include etching the layer with the plasma effluents (block 608). The rate of etching with the inert gas may be higher than if the inert gas was excluded from the gas mixture.

Method 600 may include measuring the intensity of emission from the first gas from a reaction of plasma effluents with the layer (block 610). The emission from the first gas may be emission at 656.3 nm, which may be emission from hydrogen. Emission from the first gas may include emission from F (e.g., 685.6 nm or 703.8 nm) or $N_2$ (e.g., 337.1 nm).

Method 600 may also include measuring the intensity of emission from the inert gas from the reaction of plasma effluents with the layer (block 612). The inert gas may be a gas with an emission with a fast radiative transition rate. The inert gas may have a similar excitation cross section as the first gas. For example, emission from the inert gas may include emission at 728.1 nm, which may include emission from helium. The transition for helium is about 50 ns. The transition for hydrogen at 656.3 nm is about 10 ns.

Method 600 may further include calculating a parameter from the intensity of emission from the first gas and the intensity of emission from the inert gas (block 614). Calculating the parameter may include the formula:

$$n_{inert} \times \frac{I_{first\ gas}}{I_{inert}},$$

where $n_{inert}$ is the density of the inert gas, $I_{first\ gas}$ is the intensity of emission from the first gas, and $I_{inert}$ is the intensity of emission from the inert gas. The density of the inert gas, $n_{inert}$, may be calculated from a model. The model may use an experimentally determined backdiffusion factor. For example, $n_{inert}$ may be calculated with the following equation:

$$n_{inert} = \frac{P_{inert}}{P_{inert} + \gamma P_{reactive}} \times \frac{kT}{P_{total}}$$

where $P_{inert}$ is the partial pressure of the inert gas, $P_{inert}$ is the partial pressure of the reactive gas (e.g., the first gas), $P_{total}$ is the total pressure, $\gamma$ is the backdiffusion factor, k is Boltzmann's constant, and T is temperature. The product of $n_{inert}$ with the ratio of $I_{first\ gas}$ and $I_{inert}$ may be the density of the first gas or proportional to the density of the first gas.

In some embodiments, method 600 may include summing the intensity of the emission from the first gas while the plasma effluents are flowed to the layer to obtain an integrated intensity of the first gas, similar to methods for summing intensity described herein. Method 600 may also include summing the intensity of emission from the inert gas while the plasma effluents are flowed to the layer to obtain an integrated intensity of the inert gas. Calculating the parameter may include calculating the parameter from the integrated intensity of the first gas and the integrated intensity of the inert gas.

At block 616, the parameter may be compared to a reference value that corresponds to a target thickness of the layer etched. The reference value may be obtained from a calibration curve, an equation, or from previously obtained data.

Method 600 may include extinguishing the plasma discharge when the parameter is equal to or exceeds the reference value (block 618). These operations in the method may then define a partially etched layer having a second thickness less than the first thickness.

B. Example

Figure 7:
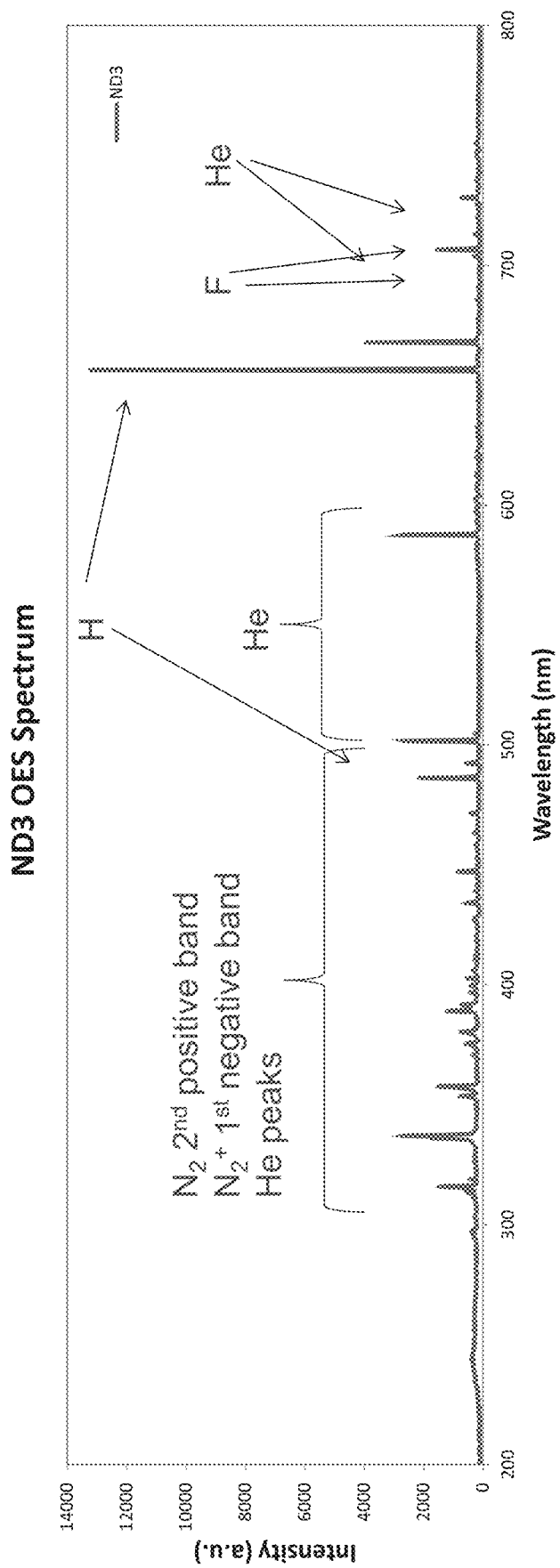
FIG. 7 depicts an example optical emission spectroscopy spectrum from a silicon etch recipe according to embodiments of the present technology.

FIG. 7 shows an example OES spectrum from a typical silicon etch recipe. The spectrum includes emission from H, He, F, and $N_2$. For example, peaks at for H (486.1 nm, 656.3 nm), F (703.8 nm), $N_2$ (337.1 nm), and He (504.8 nm, 667.8 nm, 706.5 nm, 728.1 nm) are shown. Conventional OES analysis involves analyzing strong peaks at the end of an etch step.

Figure 8:
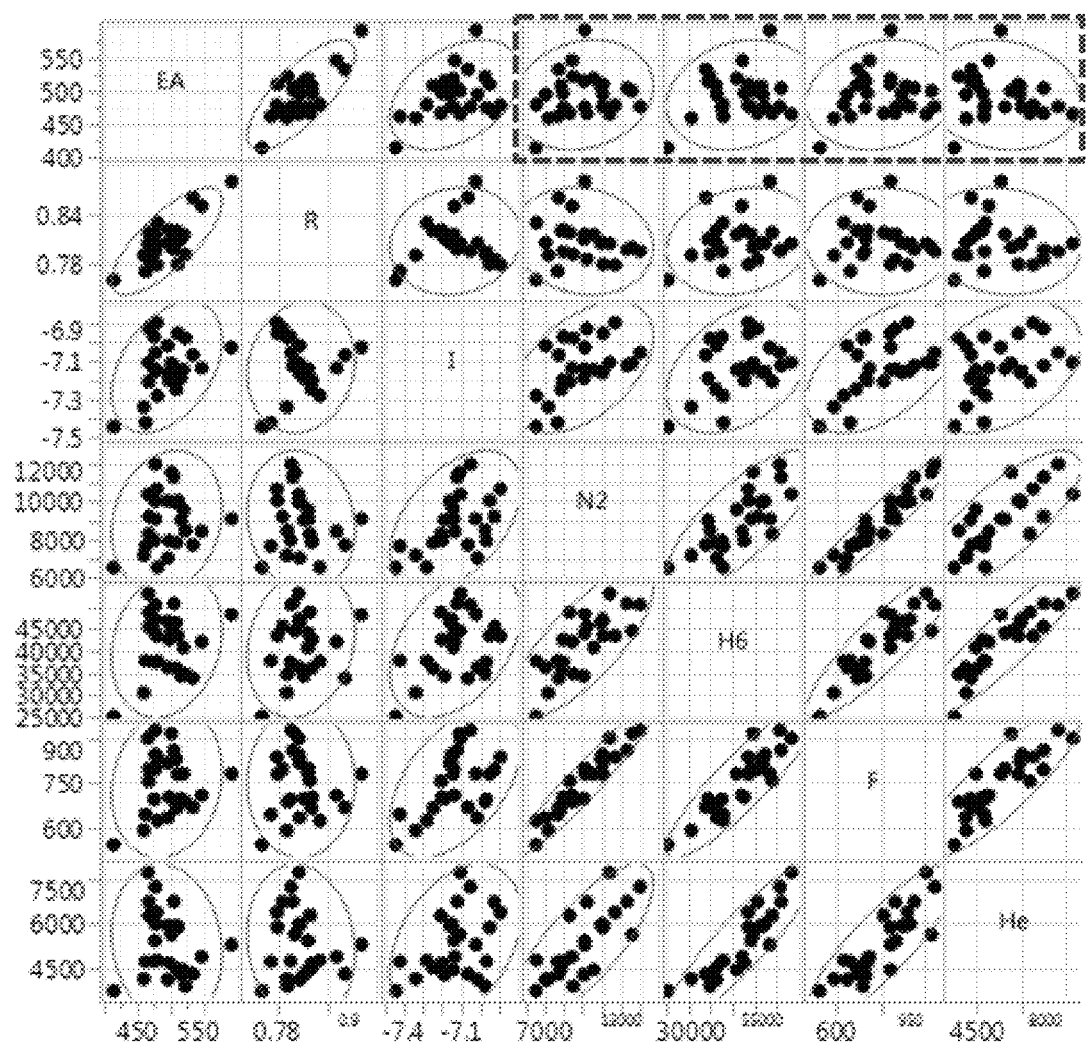
FIG. 8 shows the relationship between different parameters using conventional optical emission spectroscopy analysis according to embodiments of the present technology.

FIG. 8 shows the lack of correlation between different parameters using conventional OES analysis. The first row of the graph shows correlation with etch amount. The dashed box highlights the data that shows how etch amount depends on $N_2$, H, F, and He intensity. H6 denotes emission of hydrogen at 656.3 nm. There is little correlation between the etch amount and the intensities. The $R^2$ values are less than 0.05. R in FIG. 8 is resistance, and I is impedance. The $R^2$ value for resistance and etch amount is only about 0.57.

Figure 9:
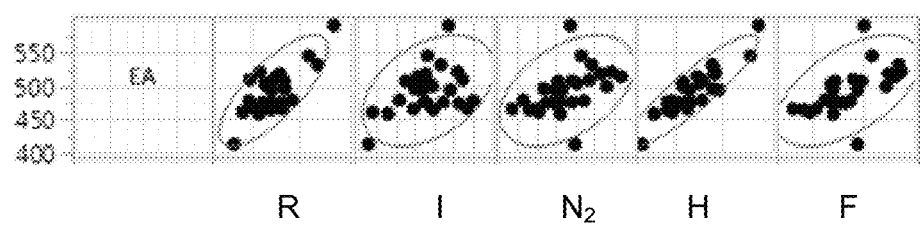
FIG. 9 shows the relationship between different parameters after actinometry using the helium signal according to embodiments of the present technology.

FIG. 9 shows the correlation between different parameters after actinometry using the helium signal. The data show a strong correlation with the H signal. The $R^2$ value for etch amount and hydrogen signal is about 0.81, while in FIG. 8, the $R^2$ value was less than 0.04. As a result, actinometry using the helium signal and the hydrogen signal may be correlated with the etch amount. In addition, other data support the validity of the actinometry model. In FIG. 9, the $N_2$ signal is linearly proportional to the F signal, which is expected because both these signals come from $NF_3$ dissociation.

III. Equipment

Figure 10:
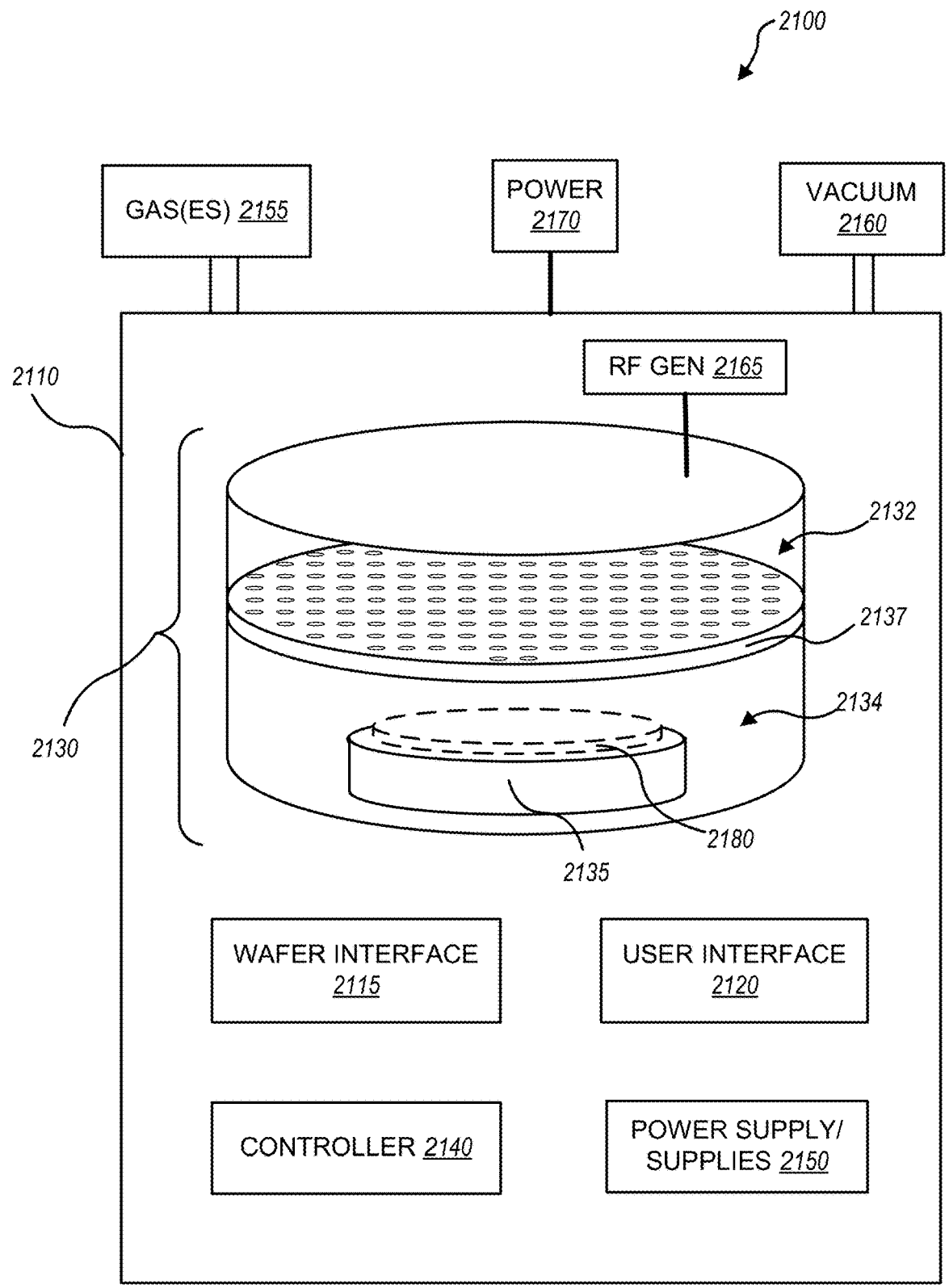
FIG. 10 schematically illustrates major elements of a plasma processing system, according to embodiments of the present technology.

FIG. 10 schematically illustrates major elements of a plasma processing system 2100, according to an embodiment. System 2100 is depicted as a single wafer, semiconductor wafer plasma processing system, but it will be apparent to one skilled in the art that the techniques and principles herein are applicable to plasma generation systems of any type (e.g., systems that do not necessarily process wafers or semiconductors). Processing system 2100 includes a housing 2110 for a wafer interface 2115, a user interface 2120, a plasma processing unit 2130, a controller 2140 and one or more power supplies 2150. Controller 2140 may include a processor to send and receive signals to various subsystems (e.g., wafer interface 2115, user interface 2120, plasma processing unit 2130, one or more power supplies 2150) in system 2100. Processing system 2100 is supported by various utilities that may include gas(es) 2155, external power 2170, vacuum 2160 and optionally others. Internal plumbing and electrical connections within processing system 2100 are not shown, for clarity of illustration.

Processing system 2100 is shown as a so-called indirect, or remote, plasma processing system that generates a plasma in a first location and directs the plasma and/or plasma products (e.g., ions, molecular fragments, energized species and the like) to a second location where processing occurs. Thus, in FIG. 10, plasma processing unit 2130 includes a remote plasma source 2132 that supplies plasma and/or plasma products for a process chamber 2134. Process chamber 2134 includes one or more wafer pedestals 2135, upon which wafer interface 2115 places a workpiece 2180 (e.g., a substrate or a semiconductor wafer, but could be a different type of workpiece) for processing. In operation, gas(es) 2155 are introduced into plasma source 2132 and a radio frequency generator (RF Gen) 2165 supplies power to ignite a plasma within plasma source 2132. Plasma and/or plasma products pass from plasma source 2132 through a diffuser plate 2137 to process chamber 2134, where workpiece 2180 is processed.

Although an indirect plasma processing system is illustrated in FIG. 10 and elsewhere in this disclosure, it should be clear to one skilled in the art that the techniques, apparatus and methods disclosed herein are equally applicable to direct plasma processing systems—e.g., where a plasma is ignited at the location of the workpiece(s). Similarly, in embodiments, the components of processing system 2100 may be reorganized, redistributed and/or duplicated, for example: (1) to provide a single processing system with multiple process chambers; (2) to provide multiple remote plasma sources for a single process chamber; (3) to provide multiple workpiece fixtures (e.g., wafer pedestals 2135) within a single process chamber; (4) to utilize a single remote plasma source to supply plasma products to multiple process chambers; and/or (5) to provide plasma and gas sources in serial/parallel combinations such that various source gases may be ionized zero, one, two or more times, and mixed with other source gases before or after they enter a process chamber, and the like.

Plasma Monitoring with OES

Figure 11:
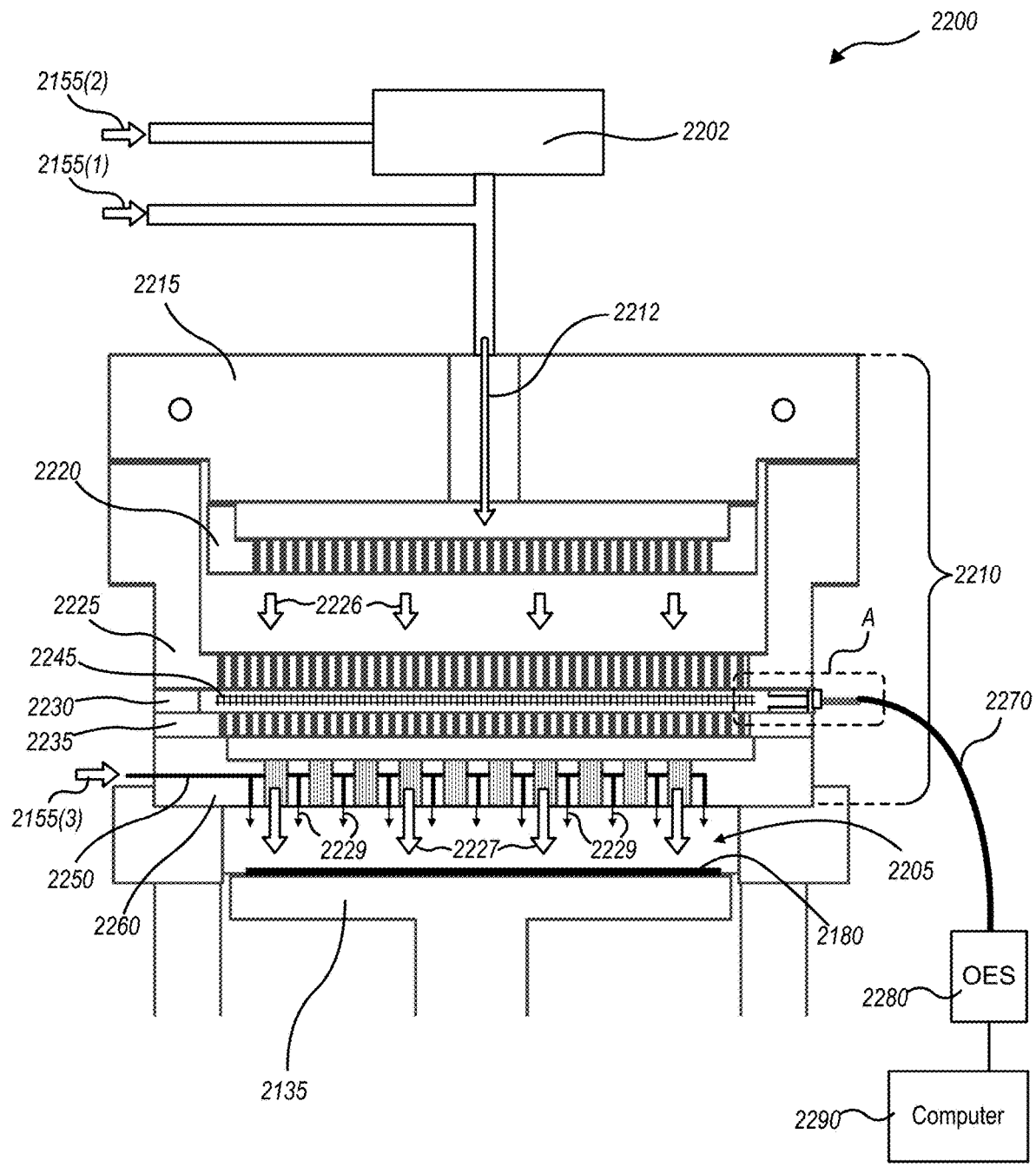
FIG. 11 schematically illustrates major elements of a plasma processing system, in a cross-sectional view, according to embodiments of the present technology.

FIG. 11 schematically illustrates major elements of a plasma processing system 2200, in a cross-sectional view, according to an embodiment. Plasma processing system 2200 is an example of plasma processing unit 2130, FIG. 10. Plasma processing system 2200 includes a process chamber 2205 and a plasma source 2210. As shown in FIG. 11, plasma source 2210 introduces gases 2155(1) directly, and/or gases 2155(2) that are ionized by an upstream remote plasma source 2202 (optional), as plasma source gases 2212, through an RF electrode 2215. In some embodiments, upstream remote plasma source 2202 may not be included, or no power may be applied to ignite a plasma in upstream remote plasma source 2202. RF electrode 2215 includes (e.g., is electrically tied to) a first gas diffuser 2220 and a face plate 2225 that serve to redirect flow of the source gases so that gas flow is uniform across plasma source 2210, as indicated by arrows 2231. After flowing through face plate 2225, an insulator 2230 electrically insulates RF electrode 2215 from a diffuser 2235 that is held at electrical ground (e.g., diffuser 2235 serves as a second electrode counterfacing face plate 2225 of RF electrode 2215). Surfaces of RF electrode 2215, diffuser 2235 and insulator 2230 define a plasma generation cavity (see plasma generation cavity 2240, FIG. 12) where a plasma 2245 is created when the source gases are present and RF energy is provided through RF electrode 2215. RF electrode 2215 and diffuser 2235 may be formed of any conductor, and in embodiments are formed of aluminum (or an aluminum alloy, such as the known "6061" alloy type). Surfaces of face plate 2225 and diffuser 2235 that face the plasma cavity or are otherwise exposed to reactive gases may be coated with yttria ($Y_2O_3$) or alumina ($Al_2O_3$) for resistance to the reactive gases and plasma products generated in the plasma cavity. Insulator 2230 may be any insulator, and in embodiments is formed of ceramic. A region denoted as A in FIG. 11 is shown in greater detail in FIG. 12. Emissions from plasma 2245 enter a fiber optic 2270 and are analyzed in an optical emission spectrometer 2280, as discussed further below.

Plasma products generated in plasma 2245 pass through diffuser 2235 that again helps to promote the uniform distribution of plasma products, and may assist in electron temperature control. Upon passing through diffuser 2235, the plasma products pass through a further diffuser 2260 that promotes uniformity as indicated by small arrows 2227, and enter process chamber 2205 where they interact with workpiece 2180, such as a semiconductor wafer, atop wafer pedestal 2135. Diffuser 2260 includes further gas channels 2250 that may be used to introduce one or more further gases 2155(3) to the plasma products as they enter process chamber 2205, as indicated by very small arrows 2229.

Embodiments herein may be rearranged and may form a variety of shapes. For example, RF electrode 2215 and diffuser 2235 are substantially radially symmetric in the embodiment shown in FIG. 11, and insulator 2230 is a ring with upper and lower planar surfaces that are disposed against peripheral areas of face plate 2225 and diffuser 2235, for an application that processes a circular semiconductor wafer as workpiece 2180. However, such features may be of any shape that is consistent with use as a plasma source. Moreover, the exact number and placement of features for introducing and distributing gases and/or plasma products, such as diffusers, face plates and the like, may also vary. Also, in a similar manner to diffuser 2260 including gas channels 2250 to add gas 2155(3) to plasma products from plasma 2245 as they enter process chamber 2205, other components of plasma processing system 2200 may be configured to add or mix gases 2155 with other gases and/or plasma products as they make their way through the system to process chamber 2205.

Figure 12:
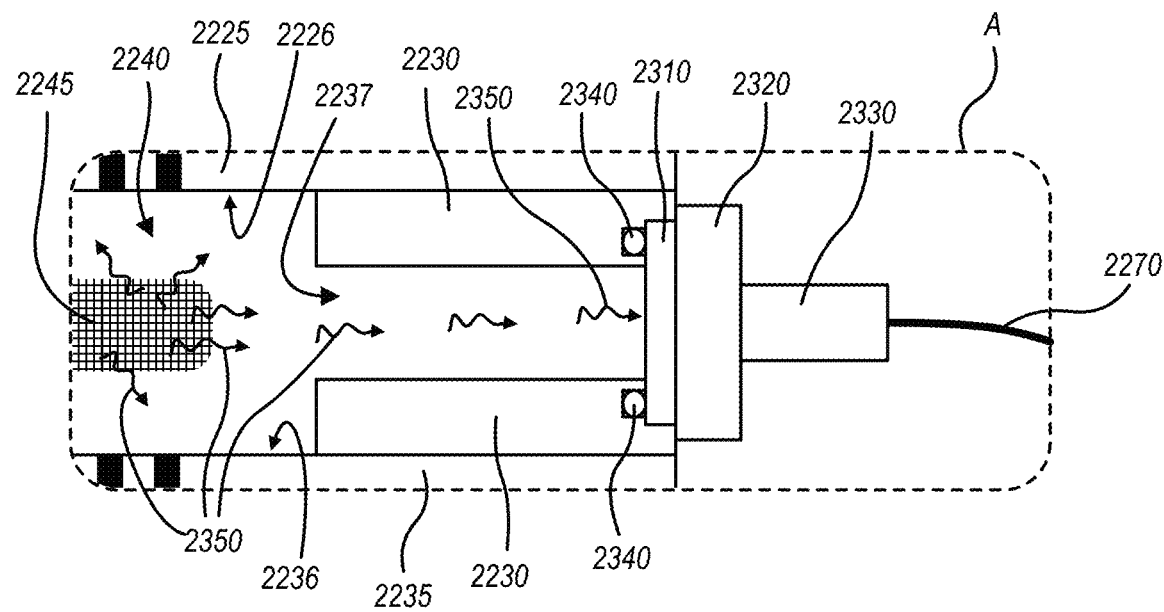
FIG. 12 schematically illustrates details of region A shown in FIG. 11 according to embodiments of the present technology.

FIG. 12 schematically illustrates details of region A shown in FIG. 11. Face plate 2225, insulator 2230 and diffuser 2235 seal to one another such that a plasma generation cavity 2240 that is bounded by face plate 2225, insulator 2230 and diffuser 2235 can be evacuated. A facing surface 2226 of face plate 2225, and/or a facing surface 2236 of diffuser 2235 may be coated with yttria ($Y_2O_3$) or alumina ($Al_2O_3$) for resistance to the gases and/or plasmas to be used.

When plasma source gases are introduced and electrical power is provided across face plate 2225 and diffuser 2235, a plasma 2245 can form therein. Insulator 2230 forms a radial aperture 2237; an optical window 2310 seals to insulator 2230 over aperture 2237. Optical window 2310 is formed of sapphire, however it is appreciated that other materials for optical window 2310 may be selected based on resistance to plasma source gases and/or plasma products of plasma 2245, or transmissivity to optical emissions, as discussed below. In the embodiment shown in FIG. 12, an o-ring 2340 seats in recesses 2345 to facilitate sealing optical window 2310 to insulator 2230; however, other sealing geometries and methods may be utilized. In embodiments, plasma generation cavity 2240 is evacuated such that atmospheric pressure (external to plasma generation cavity 2240) assists in sealing components such as optical window 2310 to insulator 2230.

Fiber optic 2270 is positioned such that when plasma 2245 exists in plasma generation cavity 2240, optical emissions 2350 originate in plasma 2245, propagate through radial aperture 2237 and optical window 2310, and into fiber optic 2270 to generate an optical signal therein. Fiber optic 2270 transmits optical emissions 2350 to optical emission spectrometer 2280, FIG. 11. In embodiments, fiber optic 2270 is a 400 μm core optical fiber; however, other core sizes and various fiber materials may be selected for transmissivity of optical emissions 2350 and to manage signal strength within fiber optic 2270. For example, plasmas 2245 that generate low levels of optical emissions 2350 may be monitored utilizing a relatively wide core (e.g., 400 μm) fiber optic 2270, while plasmas that generate higher levels of optical emissions 2350 may be monitored utilizing relatively narrower cores (e.g., 110 μm, 100 μm, 62.5 μm, 50 μm, 9 μm or other core sizes) in order to limit the optical signal reaching optical emission spectrometer 2280. One or more filters may be utilized at optical emission spectrometer 2280 to absorb stray light and/or emissions that are not within a spectral band of interest.

Optical emission spectrometer 2280 analyzes the optical signal received from fiber optic 2270 to identify emission peaks within the signal, including identifying specific emission peaks as corresponding to energy transitions of specific elements. In some embodiments, spectra and/or information characterizing emission peaks therein may be viewed and/or manipulated on optical emission spectrometer 2280. In some of these and in other embodiments, emission peak information may be transferred to a computer 2290 for analysis, manipulation, storage and/or display. Computer 2290 may include a processor, and computer 2290 may send and receive signals from other parts of plasma processing system 2200.

In embodiments, a fiber optic connector 2330 terminates fiber optic 2270, and a block 2320 positions fiber optic connector 2330 with respect to optical window 2310, as shown in FIG. 12. However, this arrangement is by way of example only; other embodiments may provide a custom termination of fiber optic 2270 that does not involve a connector 2330, and various arrangements for positioning fiber optic 2270 and/or connector 2330 with respect to window 2310 may be implemented in place of block 2320. When utilized, block 2320 may extend in and out of the cross-sectional plane shown in FIG. 12 to form attachment regions, and may fasten to insulator 2230 using fasteners such as screws in such regions. Block 2320 and/or screws that attach block 2320 to insulator 2230 are advantageously fabricated of insulative materials such as plastic or ceramic, to mitigate any possibility of electrical arcing to or from face plate 2225 and diffuser 2235, and/or other structures.

It is appreciated that aperture 2237 and optical window 2310, at least, function as a port for providing an optical signal from plasma 2245 that can be utilized to monitor aspects of plasma source 2210. It is also appreciated that such port may be provided at a variety of locations within a plasma source. For example, generally speaking, a capacitively coupled plasma source will include at least two electrodes separated by an insulator; a port such as described above could be disposed with any of the electrodes or the insulator. Similarly, an inductively coupled plasma source (or any other type of plasma source) could include a port disposed with any vessel in which the plasma is initially generated. Materials and/or locations of such ports should be selected so as not to disrupt electrical or magnetic circuits that are important to the plasma source (e.g., to mitigate arcing and/or disturbance of magnetic field distributions, for inductively coupled plasma sources).

Returning to FIG. 11, optical monitoring of plasma at the place where it is generated in a remote plasma source provides unique benefits. Because plasma 2245 is monitored upstream of its interactions with a workpiece 2180 (e.g., a wafer), the monitoring provides characterization of the plasma source alone, which may be contrasted or correlated with effects produced by interaction with the workpiece. That is, the geometry of insulator 2230 and radial aperture 2237 will tend to provide fiber optic 2270 with an effective "view" that is limited to optical emissions resulting from plasma 2245 and interactions of those emissions with adjacent surfaces, rather than emissions resulting from downstream interactions and/or direct views of surfaces within a process chamber. Monitoring of a plasma at a location where it has not yet had an opportunity to interact with a workpiece is called "upstream" plasma monitoring herein.

By way of contrast, optical monitoring of workpieces themselves, and/or plasma interaction with such workpieces, may be used to monitor certain plasma effects on the workpiece, but are susceptible to influence by the workpiece. Workpiece-affected plasma characteristics, including optical emissions captured with optical probes, are sometimes utilized to determine a plasma processing endpoint, that is, to identify a time at which processing is essentially complete such that some aspect of the plasma process can be turned off. For example, interaction with a workpiece can affect a plasma by releasing reaction products from the workpiece, and/or the workpiece can deplete reactive species from the plasma. When reaction products from the workpiece are no longer detected, it may signify that a layer to be etched has "cleared" such that etch gases and/or RF energy can be turned off. However, such optical probes are situated where the optical emissions that are captured are affected by the workpiece.

Both workpiece-affected and upstream plasma monitoring can be useful tools in determining whether variations in processed workpieces are due to variations in a plasma as generated, or due to variations present in the workpieces before they interact with the plasma. In certain embodiments herein, stable process results correlate strongly with upstream plasma monitoring results. Specifically, process results have been found to correlate with certain emission peaks measured with the apparatus described in connection with FIGS. 11 and 12. When strong correlations between upstream monitoring of plasma emission peaks and process results can be identified, it becomes possible, in embodiments, to run conditioning process cycles without exposing valuable workpieces to risk until those emission peaks are observed to be stable. Once the emission peaks are stable, workpieces can be processed in confidence that the process results will be as expected.

Stability in emission peaks obtained from upstream monitoring can indicate equilibrium in reactions between the generated plasma and adjacent surfaces. For example, certain surfaces of electrodes, diffusers and the like may interact with a plasma to slowly give off, or absorb, certain elements that are important to process results, such that the resulting plasma process will not be stable until the surfaces are in equilibrium with the plasma. In embodiments, electrodes, diffusers and the like may be coated with refractory materials such as yttria ($Y_2O_3$) or alumina ($Al_2O_3$) for resistance to the gases and/or plasmas to be used. These materials can interact with plasma products such as free hydrogen, such that plasmas generated around such surfaces may not be stable until the surfaces are either saturated or substantially depleted of hydrogen. In either case, emission peaks generated through upstream plasma monitoring can be useful for assessing plasma stability.

Accurately identifying when plasma equipment is running a stable process is valuable in the semiconductor industry. Semiconductor processing is characterized both by unusable equipment having high cost and workpieces having high value that is at risk if processing is not optimal. For example, a single plasma processing system may represent hundreds of thousands, or a few million dollars of capital investment, with output of a multimillion dollar wafer fabrication area being dependent on only a few of such systems. Yet, a single semiconductor wafer may accrue hundreds or thousands of dollars of invested processing costs, and a piece of plasma equipment might process tens of such wafers per hour. Thus the financial costs of equipment downtime, or of utilizing equipment that is not operating correctly, are both quite high.

IV. Computer System

Figure 13:
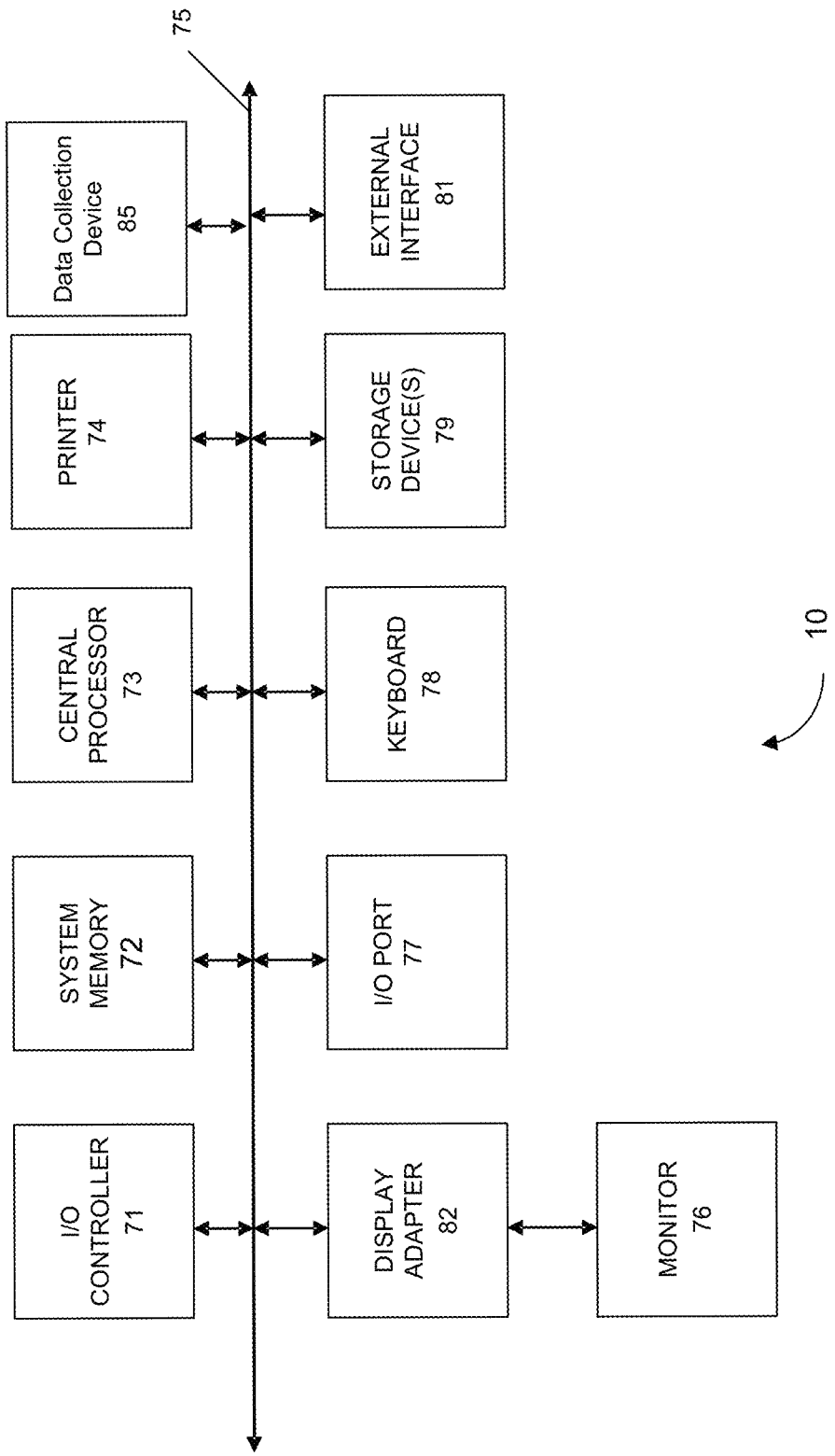
FIG. 13 shows a computer system according to embodiments of the present technology.

Any of the computer systems mentioned herein may utilize any suitable number of subsystems. Examples of such subsystems are shown in FIG. 13 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 13 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire®, Thunderbolt). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

In the preceding description, for the purposes of explanation, numerous details have been set forth in order to provide an understanding of various embodiments of the present technology. It will be apparent to one skilled in the art, however, that certain embodiments may be practiced without some of these details, or with additional details.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the gas" includes reference to one or more gases and equivalents thereof known to those skilled in the art, and so forth. The invention has now been described in detail for the purposes of clarity and understanding. However, it will be appreciated that certain changes and modifications may be practice within the scope of the appended claims.

All publications, patents, and patent applications cited herein are hereby incorporated by reference in their entirety for all purposes. None is admitted to be prior art.

What is claimed is:

1. A method of etching, the method comprising:
   striking a plasma discharge;
   flowing a gas mixture comprising a hydrogen-containing gas and helium through the plasma discharge to form plasma effluents;
   flowing the plasma effluents through a plurality of apertures to a silicon layer on a substrate, the silicon layer having a first thickness;
   etching the silicon layer with the plasma effluents;
   measuring the intensity of emission from hydrogen from a reaction of plasma effluents with the silicon layer;
   measuring the intensity of emission from helium in the plasma effluents;
   integrating the intensity of the emission from helium over the duration the plasma effluents are being flowed to the silicon layer to obtain an integrated intensity of helium;
   integrating the intensity of the emission from hydrogen over the duration the plasma effluents are being flowed to the silicon layer to obtain an integrated intensity of hydrogen;
   calculating a parameter from the integrated intensity of hydrogen and the integrated intensity of helium;
   comparing the parameter to a reference value corresponding to a target thickness of silicon etched;
   extinguishing the plasma discharge when the integrated intensity is equal to or greater than the reference value to define a partially etched silicon layer on the substrate having a second thickness less than the first thickness.

2. The method of claim 1, wherein the second thickness is less than or equal to the first thickness minus the target thickness.

3. The method of claim 1, wherein the emission from hydrogen comprises emission at 656.3 nm.

4. The method of claim 1, wherein integrating the intensity of the emission from helium is over the entire duration of the plasma effluents being flowed to the layer.

5. The method of claim 4, wherein the entire duration is in a range from 60 seconds to 600 seconds.

6. The method of claim 1, further comprising obtaining the reference value from a calibration curve relating integrated intensity to target thickness or calculating the reference value from an equation relating integrated intensity to target thickness.

7. The method of claim 1, further comprising:
reacting plasma effluents with the layer at a pressure greater than or equal to 1 Torr.

8. The method of claim 1, wherein a difference between the second thickness and the first thickness is within 10% of the target thickness.

9. The method of claim 1, wherein determining when to extinguish the plasma discharge excludes using emission from fluorine.

10. The method of claim 1, wherein:
flowing the plasma effluents through the plurality of apertures to the silicon layer is in a chamber, and
the method further comprising removing the substrate from the chamber after extinguishing the plasma discharge.

11. The method of claim 1, wherein the gas mixture comprises a fluorine-containing gas.

12. The method of claim 1, wherein the substrate is a silicon wafer.

13. A method of measuring an amount of a silicon layer etched with a plasma source, the method comprising:
measuring the intensity of emission from hydrogen from a reaction of plasma effluents with the silicon layer;
measuring the intensity of emission from helium in the plasma effluents;
integrating the intensity of the emission from helium over the duration that the plasma effluents are being flowed to the silicon layer to obtain an integrated intensity of helium;
integrating the intensity of the emission from hydrogen over the duration the plasma effluents are being flowed to the silicon layer to obtain an integrated intensity of hydrogen;
calculating a parameter from the integrated intensity of hydrogen and the integrated intensity of helium; and
measuring the amount of the silicon layer etched by comparing the parameter to a calibration curve.

14. The method of claim 13, wherein the emission from hydrogen is a wavelength associated with a species in the plasma effluents.

15. The method of claim 13, wherein the amount of the silicon layer etched is less than a thickness of the silicon layer before the plasma effluents are flowed to the silicon layer.

16. The method of claim 13, wherein integrating the intensity of the emission from hydrogen is over the entire duration of the plasma effluents being flowed to the silicon layer.

17. The method of claim 13, wherein the calibration curve relates previously obtained intensity values with etch amounts.

18. The method of claim 13, wherein the silicon layer is on top of a silicon wafer.

* * * * *